United States Patent
Kasahara et al.

(10) Patent No.: US 8,895,574 B2
(45) Date of Patent: Nov. 25, 2014

(54) BENZYLOXYPYRIMIDINE DERIVATIVE, AGRICULTURAL/ HORTICULTURAL INSECTICIDE COMPRISING DERIVATIVE AND METHOD FOR USING SAME

(75) Inventors: Ryota Kasahara, Kawachinagano (JP); Hiroto Harayama, Kawachinagano (KR); Eikou Satoh, Kawachinagano (JP); Motofumi Nakano, Kawachinagano (JP); Kosuke Fukatsu, Kawachinagano (JP); Kayo Inukai, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 13/994,554

(22) PCT Filed: Dec. 22, 2011

(86) PCT No.: PCT/JP2011/079847
§ 371 (c)(1),
(2), (4) Date: Jun. 14, 2013

(87) PCT Pub. No.: WO2012/086768
PCT Pub. Date: Jun. 28, 2012

(65) Prior Publication Data
US 2013/0267564 A1    Oct. 10, 2013

(30) Foreign Application Priority Data

Dec. 24, 2010  (JP) ................................. 2010-287777
Aug. 23, 2011  (JP) ................................. 2011-181052

(51) Int. Cl.
| | |
|---|---|
| A61K 31/505 | (2006.01) |
| A01N 43/54 | (2006.01) |
| C07D 239/56 | (2006.01) |
| C07D 403/12 | (2006.01) |
| C07D 239/52 | (2006.01) |
| A01N 43/60 | (2006.01) |
| A01N 43/56 | (2006.01) |
| C07D 239/46 | (2006.01) |
| A01N 43/40 | (2006.01) |
| C07D 401/12 | (2006.01) |
| C07D 239/34 | (2006.01) |

(52) U.S. Cl.
CPC .............. *A01N 43/40* (2013.01); *C07D 239/56* (2013.01); *C07D 403/12* (2013.01); *C07D 239/52* (2013.01); *A01N 43/60* (2013.01); *A01N 43/56* (2013.01); *C07D 239/46* (2013.01); *C07D 401/12* (2013.01); *A01N 43/54* (2013.01); *C07D 239/34* (2013.01)
USPC .......................................... 514/269; 544/319

(58) Field of Classification Search
CPC ........................... C07D 239/52; C07D 239/59
USPC ......................................................... 544/319
See application file for complete search history.

(56) References Cited

U.S. PATENT DOCUMENTS

| | | | |
|---|---|---|---|
| 5,246,938 A | * 9/1993 | Turnbull et al. | .............. 514/274 |
| 5,859,020 A | * 1/1999 | Preuss et al. | .................. 514/269 |
| 6,114,342 A | 9/2000 | Oberdorf et al. | |
| 6,310,071 B1 | 10/2001 | Oberdorf et al. | |
| 2010/0113490 A1 | 5/2010 | Liu et al. | |

FOREIGN PATENT DOCUMENTS

| | | |
|---|---|---|
| WO | WO 93/06091 A1 | 4/1993 |
| WO | WO 97/21686 A1 | 6/1997 |
| WO | WO 2000/049001 A2 | 8/2000 |
| WO | WO 2008/009691 A1 | 1/2008 |
| WO | WO 2008/145052 A1 | 12/2008 |
| WO | WO 2010/064688 A1 | 6/2010 |

OTHER PUBLICATIONS

L. M. Abell et al. Target-Site Directed Herbicide Design in, Pest Control With Enhanced Environmental Safety 15-37 (ACS Symposium Series; American Chemical Society, S. Duke, et al. eds, 1993).*
S.C. Knight et al., Annual Review of Phytopathology 35, 349-372, 357 (1997).*
W.T. Ruegg et al., Weed Research, 47(4), 271-275, 271 (2006).*
Japanese Patent Office, International Search Report in International Patent Application No. PCT/JP2011/079847 (Jan. 24, 2012).
International Bureau of WIPO, International Preliminary Report on Patentability in International Patent Application No. PCT/JP2011/079847 (Jul. 2, 2013).
European Patent Office, Extended European Search Report in European Patent Application No. 11850017.2 (Jun. 20, 2014).

* cited by examiner

*Primary Examiner* — James O. Wilson
*Assistant Examiner* — Alexander R Pagano
(74) *Attorney, Agent, or Firm* — Leydig, Voit & Mayer, Ltd.

(57) ABSTRACT

A benzyloxypyrimidine derivative represented by the formula (I)

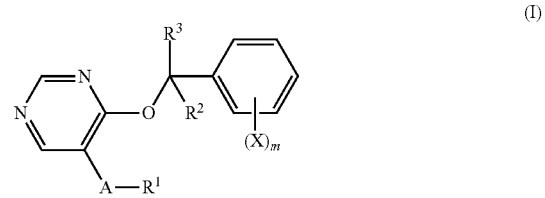

wherein $R^1$ is an alkyl group, a cycloalkyl group, an alkenyl group, an alkynyl group, a haloalkyl group, a haloalkenyl group, a haloalkynyl group, an alkoxyalkyl group and the like; $R^2$ and $R^3$ are each a hydrogen atom, an alkyl group and the like; X is an alkyl group, a cycloalkyl group, an alkenyl group, an alkynyl group, a haloalkyl group, a haloalkenyl group, a haloalkynyl group, a trialkylsilyl group and the like; A is a oxygen atom and the like, and m is an integer of 0-5, or a salt thereof, and an agrohorticultural insecticide containing the compound as an active ingredient and a method of use thereof.

14 Claims, No Drawings

BENZYLOXYPYRIMIDINE DERIVATIVE, AGRICULTURAL/HORTICULTURAL INSECTICIDE COMPRISING DERIVATIVE AND METHOD FOR USING SAME

CROSS-REFERENCE TO RELATED APPLICATIONS

This patent application is the U.S. national phase of International Patent Application No. PCT/JP2011/079847, filed Dec. 22, 2011, which claims the benefit of Japanese Patent Application No. 2010-287777, filed on Dec. 24, 2010, and Japanese Patent Application No. 2011-181052, filed Aug. 23, 2011, which are incorporated by reference in their entireties herein.

TECHNICAL FIELD

The present invention relates to an agrohorticultural insecticide containing a novel pyrimidine derivative or a salt thereof as an active ingredient, and a method of use thereof.

BACKGROUND ART

While the pyrimidine derivative described in patent document 1 is disclosed to be useful as an insecticide, it has a different structure from the pyrimidine derivative of the present invention. While the pyrimidine derivative described in patent document 2 is disclosed to be useful as an insecticide, a compound having a substituent disclosed in the present invention at the 4-position of pyrimidine is not disclosed.

patent document 1: WO 2010/064688
patent document 2: WO 1993/006091

SUMMARY OF THE INVENTION

Problems to be Solved by the Invention

In crop manufacturing in agricultural and horticultural fields, damages caused by insect pests are still serious, and development of novel agrohorticultural insecticides and acaricides is desired due to generation of insect pests resistant to known agents, and the like. Since various labor saving farm works are required due to increasing numbers of the aged farm working population, creation of agrohorticultural insecticides having suitable properties for the farm works is also demanded.

Means of Solving the Problems

The present inventors have conducted intensive studies in an attempt to develop a novel agrohorticultural insecticide, and have found that the benzyloxypyrimidine derivative represented by the formula (I) of the present invention is a novel compound not described in literatures, and useful as an agrohorticultural insecticide, which resulted in the completion of the present invention.

Accordingly, the present invention relates to

[1] a benzyloxypyrimidine derivative represented by the formula (I):

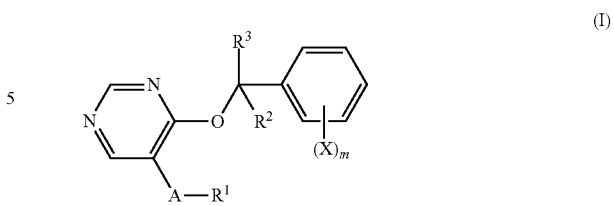

wherein, $R^1$ is
(a1) a hydrogen atom;
(a2) a $(C_1-C_6)$alkyl group;
(a3) a $(C_3-C_7)$cycloalkyl group (said cycloalkyl group is optionally fused with a benzene ring);
(a4) a $(C_2-C_6)$alkenyl group;
(a5) a $(C_2-C_6)$alkynyl group;
(a6) a halo$(C_1-C_6)$alkyl group;
(a7) a halo$(C_3-C_6)$cycloalkyl group;
(a8) a halo$(C_2-C_6)$alkenyl group;
(a9) a halo$(C_2-C_6)$alkynyl group;
(a10) a $(C_1-C_6)$alkoxy$(C_1-C_6)$alkyl group;
(a11) a $(C_3-C_6)$cycloalkyl$(C_1-C_6)$alkyl group;
(a12) a $(C_1-C_6)$alkylthio$(C_1-C_6)$alkyl group;
(a13) a $(C_1-C_6)$alkylsulfinyl$(C_1-C_6)$alkyl group;
(a14) a $(C_1-C_6)$alkylsulfonyl$(C_1-C_6)$alkyl group;
(a15) a halo$(C_1-C_6)$alkoxy$(C_1-C_6)$alkyl group;
(a16) a halo$(C_3-C_6)$cycloalkyl$(C_1-C_6)$alkyl group;
(a17) a halo$(C_1-C_6)$alkylthio$(C_1-C_6)$alkyl group;
(a18) a halo$(C_1-C_6)$alkylsulfinyl$(C_1-C_6)$alkyl group;
(a19) a halo$(C_1-C_6)$alkylsulfonyl$(C_1-C_6)$alkyl group;
(a20) a $(C_1-C_6)$alkoxyhalo$(C_1-C_6)$alkyl group;
(a21) a halo$(C_1-C_6)$alkoxyhalo$(C_1-C_6)$alkyl group;
(a22) an aryl$(C_1-C_6)$alkyl group;
(a23) an aryl$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_3-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)N$ carbonyl group wherein $R^4$ and $R^5$ may be the same or different and each is a hydrogen atom, a $(C_1-C_6)$alkyl group, a $(C_3-C_6)$cycloalkyl group, a $(C_2-C_6)$alkenyl group, a $(C_2-C_6)$alkynyl group, a $(C_3-C_6)$cycloalkyl$(C_1-C_6)$alkyl group, a halo$(C_1-C_6)$alkyl group, a halo$(C_3-C_6)$cycloalkyl group, a halo$(C_2-C_6)$alkenyl group, a halo$(C_2-C_6)$alkynyl group, a halo$(C_3-C_6)$cycloalkyl$(C_1-C_6)$alkyl group, a phenyl group, or a phenyl$(C_1-C_6)$alkyl group;
(a24) a cyano$(C_1-C_6)$alkyl group;
(a25) a nitro $(C_1-C_6)$alkyl group;
(a26) a $R^4(R^5)N(C_1-C_6)$alkyl group wherein $R^4$ and $R^5$ are as defined above;
(a27) a $(R^4)OC(C_1-C_6)$alkyl group wherein $R^4$ is as defined above;
(a28) a $(R^4)O_2C(C_1-C_6)$alkyl group wherein $R^4$ is as defined above;
(a29) a $R^4(R^5)NCO(C_1-C_6)$alkyl group wherein $R^4$ and $R^5$ are as defined above;
(a30) an aryl group;
(a31) an aryl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)$N carbonyl group wherein $R^4$ and $R^5$ are as defined above, and (t) a phenoxy group;

(a32) an arylsulfonyl group;

(a33) an arylsulfonyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)$N carbonyl group wherein $R^4$ and $R^5$ are as defined above;

(a34) an arylcarbonyl group;

(a35) an arylcarbonyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)$N carbonyl group wherein $R^4$ and $R^5$ are as defined above;

(a36) an arylthio$(C_1-C_6)$alkyl group;

(a37) an arylthio$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)$N carbonyl group wherein $R^4$ and $R^5$ are as defined above;

(a38) an arylsulfinyl$(C_1-C_6)$alkyl group;

(a39) an arylsulfinyl$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)$N carbonyl group wherein $R^4$ and $R^5$ are as defined above;

(a40) an arylsulfonyl$(C_1-C_6)$alkyl group;

(a41) an arylsulfonyl$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)$N carbonyl group wherein $R^4$ and $R^5$ are as defined above;

(a42) an arylcarbonyloxy$(C_1-C_6)$alkyl group;

(a43) an arylcarbonyloxy$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)$N carbonyl group wherein $R^4$ and $R^5$ are as defined above;

(a44) a $(C_1-C_6)$alkylcarbonyl group;

(a45) a $(C_1-C_6)$alkoxycarbonyl group;

(a47) a $R^4(R^5)$N carbonyloxy$(C_1-C_6)$alkyl group wherein $R^4$ and $R^5$ are as defined above;

(a48) a tri$(C_1-C_6)$alkylsilyl group wherein the alkyl groups may be the same or different;

(a49) a $(C_1-C_6)$alkoxy$(C_1-C_6)$alkoxy$(C_1-C_6)$alkyl group;

(a50) a $(C_1-C_6)$alkoxycarbonyloxy$(C_1-C_6)$alkyl group;

(a51) a $(C_1-C_6)$alkyl$(C_1-C_6)$sulfonyl group;

(a52) a heterocyclic group;

(a53) a heterocyclic group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)$N carbonyl group wherein $R^4$ and $R^5$ are as defined above, and (t) an oxo group;

(a54) a heterocyclyl$(C_1-C_6)$alkyl group;

(a55) a heterocyclyl$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)$N carbonyl group wherein $R^4$ and $R^5$ are as defined above, and (t) an oxo group;

(a56) a tri($C_1$-$C_6$)alkylsilyl($C_1$-$C_6$)alkyl group wherein the alkyl groups of the tri($C_1$-$C_6$)alkylsilyl may be the same or different; or
(a57) a $R^4(R^5)$NCO group wherein $R^4$ and $R^5$ are as defined above,
A is —O—, —S—, —SO— or —$SO_2$—.
$R^2$ and $R^3$ may be the same or different, and each is
(b1) a hydrogen atom;
(b2) a ($C_1$-$C_6$)alkyl group;
(b3) a ($C_3$-$C_6$)cycloalkyl group;
(b4) a ($C_2$-$C_6$)alkenyl group;
(b5) a ($C_2$-$C_6$)alkynyl group;
(b6) a halo($C_1$-$C_6$)alkyl group;
(b7) a halo($C_3$-$C_6$)cycloalkyl group;
(b8) a halo($C_2$-$C_6$)alkenyl group;
(b9) a halo($C_2$-$C_6$)alkynyl group;
(b10) a ($C_3$-$C_6$)cycloalkyl($C_1$-$C_6$)alkyl group;
(b11) a ($C_1$-$C_6$)alkoxy($C_1$-$C_6$)alkyl group;
(b12) a ($C_1$-$C_6$)alkylthio($C_1$-$C_6$)alkyl group; or
(b13) a ($C_1$-$C_6$)alkoxycarbonyl group,
X may be the same or different, and each is
(c1) a hydrogen atom;
(c2) a halogen atom;
(c3) a hydroxyl group;
(c4) a cyano group;
(c5) a nitro group;
(c6) a $N(R^4)(R^5)$ group wherein $R^4$ and $R^5$ are as defined above;
(c7) a $N(R^4)CO(R^5)$ group wherein $R^4$ and $R^5$ are as defined above;
(c8) a $N(R^4)SO_2(R^5)$ group wherein $R^4$ and $R^5$ are as defined above;
(c9) a $N(R^4)CO_2(R^5)$ group wherein $R^4$ and $R^5$ are as defined above;
(c10) a $CO(R^4)$ group wherein $R^4$ is as defined above;
(c11) a $CO_2(R^4)$ group wherein $R^4$ is as defined above;
(c12) a $CON(R^4)(R^5)$ group wherein $R^4$ and $R^5$ are as defined above;
(c13) a $C(R^4)$=$NOR^5$ group wherein $R^4$ and $R^5$ are as defined above;
(c14) a ($C_1$-$C_{12}$)alkyl group;
(c15) a ($C_2$-$C_{12}$)alkenyl group;
(c16) a ($C_2$-$C_{12}$)alkynyl group;
(c17) a ($C_3$-$C_{32}$)cycloalkyl group;
(c18) a halo($C_1$-$C_{12}$)alkyl group;
(c19) a halo($C_2$-$C_{12}$)alkenyl group;
(c20) a halo($C_2$-$C_{12}$)alkynyl group;
(c21) a halo($C_3$-$C_{12}$)cycloalkyl group;
(c22) a tri($C_1$-$C_{12}$)alkylsilyl group wherein the alkyl groups may be the same or different;
(c23) a tri($C_1$-$C_6$)alkylsilyl($C_1$-$C_6$)alkyl group wherein the alkyl groups of the tri($C_1$-$C_6$)alkylsilyl may be the same or different;
(c24) a ($C_3$-$C_{12}$)cycloalkyl($C_1$-$C_{12}$)alkyl group;
(c25) a halo($C_3$-$C_{12}$)cycloalkyl($C_1$-$C_{12}$)alkyl group;
(c26) a ($C_3$-$C_{12}$)cycloalkyl($C_3$-$C_{12}$)cycloalkyl;
(c27) a ($C_1$-$C_{12}$)alkoxy group;
(c28) a ($C_2$-$C_{12}$)alkenyloxy group;
(c29) a ($C_2$-$C_{12}$)alkynyloxy group;
(c30) a ($C_3$-$C_{12}$)cycloalkyloxy group (said cycloalkyl is optionally fused with a benzene ring);
(c31) a halo($C_1$-$C_{12}$)alkoxy group;
(c32) a halo($C_2$-$C_{12}$)alkenyloxy group;
(c33) a halo($C_2$-$C_{12}$)alkynyloxy group;
(c34) a halo($C_3$-$C_{12}$)cycloalkyloxy group (said cycloalkyl is optionally fused with a benzene ring);
(c35) a ($C_3$-$C_{12}$)cycloalkyl($C_1$-$C_{12}$)alkoxy group;
(c36) a halo($C_3$-$C_{12}$)cycloalkyl($C_1$-$C_{12}$)alkoxy group;
(c37) a ($C_1$-$C_6$)alkoxy($C_1$-$C_6$)alkyl group;
(c38) a halo($C_1$-$C_6$)alkoxy($C_1$-$C_6$)alkoxy group;
(c39) a ($C_1$-$C_6$)alkoxyhalo($C_1$-$C_6$)alkoxy group;
(c40) a halo($C_1$-$C_6$)alkoxyhalo($C_1$-$C_6$)alkoxy group;
(c41) a mercapto group;
(c42) a ($C_1$-$C_{12}$)alkylthio group;
(c43) a ($C_2$-$C_{12}$)alkenylthio group;
(c44) a ($C_2$-$C_{12}$)alkynylthio group;
(c45) a ($C_3$-$C_{12}$)cycloalkylthio group;
(c46) a halo($C_1$-$C_{12}$)alkylthio group;
(c47) a halo($C_2$-$C_{12}$)alkenylthio group;
(c48) a halo($C_2$-$C_{12}$)alkynylthio group;
(c49) a halo($C_3$-$C_{12}$)cycloalkylthio group;
(c50) a ($C_3$-$C_{12}$)cycloalkyl($C_1$-$C_{12}$)alkylthio group;
(c51) a halo($C_3$-$C_{12}$)cycloalkyl($C_1$-$C_{12}$)alkylthio group;
(c52) a ($C_1$-$C_6$)alkoxy($C_1$-$C_6$)alkylthio group;
(c53) a halo($C_1$-$C_6$)alkoxy($C_1$-$C_6$)alkylthio group;
(c54) a ($C_1$-$C_6$)alkoxyhalo($C_1$-$C_6$)alkylthio group;
(c55) a halo($C_1$-$C_6$)alkoxyhalo($C_1$-$C_6$)alkylthio group;
(c56) a ($C_1$-$C_{12}$)alkylsulfinyl group;
(c57) a ($C_2$-$C_{12}$)alkenylsulfinyl group;
(c58) a ($C_2$-$C_{12}$)alkynylsulfinyl group;
(c59) a ($C_3$-$C_{12}$)cycloalkylsulfinyl group;
(c60) a halo($C_1$-$C_{12}$)alkylsulfinyl group;
(c61) a halo($C_2$-$C_{12}$)alkenylsulfinyl group;
(c62) a halo($C_2$-$C_{12}$)alkynylsulfinyl group;
(c63) a halo($C_3$-$C_{12}$)cycloalkylsulfinyl group;
(c64) a ($C_3$-$C_{12}$)cycloalkyl($C_1$-$C_{12}$)alkylsulfinyl group;
(c65) a halo($C_3$-$C_{12}$)cycloalkyl($C_1$-$C_{12}$)alkylsulfinyl group;
(c66) a ($C_1$-$C_{12}$)alkylsulfonyl group;
(c67) a ($C_2$-$C_{12}$)alkenylsulfonyl group;
(c68) a ($C_2$-$C_{12}$)alkynylsulfonyl group;
(c69) a ($C_3$-$C_{12}$)cycloalkylsulfonyl group;
(c70) a halo($C_1$-$C_{12}$)alkylsulfonyl group;
(c71) a halo($C_2$-$C_{12}$)alkenylsulfonyl group;
(c72) a halo($C_2$-$C_{12}$)alkynylsulfonyl group;
(c73) a halo($C_3$-$C_{12}$)cycloalkylsulfonyl group;
(c74) a ($C_3$-$C_{12}$)cycloalkyl($C_1$-$C_{12}$)alkylsulfonyl group;
(c75) a halo($C_3$-$C_{12}$)cycloalkyl($C_1$-$C_{12}$)alkylsulfonyl group;
(c76) an aryl group;
(c77) an aryl group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)NOR^5$ group wherein $R^4$ and $R^5$ are as defined above;
(c78) an aryl($C_1$-$C_6$)alkyl group;
(c79) an aryl($C_1$-$C_6$)alkyl group having, on the ring, the same or different 1 to 5 substituents selected from (a) a halogen atom, (b) a cyano group, (c) a nitro group, (d) a ($C_1$-$C_6$)

alkyl group, (e) a halo($C_1$-$C_6$)alkyl group, (f) a ($C_1$-$C_6$) alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$) alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$) alkylthio group, (r) a ($C_1$-$C_6$)alkylsulfinyl group, (s) a halo ($C_1$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)NOR$^5$ group wherein $R^4$ and $R^5$ are as defined above;

(c80) an aryloxy group;

(c81) an aryloxy group having, on the ring, the same or different 1 to 5 substituents selected from (a) a halogen atom, (b) a cyano group, (c) a nitro group, (d) a ($C_1$-$C_6$) alkyl group, (e) a halo($C_1$-$C_6$)alkyl group, (f) a ($C_1$-$C_6$) alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$) alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$) alkylthio group, (r) a ($C_1$-$C_6$)alkylsulfinyl group, (s) a halo ($C_1$-$C_6$)alkylsulfinyl group, (t) a ($C_1$-$C_6$)alkylsulfonyl group, (u) a halo($C_1$-$C_6$)alkylsulfonyl group, (v) an N($R^4$) $R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)NOR$^5$ group wherein $R^4$ and $R^5$ are as defined above;

(c82) an aryloxy($C_1$-$C_6$)alkyl group;

(c83) an aryloxy($C_1$-$C_6$)alkyl group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$) alkynyloxy group, (l) a ($C_3$-$C_6$)cycloalkoxy group, (m) a halo($C_3$-$C_6$)cycloalkoxy group, (n) a ($C_3$-$C_6$)cycloalkyl ($C_1$-$C_6$)alkoxy group, (o) a halo($C_3$-$C_6$)cycloalkyl($C_1$-$C_6$) alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an N($R^4$) $R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)NOR$^5$ group wherein $R^4$ and $R^5$ are as defined above;

(c84) an arylthio group;

(c85) an arylthio group having, on the ring, the same or different 1 to 5 substituents selected from (a) a halogen atom, (b) a cyano group, (c) a nitro group, (d) a ($C_1$-$C_6$) alkyl group, (e) a halo($C_1$-$C_6$)alkyl group, (f) a ($C_1$-$C_6$) alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$) alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$) alkylthio group, (r) a ($C_2$-$C_6$)alkylsulfinyl group, (s) a halo ($C_2$-$C_6$)alkylsulfinyl group, (t) a ($C_1$-$C_6$)alkylsulfonyl group, (u) a halo($C_1$-$C_6$)alkylsulfonyl group, (v) an N($R^4$) $R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)NOR$^5$ group wherein $R^4$ and $R^5$ are as defined above;

(c86) a halo($C_1$-$C_6$)alkylenedioxy group;
(c87) a ($C_1$-$C_6$)alkoxy($C_1$-$C_6$)alkoxy group;
(c88) a ($C_3$-$C_8$)alkylene group;
(c89) a ($C_1$-$C_6$)alkyl($C_3$-$C_8$)alkylene group;
(c90) a tri($C_1$-$C_{12}$)alkylsilyloxy group wherein the alkyl groups may be the same or different;
(c91) a tri($C_1$-$C_{12}$)alkylsilyl($C_1$-$C_6$)alkoxy group wherein the alkyl groups may be the same or different;
(c92) a di($C_1$-$C_{12}$)alkylhalo($C_1$-$C_6$)alkylsilyl group wherein the alkyl groups may be the same or different;
(c93) a di($C_1$-$C_{12}$)alkyl($C_1$-$C_6$)alkylthio($C_1$-$C_6$)alkylsilyl group wherein the alkyl groups may be the same or different;
(c94) a di($C_1$-$C_{12}$)alkylhydroxysilyl group wherein the alkyl groups may be the same or different;
(c95) a di($C_1$-$C_{12}$)alkylhydrosilyl group wherein the alkyl groups may be the same or different;
(c96) a di($C_1$-$C_{12}$)alkylphenylsilyl group wherein the alkyl groups may be the same or different;
(c97) a ($C_1$-$C_6$)alkylthio($C_1$-$C_6$)alkoxy group;
(c98) a ($C_1$-$C_6$)alkylsulfinyl($C_1$-$C_6$)alkoxy group;
(c99) a ($C_1$-$C_6$)alkylsulfonyl($C_1$-$C_6$)alkoxy group;
(c100) a ($C_1$-$C_6$)alkoxycarbonyl($C_1$-$C_6$)alkoxy group;
(c101) a ($C_1$-$C_6$)alkylcarbonyl($C_1$-$C_6$)alkoxy group;
(c102) a cyano($C_1$-$C_6$)alkoxy group;
(c103) an aryl($C_1$-$C_6$)alkoxy group wherein the alkoxy moiety may be halogenated;
(c104) an aryl($C_1$-$C_6$)alkoxy group wherein the alkoxy moiety may be halogenated, which has, on the ring, the same or different 1 to 5 substituents selected from (a) a halogen atom, (b) a cyano group, (c) a nitro group, (d) a ($C_1$-$C_6$) alkyl group, (e) a halo($C_1$-$C_6$)alkyl group, (f) a ($C_1$-$C_6$) alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$) alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$) alkylthio group, (r) a ($C_2$-$C_6$)alkylsulfinyl group, (s) a halo ($C_2$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$$R^5$ group wherein $R^4$ and $R^5$ are as defined above, (y) an N($R^4$)SO$_2$$R^5$ group wherein $R^4$ and $R^5$ are as defined above, (z) a COR$^4$ group wherein $R^4$ is as defined above, (aa) a CO$_2$$R^4$ group wherein $R^4$ is as defined above, (bb) a CON($R^4$)$R^5$ group wherein $R^4$ and $R^5$ are as defined above, and (cc) a C($R^4$)NOR$^5$ group wherein $R^4$ and $R^5$ are as defined above;

(c105) a hydroxy($C_1$-$C_6$)alkyl group;

(c106) a ($C_1$-$C_6$)alkylthio($C_1$-$C_6$)alkylcarbonyl group;

(c107) a ($C_1$-$C_6$)alkylthio($C_1$-$C_6$)alkyl group;

(c108) a tri($C_1$-$C_{12}$)alkylsilyl($C_1$-$C_6$)alkylthio group wherein the alkyl groups of the tri($C_1$-$C_{12}$)alkylsilyl may be the same or different;

(c109) a tri($C_1$-$C_{12}$)alkylsilyl($C_1$-$C_6$)alkylsulfinyl group wherein the alkyl groups of the tri($C_1$-$C_{12}$)alkylsilyl may be the same or different;

(c110) a tri($C_1$-$C_{12}$)alkylsilyl($C_1$-$C_6$)alkylsulfonyl group wherein the alkyl groups of the tri($C_1$-$C_{12}$)alkylsilyl may be the same or different;

(c111) a $R^4$($R^5$)N($C_1$-$C_6$)alkyl group wherein $R^4$ and $R^5$ are as defined above;

(c112) a heterocyclic group;

(c113) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c114) a heterocyclyloxy group;

(c115) a heterocyclyloxy group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c116) a heterocyclylthio group;

(c117) a heterocyclylthio group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c118) a heterocyclylsulfinyl group;

(c119) a heterocyclylsulfinyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c120) a heterocyclylsulfonyl group;

(c121) a heterocyclylsulfonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c122) a heterocyclyl($C_1$-$C_6$)alkyloxy group;

(c123) a heterocyclylalkyloxy group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u)

a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c124) a ($C_1$-$C_{12}$)alkyl($C_3$-$C_{12}$)cycloalkyl group;
(c125) a halo($C_1$-$C_{12}$)alkyl($C_3$-$C_{12}$)cycloalkyl group;
(c126) a ($C_1$-$C_6$)alkylsulfinyl($C_1$-$C_6$)alkyl group;
(c127) a di($C_1$-$C_{12}$)alkylbenzylsilyl group wherein the alkyl groups may be the same or different;
(c128) a heterocyclyl($C_1$-$C_6$)alkyl group;
(c129) a heterocyclyl($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group,
(c130) a heterocyclyloxy($C_1$-$C_6$)alkyl group; or
(c131) a heterocyclyloxy($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group, or X can form, together with the adjacent $R^2$ or $R^3$, (C132) a bicyclo ring, wherein the bicyclo ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group; or, X can form, together with the adjacent X on an aromatic ring, (C133) a bicyclo ring or (C134) a fused ring, wherein the bicyclo ring or fused ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group, and m is an integer of 0 to 5,
or salts thereof;

[2] the benzyloxypyrimidine derivative of the above-mentioned [1], wherein m is as defined in the above-mentioned [1], $R^1$ is
(a1) a hydrogen atom;
(a2) a ($C_1$-$C_6$)alkyl group;
(a3) a ($C_3$-$C_7$)cycloalkyl group (said cycloalkyl group is optionally fused with a benzene ring);
(a4) a ($C_2$-$C_6$)alkenyl group;
(a5) a ($C_2$-$C_6$)alkynyl group;
(a6) a halo($C_1$-$C_6$)alkyl group;
(a8) a halo($C_2$-$C_6$)alkenyl group;
(a10) a ($C_1$-$C_6$)alkoxy($C_1$-$C_6$)alkyl group;
(a11) a ($C_3$-$C_6$)cycloalkyl($C_1$-$C_6$)alkyl group;
(a12) a ($C_1$-$C_6$)alkylthio($C_1$-$C_6$)alkyl group;
(a13) a ($C_1$-$C_6$)alkylsulfinyl($C_1$-$C_6$)alkyl group;
(a14) a ($C_1$-$C_6$)alkylsulfonyl($C_1$-$C_6$)alkyl group;
(a16) a halo($C_3$-$C_6$)cycloalkyl($C_1$-$C_6$)alkyl group;
(a22) an aryl($C_1$-$C_6$)alkyl group;
(a23) an aryl($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p)$_a$ ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined in the above-mentioned [1];
(a24) a cyano($C_1$-$C_6$)alkyl group;
(a30) an aryl group;
(a31) an aryl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$) alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, and (t) a phenoxy group;
(a32) an arylsulfonyl group;
(a33) an arylsulfonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;
(a34) an arylcarbonyl group;
(a35) an arylcarbonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)N$ carbonyl group wherein $R^4$ and $R^5$ are as defined above;

(a44) a $(C_1-C_6)$alkylcarbonyl group;

(a52) a heterocyclic group;

(a53) a heterocyclic group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, and (t) an oxo group;

(a54) a heterocyclyl$(C_1-C_6)$alkyl group;

(a55) a heterocyclyl$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, and (t) an oxo group;

(a56) a tri$(C_1-C_6)$alkylsilyl$(C_1-C_6)$alkyl group wherein the alkyl groups of the tri$(C_1-C_6)$alkylsilyl may be the same or different; or (a57) a $R^4(R^5)NCO$ group wherein $R^4$ and $R^5$ are as defined above, A is —O—, —S—, —SO— or —SO$_2$—, $R^2$ and $R^3$ may be the same or different and each is (b1) a hydrogen atom;

(b2) a $(C_1-C_6)$alkyl group;

(b3) a $(C_3-C_6)$cycloalkyl group;

(b6) a halo$(C_1-C_6)$alkyl group;

(b11) a $(C_1-C_6)$alkoxy$(C_1-C_6)$alkyl group;

(b12) a $(C_1-C_6)$alkylthio$(C_1-C_6)$alkyl group; or (b13) a $(C_1-C_6)$alkoxycarbonyl group, and X may be the same or different and each is (c1) a hydrogen atom;

(c2) a halogen atom;

(c5) a nitro group;

(c14) a $(C_1-C_{12})$alkyl group;

(c17) a $(C_3-C_{12})$cycloalkyl group;

(c18) a halo$(C_1-C_{12})$alkyl group;

(c21) a halo$(C_3-C_{12})$cycloalkyl group;

(c22) a tri$(C_1-C_{12})$alkylsilyl group wherein the alkyl groups may be the same or different;

(c27) a $(C_1-C_{12})$alkoxy group;

(c30) a $(C_3-C_{12})$cycloalkyloxy group (said cycloalkyl is optionally fused with a benzene ring);

(c31) a halo$(C_1-C_{12})$alkoxy group;

(c38) a halo$(C_1-C_6)$alkoxy$(C_1-C_6)$alkoxy group;

(c42) a $(C_1-C_{12})$alkylthio group;

(c46) a halo$(C_1-C_{12})$alkylthio group;

(c56) a $(C_1-C_{12})$alkylsulfinyl group;

(c66) a $(C_1-C_{12})$alkylsulfonyl group;

(c80) an aryloxy group;

(c81) an aryloxy group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)NOR^5$ group wherein $R^4$ and $R^5$ are as defined above;

(c112) a heterocyclic group;

(c113) a heterocyclic group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;

(c114) a heterocyclyloxy group;

(c115) a heterocyclyloxy group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;

(c130) a heterocyclyloxy$(C_1-C_6)$alkyl group; or (c131) a heterocyclyloxy($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$) alkyl group, (g) a ($C_1$-$C_6$)alkoxy group, (h) a halo($C_1$-$C_6$) alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)N$ carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group, or X can form, together with the adjacent $R^2$ or $R^3$, (C132) a bicyclo ring, wherein the bicyclo ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo ($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group; or, X can form, together with the adjacent X on an aromatic ring, (C133) a bicyclo ring or (C134) a fused ring, wherein the bicyclo ring or fused ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group, or salts thereof;

[3] an agrohorticultural insecticide comprising the benzyloxypyrimidine derivative according to the above-mentioned [1] or [2] or a salt thereof as an active ingredient;

[4] a method of using an agrohorticultural insecticide, which comprises treating a plant or soil with the active ingredient of the agrohorticultural insecticide according to the above-mentioned [3];

[5] use of the benzyloxypyrimidine derivative according to the above-mentioned [1] or [2] or a salt thereof as an agrohorticultural insecticide;

[6] a method of controlling an agrohorticultural pest, which comprises treating a plant or soil with an effective amount of the benzyloxypyrimidine derivative according to the above-mentioned [1] or [2] or a salt thereof;

[7] an ectoparasite controlling agent comprising the benzyloxypyrimidine derivative according to the above-mentioned [1] or [2] or a salt thereof as an active ingredient;

[8] a method of controlling an ectoparasite, which comprises treating the ectoparasite with an effective amount of the benzyloxypyrimidine derivative according to the above-mentioned [1] or [2] or a salt thereof;

and the like.

Effect of the Invention

The benzyloxypyrimidine derivative of the present invention or a salt thereof has a superior effect as an agrohorticultural insecticide. On the other hand, the derivative shows an effect on pests being parasitic in pet animals such as dogs and cats, and domestic animals such as cattle, sheep and the like.

DESCRIPTION OF EMBODIMENTS

In the definition of the benzyloxypyrimidine derivative of the present invention represented by the formula (I), the "halo" means a "halogen atom", and is a chlorine atom, a bromine atom, an iodine atom or a fluorine atom. The "($C_1$-$C_6$)alkyl group" is a straight chain or branched chain alkyl group having a carbon number of 1 to 6, for example, a methyl group, an ethyl group, a normal propyl group, an isopropyl group, a normal butyl group, an isobutyl group, a secondary butyl group, a tertiary butyl group, a normal pentyl group, an isopentyl group, a tertiary pentyl group, a neopentyl group, a 1,2-dimethylpropyl group, a 1-ethylpropyl group, a 1-methylbutyl group, a 2-methylbutyl group, a normal hexyl group, an isohexyl group, a 1,1,2-trimethylpropyl group and the like. The "($C_2$-$C_6$)alkenyl group" is a straight chain or branched chain alkenyl group having a carbon number of 2 to 6, for example, a vinyl group, an allyl group, an isopropenyl group, a 1-butenyl group, a 2-butenyl group, a 2-methyl-2-propenyl group, a 1-methyl-2-propenyl group, a 1,1-dimethyl-2-propenyl group, a 2-methyl-1-propenyl group, a pentenyl group, a 1-hexenyl group and the like. The "($C_2$-$C_6$)alkynyl group" is a straight chain or branched chain alkynyl group having a carbon number of 2 to 6, for example, an ethynyl group, a 1-propynyl group, a 2-propynyl group, a 1-methyl-2-propynyl group, a 1,1-dimethyl-2-propynyl group, a 1-butynyl group, a 2-butynyl group, a 3-butynyl group, a 3-methyl-1-propynyl group, a 2-methyl-3-propynyl group, a pentynyl group, a 1-hexynyl group and the like.

The "($C_1$-$C_{12}$)alkyl group" is a straight chain or branched chain alkyl group having a carbon number of 1 to 12, for example, a methyl group, an ethyl group, a normal propyl group, an isopropyl group, a normal butyl group, an isobutyl group, a secondary butyl group, a tertiary butyl group, a normal pentyl group, an isopentyl group, a tertiary pentyl group, a neopentyl group, a 2,3-dimethylpropyl group, a 1-ethylpropyl group, a 1-methylbutyl group, a normal hexyl group, an isohexyl group, a 1,1,2-trimethylpropyl group, a heptyl group, an octyl group, a nonyl group, a decyl group, an undecyl group, a dodecyl group and the like. The "($C_2$-$C_{12}$) alkenyl group" is a straight chain or branched chain alkenyl group having a carbon number of 2 to 12, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a heptenyl group, an octenyl group, a nonenyl group, a decenyl group, an undecenyl group, a dodecenyl group and the like. The "($C_2$-$C_{12}$)alkynyl group" is a straight chain or branched chain alkynyl group having a carbon number of 2 to 12, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a heptynyl group, an octynyl group, a nonynyl group, a decynyl group, an undecynyl group, a dodecynyl group and the like.

The "($C_3$-$C_6$)cycloalkyl group" is a cyclic alkyl group having a carbon number of 3 to 6 and is, for example, a cyclopropyl group, a cyclobutyl group, a cyclopentyl group, a cyclohexyl group and the like. The "($C_3$-$C_7$)cycloalkyl group (said cycloalkyl group is optionally fused with a benzene ring)" is a cyclic alkyl group having a carbon number of 3 to 7, such as a cyclopropyl group, a cyclobutyl group, a cyclopentyl group, a cyclohexyl group, a cycloheptyl and the like, or a group wherein said cyclic alkyl group is fused with a benzene ring (e.g., an indan-1-yl group, a 1,2,3,4-tetrahydronaphthalen-1-yl group etc.). Examples of the "$(C_1-C_6)$ alkoxy group" include a straight chain or branched chain alkoxy group having a carbon number of 1 to 6 such as a methoxy group, an ethoxy group, a normal propoxy group, an isopropoxy group, a normal butoxy group, a secondary butoxy group, a tertiary butoxy group, a normal pentyloxy group, an isopentyloxy group, a tertiary pentyloxy group, a neopentyloxy group, a 2,3-dimethylpropyloxy group, a 1-ethylpropyloxy group, a 1-methylbutyloxy group, a normal hexyloxy group, an isohexyloxy group, a 1,1,2-trimethylpropyloxy group and the like. Examples of the "$(C_2-C_6)$alkenyloxy group" include a straight chain or branched chain alkenyloxy group having a carbon number of 2 to 6 such as a propenyloxy group, a butenyloxy group, a pentenyloxy group and the like. Examples of the "$(C_2-C_6)$alkynyloxy group" include a straight chain or branched chain alkynyloxy group having a carbon number of 2 to 6 such as a propynyloxy group, a butynyloxy group, a pentynyloxy group and the like.

The "$(C_3-C_{12})$cycloalkyl group" is a cyclic alkyl group having a carbon number of 3 to 12, for example, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group and the like. Examples of the "$(C_1-C_{12})$ alkoxy group" include a straight chain or branched chain alkoxy group having a carbon number of 1 to 12 such as a methoxy group, an ethoxy group, a normal propoxy group, an isopropoxy group, a normal butoxy group, a secondary butoxy group, a tertiary butoxy group, a normal pentyloxy group, an isopentyloxy group, a tertiary pentyloxy group, a neopentyloxy group, a 2,3-dimethylpropyloxy group, a 1-ethylpropyloxy group, a 1-methylbutyloxy group, a normal hexyloxy group, an isohexyloxy group, a 1,1,2-trimethylpropyloxy group, a heptyloxy group, an octyloxy group, a nonyloxy group, a decyloxy group, an undecyloxy group, a dodecyloxy group and the like. Examples of the "$(C_2-C_{12})$ alkenyloxy group" include a straight chain or branched chain alkenyloxy group having a carbon number of 2 to 12 such as a propenyloxy group, a butenyloxy group, a pentenyloxy group, a hexenyloxy group, a heptenyloxy group, an octenyloxy group, a nonenyloxy group, a decenyloxy group, an undecenyloxy group, a dodecenyloxy group and the like. Examples of the "$(C_2-C_{12})$alkynyloxy group" m include a straight chain or branched chain alkynyloxy group having a carbon number of 2 to 12 such as a propynyloxy group, a butynyloxy group, a pentynyloxy group, a hexynyloxy group, a heptynyloxy group, an octynyloxy group, a nonynyloxy group, a decynyloxy group, an undecynyloxy group, a dodecynyloxy group and the like.

Examples of the "$(C_1-C_6)$alkylthio group" include a straight chain or branched chain alkylthio group having a carbon number of 1 to 6 such as a methylthio group, an ethylthio group, a normal propylthio group, an isopropylthio group, a normal butylthio group, a secondary butylthio group, a tertiary butylthio group, a normal pentylthio group, an isopentylthio group, a tertiary pentylthio group, a neopentylthio group, a 2,3-dimethylpropylthio group, a 1-ethylpropylthio group, a 1-methylbutylthio group, a normal hexylthio group, an isohexylthio group, a 1,1,2-trimethylpropylthio group and the like. Examples of the "$(C_1-C_6)$alkylsulfinyl group" include a straight chain or branched chain alkylsulfinyl group having a carbon number of 1 to 6 such as a methylsulfinyl group, an ethylsulfinyl group, a normal propylsulfinyl group, an isopropylsulfinyl group, a normal butylsulfinyl group, a secondary butylsulfinyl group, a tertiary butylsulfinyl group, a normal pentylsulfinyl group, an isopentylsulfinyl group, a tertiary pentylsulfinyl group, a neopentylsulfinyl group, a 2,3-dimethylpropylsulfinyl group, a 1-ethylpropylsulfinyl group, a 1-methylbutylsulfinyl group, a normal hexylsulfinyl group, an isohexylsulfinyl group, a 1,1,2-trimethylpropylsulfinyl group and the like. Examples of the "$(C_1-C_6)$alkylsulfonyl group" include a straight chain or branched chain alkylsulfonyl group having a carbon number of 1 to 6 such as a methylsulfonyl group, an ethylsulfonyl group, a normal propylsulfonyl group, an isopropylsulfonyl group, a normal butylsulfonyl group, a secondary butylsulfonyl group, a tertiary butylsulfonyl group, a normal pentylsulfonyl group, an isopentylsulfonyl group, a tertiary pentylsulfonyl group, a neopentylsulfonyl group, a 2,3-dimethylpropylsulfonyl group, a 1-ethylpropylsulfonyl group, a 1-methylbutylsulfonyl group, a normal hexylsulfonyl group, an isohexylsulfonyl group, a 1,1,2-trimethylpropylsulfonyl group and the like.

Examples of the "$(C_1-C_{12})$alkylthio group" include a straight chain or branched chain alkylthio group having a carbon number of 1 to 12 such as a methylthio group, an ethylthio group, a normal propylthio group, an isopropylthio group, a normal butylthio group, a secondary butylthio group, a tertiary butylthio group, a normal pentylthio group, an isopentylthio group, a tertiary pentylthio group, a neopentylthio group, a 2,3-dimethylpropylthio group, a 1-ethylpropylthio group, a 1-methylbutylthio group, a normal hexylthio group, an isohexylthio group, a 1,1,2-trimethylpropylthio group, a heptylthio group, an octylthio group, a nonylthio group, a decylthio group, an undecylthio group, a dodecylthio group and the like. Examples of the "$(C_1-C_{12})$alkylsulfinyl group" include a straight chain or branched chain alkylsulfinyl group having a carbon number of 1 to 12 such as a methylsulfinyl group, an ethylsulfinyl group, a normal propylsulfinyl group, an isopropylsulfinyl group, a normal butylsulfinyl group, a secondary butylsulfinyl group, a tertiary butylsulfinyl group, a normal pentylsulfinyl group, an isopentylsulfinyl group, a tertiary pentylsulfinyl group, a neopentylsulfinyl group, a 2,3-dimethylpropylsulfinyl group, a 1-ethylpropylsulfinyl group, a 1-methylbutylsulfinyl group, a normal hexylsulfinyl group, an isohexylsulfinyl group, a 1,1,2-trimethylpropylsulfinyl group, a heptylsulfinyl group, an octylsulfinyl group, a nonylsulfinyl group, a decylsulfinyl group, an undecylsulfinyl group, a dodecylsulfinyl group and the like. Examples of the "$(C_1-C_{12})$alkylsulfonyl group" include a straight chain or branched chain alkylsulfonyl group having a carbon number of 1 to 12 such as a methylsulfonyl group, an ethylsulfonyl group, a normal propylsulfonyl group, an isopropylsulfonyl group, a normal butylsulfonyl group, a secondary butylsulfonyl group, a tertiary butylsulfonyl group, a normal pentylsulfonyl group, an isopentylsulfonyl group, a tertiary pentylsulfonyl group, a neopentylsulfonyl group, a 2,3-dimethylpropylsulfonyl group, a 1-ethylpropylsulfonyl group, a 1-methylbutylsulfonyl group, a normal hexylsulfonyl group, an isohexylsulfonyl group, a 1,1,2-trimethylpropylsulfonyl group, a heptylsulfonyl group, an octylsulfonyl group, a nonylsulfonyl group, a decylsulfonyl group, an undecylsulfonyl group, a dodecylsulfonyl group and the like.

Examples of the "$(C_2-C_{12})$alkenylthio group" include a straight chain or branched chain alkenylthio group having a carbon number of 2 to 12 such as a propenylthio group, a butenylthio group, a pentenylthio group, a hexenylthio group, a heptenylthio group, an octenylthio group, a nonenylthio group, a decenylthio group, an undecenylthio group, a dodecenylthio group and the like. Examples of the "$(C_2-C_{12})$alkynylthio group" include a straight chain or branched chain alkynylthio group having a carbon number of 2 to 12 such as a propynylthio group, a butynylthio group, a pentynylthio group, a hexynylthio group, a heptynylthio group, an octynylthio group, a nonynylthio group, a decynylthio group, an undecynylthio group, a dodecynylthio group and the like.

Examples of the "$(C_2\text{-}C_{12})$alkenylsulfinyl group" include a straight chain or branched chain alkenylsulfinyl group having a carbon number of 2 to 12 such as a propenylsulfinyl group, a butenylsulfinyl group, a pentenylsulfinyl group, a hexenylsulfinyl group, a heptenylsulfinyl group, an octenylsulfinyl group, a nonenylsulfinyl group, a decenylsulfinyl group, an undecenylsulfinyl group, a dodecenylsulfinyl group and the like. Examples of the "$(C_2\text{-}C_{12})$alkynylsulfinyl group" include a straight chain or branched chain alkynylsulfinyl group having a carbon number of 2 to 12 such as a propynylsulfinyl group, a butynylsulfinyl group, a pentynylsulfinyl group, a hexynylsulfinyl group, a heptynylsulfinyl group, an octynylsulfinyl group, a nonynylsulfinyl group, a decynylsulfinyl group, an undecynylsulfinyl group, a dodecynylsulfinyl group and the like.

Examples of the "$(C_2\text{-}C_{12})$alkenylsulfonyl group" include a straight chain or branched chain alkenylsulfonyl group having a carbon number of 2 to 12 such as a propenylsulfonyl group, a butenylsulfonyl group, a pentenylsulfonyl group, a hexenylsulfonyl group, a heptenylsulfonyl group, an octenylsulfonyl group, a nonenylsulfonyl group, a decenylsulfonyl group, an undecenylsulfonyl group, a dodecenylsulfonyl group and the like. Examples of the "$(C_2\text{-}C_{12})$alkynylsulfonyl group" include a straight chain or branched chain alkynylsulfonyl group having a carbon number of 2 to 12 such as a propynylsulfonyl group, a butynylsulfonyl group, a pentynylsulfonyl group, a hexynylsulfonyl group, a heptynylsulfonyl group, an octynylsulfonyl group, a nonynylsulfonyl group, a decynylsulfonyl group, an undecynylsulfonyl group, a dodecynylsulfonyl group and the like.

Examples of the "$(C_3\text{-}C_6)$cycloalkoxy group" include a cyclic alkoxy having a carbon number of 3 to 6 such as a cyclopropoxy group, a cyclobutoxy a group, a cyclopentyloxy group, a cyclohexyloxy group and the like. Examples of the "$(C_3\text{-}C_{12})$cycloalkyloxy group wherein the cycloalkyl may be fused with a benzene ring" include a cyclic alkoxy having a carbon number of 3 to 12 such as a cyclopropoxy group, a cyclobutoxy a group, a cyclopentyloxy group, a cyclohexyloxy group, a cycloheptyloxy group, a cyclooctyloxy group, a cyclononyloxy group, a cyclodecyloxy group, a cycloundecyloxy group, a cyclododecyloxy group and the like or a group wherein the cyclic alkoxy group is fused with a benzene ring (e.g., indan-1-yloxy group, 1,2,3,4-tetrahydronaphthalen-1-yloxy group etc.). Examples of the "$(C_3\text{-}C_{12})$cycloalkylthio group" include a cyclic alkylthio group having a carbon number of 3 to 12 such as a cyclopropylthio group, a cyclobutylthio group, a cyclopentylthio group, a cyclohexylthio group, a cycloheptylthio group, a cyclooctylthio group, a cyclononylthio group, a cyclodecylthio group, a cycloundecylthio group, a cyclododecylthio group and the like. Examples of the "$(C_3\text{-}C_{12})$cycloalkylsulfinyl group" include a cyclic alkylsulfinyl group having a carbon number of 3 to 12 such as a cyclopropylsulfinyl group, a cyclobutylsulfinyl group, a cyclopentylsulfinyl group, a cyclohexylsulfinyl group, a cycloheptylsulfinyl group, a cyclooctylsulfinyl group, a cyclononylsulfinyl group, a cyclodecylsulfinyl group, a cycloundecylsulfinyl group, a cyclododecylsulfinyl group and the like. Examples of the "$(C_3\text{-}C_{12})$cycloalkylsulfonyl group" include a cyclic alkylsulfonyl group having a carbon number of 3 to 12 such as a cyclopropylsulfonyl group, a cyclobutylsulfonyl group, a cyclopentylsulfonyl group, a cyclohexylsulfonyl group, a cycloheptylsulfonyl group, a cyclooctylsulfonyl group, a cyclononylsulfonyl group, a cyclodecylsulfonyl group, a cycloundecylsulfonyl group, a cyclododecylsulfonyl group and the like.

In the above-mentioned "$(C_1\text{-}C_6)$alkyl group", "$(C_2\text{-}C_6)$alkenyl group", "$(C_2\text{-}C_6)$alkynyl group", "$(C_3\text{-}C_6)$cycloalkyl group", "$(C_3\text{-}C_6)$cycloalkoxy group", "$(C_3\text{-}C_{12})$cycloalkyloxy group wherein the cycloalkyl may be fused with a benzene ring", "$(C_1\text{-}C_6)$alkoxy group", "$(C_2\text{-}C_6)$alkenyloxy group", "$(C_2\text{-}C_6)$alkynyloxy group", "$(C_1\text{-}C_6)$alkylthio group", "$(C_1\text{-}C_6)$alkylsulfinyl group", "$(C_1\text{-}C_6)$alkylsulfonyl group", "$(C_2\text{-}C_{12})$alkenylthio group", "$(C_2\text{-}C_{12})$alkynylthio group", "$(C_2\text{-}C_{12})$alkenylsulfinyl group", "$(C_2\text{-}C_{12})$alkynylsulfinyl group", "$(C_2\text{-}C_{12})$alkenylsulfonyl group", "$(C_2\text{-}C_{12})$alkynylsulfonyl group", "$(C_1\text{-}C_{12})$alkyl group", "$(C_2\text{-}C_{12})$alkenyl group", "$(C_2\text{-}C_{12})$alkynyl group", "$(C_3\text{-}C_{12})$cycloalkyl group", "$(C_1\text{-}C_{12})$alkoxy group", "$(C_2\text{-}C_{12})$alkenyloxy group", "$(C_2\text{-}C_{12})$alkynyloxy group", "$(C_1\text{-}C_{12})$alkylthio group", "$(C_3\text{-}C_{12})$cycloalkylthio group", "$(C_1\text{-}C_{12})$alkylsulfinyl group", "$(C_3\text{-}C_{12})$cycloalkylsulfinyl group", "$(C_1\text{-}C_{12})$alkylsulfonyl group" and "$(C_3\text{-}C_{12})$cycloalkylsulfonyl group", one or more halogen atoms may be substituted at substitutable position(s) and, when the number of the substituted halogen atoms are two or more, they may be the same or different. They show "halo$(C_1\text{-}C_6)$alkyl group", "halo$(C_2\text{-}C_6)$alkenyl group", "halo$(C_2\text{-}C_6)$alkynyl group", "halo$(C_3\text{-}C_6)$cycloalkyl group", "halo$(C_3\text{-}C_6)$cycloalkoxy group", "halo$(C_3\text{-}C_{12})$cycloalkyloxy group wherein the cycloalkyl may be fused with a benzene ring", "halo$(C_1\text{-}C_6)$alkoxy group", "halo$(C_2\text{-}C_6)$alkenyloxy group", "halo$(C_2\text{-}C_6)$alkynyloxy group", "halo$(C_1\text{-}C_6)$alkylthio group", "halo$(C_1\text{-}C_6)$alkylsulfinyl group", "halo$(C_1\text{-}C_6)$alkylsulfonyl group", "halo$(C_2\text{-}C_{12})$alkenylthio group", "halo$(C_2\text{-}C_{12})$alkynylthio group", "halo$(C_2\text{-}C_{12})$alkenylsulfinyl group", "halo$(C_{2\text{-}112})$alkynylsulfinyl group", "halo$(C_2\text{-}C_{12})$alkenylsulfonyl group", "halo$(C_2\text{-}C_{12})$alkynylsulfonyl group", "halo$(C_1\text{-}C_{12})$alkyl group", "halo$(C_2\text{-}C_{12})$alkenyl group", "halo$(C_2\text{-}C_{12})$alkynyl group", "halo$(C_3\text{-}C_{12})$cycloalkyl group", "halo$(C_1\text{-}C_{12})$alkoxy group", "halo$(C_{2\text{-}112})$alkenyloxy group", "halo$(C_2\text{-}C_{12})$alkynyloxy group", "halo$(C_1\text{-}C_{12})$alkylthio group", "halo$(C_3\text{-}C_{12})$cycloalkylthio group", "halo$(C_1\text{-}C_{12})$alkylsulfinyl group", "halo$(C_3\text{-}C_{12})$cycloalkylsulfinyl group", "halo$(C_1\text{-}C_{12})$alkylsulfonyl group" and "halo$(C_3\text{-}C_{12})$cycloalkylsulfonyl group", respectively.

Examples of the "tri$(C_1\text{-}C_6)$alkylsilyl group" and "tri$(C_1\text{-}C_{12})$alkylsilyl group" include a straight chain or branched chain trialkylsilyl group having a carbon number of 1 to 6 or 1 to 12 such as a trimethylsilyl group, a triethylsilyl group, a tertiary-butyldimethylsilyl group, an ethyldimethylsilyl group, an isopropyldimethylsilyl group, an n-propyldimethylsilyl group, and the like. In this case, three alkyl groups may be the same or different.

Examples of the di$(C_1\text{-}C_{12})$alkylhalo$(C_1\text{-}C_6)$alkylsilyl group include a chloromethyldimethylsilyl group and the like. In this case, the two alkyl groups may be the same or different.

Examples of the di$(C_1\text{-}C_{12})$alkyl$(C_1\text{-}C_6)$alkylthio$(C_1\text{-}C_6)$alkylsilyl group include a methylthiomethyldimethylsilyl group and the like. In this case, the two alkyl groups may be the same or different.

Examples of the di$(C_1\text{-}C_{12})$alkylhydrosilyl group include a diisopropylsilyl group and the like. In this case, the two alkyl groups may be the same or different.

Examples of the di$(C_1\text{-}C_{12})$alkylhydroxysilyl group include a dimethylhydroxysilyl group and the like. In this case, the two alkyl groups may be the same or different.

Examples of the di($C_1$-$C_{12}$)alkylphenylsilyl group include a dimethyl(phenyl)silyl group and the like. In this case, the two alkyl groups may be the same or different.

Examples of the di($C_1$-$C_{12}$)alkylbenzylsilyl group include a dimethyl(benzyl)silyl group and the like. In this case, the two alkyl groups may be the same or different.

Examples of the "aryl group" include an aromatic hydrocarbon group having a carbon number of 6 to 10 such as a phenyl group, a 1-naphthyl group, a 2-naphthyl group and the like.

The expressions of "($C_1$-$C_{12}$)", "($C_2$-$C_{12}$)", "($C_3$-$C_{12}$)" and the like show ranges of the carbon atom numbers of various substituents. Furthermore, the above-mentioned definition applies to the groups wherein the above-mentioned substituents are bonded to each other. For example, "($C_1$-$C_6$)alkoxy($C_1$-$C_6$)alkyl group" means that a straight chain or branched chain alkoxy group having a carbon number of 1 to 6 is bonded to a straight chain or branched chain alkyl group having a carbon number of 1 to 6.

The "($C_3$-$C_8$)alkylene group", "($C_1$-$C_6$)alkyl($C_3$-$C_8$)alkylene group" and "halo($C_1$-$C_6$)alkylenedioxy group" are groups that can is be formed together with the two adjacent X groups, and examples of the "($C_3$-$C_8$)alkylene group" and "($C_1$-$C_6$)alkyl($C_3$-$C_8$)alkylene group" include a propylene group, a butylene group, a pentylene group, a hexylene group, and a 1,1,4,4-tetramethylbutylene group and the like, and examples of the "halo($C_1$-$C_6$)alkylenedioxy group" include a difluoromethylenedioxy group, a tetrafluoroethylenedioxy group and the like.

Examples of the bicyclo ring formed by X together with the adjacent $R^2$ or $R^3$ include bicyclo rings such as 1,2,3,4-tetrahydronaphthalene, inden, indane, 1,2,3,4-tetrahydro-1,4-methanonaphthalene, 1,2,3,4-tetrahydro-1,4-ethanonaphthalene and the like. In addition, examples of the fused ring formed by two X groups include fused rings such as 2,3-dihydrobenzofuran, 2,3-dihydrobenzothiophene and the like. Examples of the bicyclo ring formed by two adjacent X groups on the aromatic ring include bicyclo rings such as 1,2,3,4-tetrahydronaphthalene, inden, indane, 1,2,3,4-tetrahydro-1,4-methanonaphthalene, 1,2,3,4-tetrahydro-1,4-ethanonaphthalene and the like.

Examples of the "heterocyclic group" and "heterocycle" include a 5- or 6-membered monocyclic aromatic heterocyclic group or 3- to 6-membered monocyclic nonaromatic heterocyclic group each of which contains, as a ring-constituting atom besides carbon atom, 1 to 4 hetero atoms selected from an oxygen atom, a sulfur atom and a nitrogen atom, a fused heterocyclic group obtained by condensation of the monocyclic aromatic or nonaromatic heterocycle with a benzene ring, and a fused heterocyclic group obtained by condensation of the monocyclic aromatic or nonaromatic heterocycles (heterocycles may be different).

Examples of the "aromatic heterocyclic group" include monocyclic aromatic heterocyclic groups such as furanyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, triazinyl and the like; aromatic fused heterocyclic groups such as quinolyl, isoquinolyl, quinazolyl, quinoxalyl, benzofuranyl, benzothienyl, benzoxazolyl, benzoisoxazolyl, benzothiazolyl, benzimidazolyl, benzotriazolyl, indolyl, indazolyl, pyrrolopyrazinyl, imidazopyridinyl, imidazopyrazinyl, pyrazolopyridinyl, pyrazolothienyl, pyrazolotriazinyl and the like.

Examples of the "nonaromatic heterocyclic group" include monocyclic nonaromatic heterocyclic groups such as oxiranyl, thiiranyl, aziridinyl, oxetanyl, thietanyl, azetidinyl, pyrrolidinyl, piperidinyl, morpholinyl, thiomorpholinyl, piperazinyl, hexamethyleniminyl, oxazolidinyl, thiazolidinyl, imidazolidinyl, oxazolinyl, thiazolinyl, imidazolinyl, dioxolyl, dioxolanyl, dihydrooxadiazolyl, 2-oxo-1,3-oxazolidin-5-yl, pyranyl, tetrahydropyranyl, thiopyranyl, tetrahydrothiopyranyl, 1-oxidotetrahydrothiopyranyl, 1,1-dioxidotetrahydrothiopyranyl, tetrahydrofuranyl, dioxanyl, pyrazolidinyl, pyrazolinyl, tetrahydropyrimidinyl, dihydrotriazolyl, tetrahydrotriazolyl and the like; nonaromatic fused heterocyclic groups such as dihydroindolyl, dihydroisoindolyl, dihydrobenzofuranyl, dihydrobenzodioxinyl, dihydrobenzodioxepinyl, tetrahydrobenzofuranyl, chromenyl, dihydroquinolinyl, tetrahydroquinolinyl, dihydroisoquinolinyl, tetrahydroisoquinolinyl, dihydrophthalazinyl and the like; and the like.

Preferable examples of the "heterocyclic group" include isoquinolinyl, tetrazolyl, quinolinyl, furanyl, tetrahydrofuranyl, isoxazolyl, pyrimidinyl, pyrazinyl, pyridyl, pyrazolyl, benzimidazolyl, 2,3-dioxaisoindolyl, tetrahydrofuranyl, oxiranyl, thienyl, pyridazinyl and the like.

Examples of the salts of the benzyloxypyrimidine derivative represented by the formula (I) of the present invention include inorganic acid salts such as hydrochloride, sulfate, nitrate salt, phosphate and the like, organic acid salts such as acetate, fumarate, maleate, oxalate, methanesulfonate, benzenesulfonate, paratoluenesulfonate and the like, and salts with inorganic or organic bases such as sodium ion, potassium ion, calcium ion, trimethylammonium and the like.

The benzyloxypyrimidine derivative represented by the formula (I) and a salt thereof of the present invention may contain one or plural number of asymmetric centers in the structural formula, and in some cases, two or more optical isomers and diastereomers may be present. The present invention encompasses any of such optical isomers and mixtures containing them at any ratio. In addition, the benzyloxypyrimidine derivative represented by the formula (I) and a salt thereof of the present invention may have two types of geometric isomers derived from a C—C double bond in the structural formula. The present invention encompasses all of geometric isomers and the mixtures containing them at any ratio.

Preferred as $R^1$ is
(a1) a hydrogen atom;
(a2) a ($C_1$-$C_6$)alkyl group;
(a3) a ($C_3$-$C_7$)cycloalkyl group (said cycloalkyl group is optionally fused with a benzene ring);
(a4) a ($C_2$-$C_6$)alkenyl group;
(a5) a ($C_2$-$C_6$)alkynyl group;
(a6) a halo($C_1$-$C_6$)alkyl group;
(a8) a halo($C_2$-$C_6$)alkenyl group;
(a10) a ($C_1$-$C_6$)alkoxy($C_1$-$C_6$)alkyl group;
(a11) a ($C_3$-$C_6$)cycloalkyl($C_1$-$C_6$)alkyl group;
(a12) a ($C_1$-$C_6$)alkylthio($C_1$-$C_6$)alkyl group;
(a13) a ($C_1$-$C_6$)alkylsulfinyl($C_1$-$C_6$)alkyl group;
(a14) a ($C_1$-$C_6$)alkylsulfonyl($C_1$-$C_6$)alkyl group;
(a16) a halo($C_3$-$C_6$)cycloalkyl($C_1$-$C_6$)alkyl group;
(a22) an aryl($C_1$-$C_6$)alkyl group;
(a23) an aryl($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a $(C_1-C_6)$alkoxycarbonyl group, and (s) a $R^4(R^5)N$ carbonyl group wherein $R^4$ and $R^5$ are as defined in the above-mentioned [1];
(a24) a cyano$(C_1-C_6)$alkyl group;
(a30) an aryl group;
(a31) an aryl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, and (t) a phenoxy group;
(a32) an arylsulfonyl group;
(a33) an arylsulfonyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo $(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)N$ carbonyl group wherein $R^4$ and $R^5$ are as defined above;
(a34) an arylcarbonyl group;
(a35) an arylcarbonyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo $(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)N$ carbonyl group wherein $R^4$ and $R^5$ are as defined above;
(a44) a $(C_1-C_6)$alkylcarbonyl group;
(a52) a heterocyclic group;
(a53) a heterocyclic group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo $(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, and (t) an oxo group;
(a54) a heterocyclyl$(C_1-C_6)$alkyl group;
(a55) a heterocyclyl$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$ alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, and (t) an oxo group;
(a56) a tri$(C_1-C_6)$alkylsilyl$(C_1-C_6)$alkyl group wherein the alkyl groups of the tri$(C_1-C_6)$alkylsilyl may be the same or different; or
(a57) a $R^4(R^5)NCO$ group wherein $R^4$ and $R^5$ are as defined above.

Preferred as A is —O—, —S—, —SO— or —$SO_2$—, more preferably —O— or —S—, further preferably —O—.

$R^2$ and $R^3$ may be the same or different and each is preferably
(b1) a hydrogen atom;
(b2) a $(C_1-C_6)$alkyl group;
(b3) a $(C_3-C_6)$cycloalkyl group;
(b6) a halo$(C_1-C_6)$alkyl group;
(b11) a $(C_1-C_6)$alkoxy$(C_1-C_6)$alkyl group;
(b12) a $(C_1-C_6)$alkylthio$(C_1-C_6)$alkyl group; or
(b13) a $(C_1-C_6)$alkoxycarbonyl group.

X may be the same or different and each is preferably
(c1) a hydrogen atom;
(c2) a halogen atom;
(c5) a nitro group;
(c14) a $(C_1-C_{12})$alkyl group;
(c17) a $(C_3-C_{12})$cycloalkyl group;
(c18) a halo$(C_1-C_{12})$alkyl group;
(c21) a halo$(C_3-C_{12})$cycloalkyl group;
(c22) a tri$(C_1-C_{12})$alkylsilyl group wherein the alkyl groups may be the same or different;
(c27) a $(C_1-C_{12})$alkoxy group;
(c30) a $(C_3-C_{12})$cycloalkyloxy group (said cycloalkyl is optionally fused with a benzene ring);
(c31) a halo$(C_1-C_{12})$alkoxy group;
(c38) a halo$(C_1-C_6)$alkoxy$(C_1-C_6)$alkoxy group;
(c42) a $(C_1-C_{12})$alkylthio group;
(c46) a halo$(C_1-C_{12})$alkylthio group;
(c56) a $(C_1-C_{12})$alkylsulfinyl group;
(c66) a $(C_1-C_{12})$alkylsulfonyl group;
(c80) an aryloxy group;
(c81) an aryloxy group having, on the ring, the same or different 1 to 5 substituents selected from (a) a halogen atom, (b) a cyano group, (c) a nitro group, (d) a $(C_1-C_6)$ alkyl group, (e) a halo$(C_1-C_6)$alkyl group, (f) a $(C_1-C_6)$ alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$ alkoxy group, (o) a halo$(C_3-C_6)$cycloalkyl$(C_1-C_6)$alkoxy group, (p) a $(C_1-C_6)$alkylthio group, (q) a halo$(C_1-C_6)$ alkylthio group, (r) a $(C_1-C_6)$alkylsulfinyl group, (s) a halo $(C_1-C_6)$alkylsulfinyl group, (t) a $(C_1-C_6)$alkylsulfonyl group, (u) a halo$(C_1-C_6)$alkylsulfonyl group, (v) an $N(R^4)$ $R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)NOR^5$ group wherein $R^4$ and $R^5$ are as defined above;

(c112) a heterocyclic group;
(c113) a heterocyclic group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;
(c114) a heterocyclyloxy group;
(c115) a heterocyclyloxy group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_5)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;
(c130) a heterocyclyloxy$(C_1-C_6)$alkyl group; or
(c131) a heterocyclyloxy$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group, or preferably X can form, together with the adjacent $R^2$ or $R^3$, (C132) a bicyclo ring, wherein the bicyclo ring optionally has the same or different, one or more substituents selected from (a) a halogen atom, (b) a $(C_1-C_6)$alkyl group, (c) a halo$(C_1-C_6)$alkyl group, (d) a $(C_1-C_6)$alkoxy group, (e) a halo$(C_1-C_6)$alkoxy group, (f) a $(C_1-C_6)$alkylthio group, (g) a halo$(C_1-C_6)$alkylthio group, (h) a $(C_1-C_6)$alkylsulfinyl group, (i) a halo$(C_1-C_6)$alkylsulfinyl group, (j) a $(C_1-C_6)$alkylsulfonyl group, and (k) a halo$(C_1-C_6)$alkylsulfonyl group; or X can form, together with the adjacent X on the aromatic ring, (C133) a bicyclo ring or (C134) a fused ring, wherein the bicyclo ring or fused ring optionally has the same or different one or more substituents selected from (a) a halogen atom, (b) a $(C_1-C_6)$alkyl group, (c) a halo$(C_1-C_6)$alkyl group, (d) a $(C_1-C_6)$alkoxy group, (e) a halo$(C_1-C_6)$alkoxy group, (f) a $(C_1-C_6)$alkylthio group, (g) a halo$(C_1-C_6)$alkylthio group, (h) a $(C_1-C_6)$alkylsulfinyl group, (i) a halo$(C_1-C_6)$alkylsulfinyl group, (j) a $(C_1-C_6)$alkylsulfonyl group, and (k) a halo$(C_1-C_6)$alkylsulfonyl group.

Preferred as m is 1, 2 or 3, more preferably 1.

Representative production methods of the benzyloxypyrimidine derivative represented by the formula (I) of the present invention are shown in the following, to which the present invention is not limited.

Production Method 1.

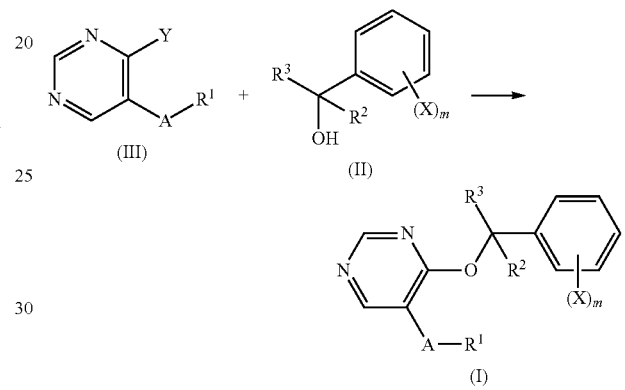

wherein $R^1$, $R^2$, $R^3$, A, X and m are defined above, and Y is a leaving group such as a chlorine atom, a bromine atom, an iodine atom and the like.

A pyrimidine compound represented by the formula (III) and a compound represented by the formula (II) are reacted in the presence of a base in an inert solvent to give the benzyloxypyrimidine derivative of the present invention represented by the formula (I).

The compound represented by the formula (III) can be produced according to the method described in Journal of the Chemical Society (1960), 4590, or JP-A-49-92080. In addition, as the starting compound represented by the formula (II), a product on the market may be directly used. Alternatively, the compound can be produced according to the method described in a known document (e.g., 4th Edition Jikken Kagaku Kouza 24, The Chemical Society of Japan ed.) or a method analogous thereto.

From Formula (III) to Formula (I)

A pyrimidine compound represented by the formula (III) and a compound represented by the formula (II) are reacted in the presence of a base in an inert solvent to give a pyrimidine derivative represented by the formula (I).

Examples of the base usable for this reaction include inorganic bases such as sodium hydroxide, potassium hydroxide, sodium carbonate, potassium carbonate, cesium carbonate, sodium hydrogen carbonate, potassium hydrogen carbonate and the like, alkali metal hydrides such as sodium hydride, potassium hydride and the like, alkoxides such as sodium methoxide, sodium ethoxide, potassium tertiary butoxide and the like.

The amount of the base to be used is generally about 1.0- to 5-fold mol relative to a compound represented by the formula (II).

The inert solvent usable in the present reaction may be any as long as it does not markedly inhibit this reaction and, for example, alcohols such as methanol, ethanol, propanol, butanol, 2-propanol and the like; chain or cyclic ethers such as diethyl ether, tetrahydrofuran, dioxane and the like; aromatic hydrocarbons such as benzene, toluene, xylene and the like; halogenated hydrocarbons such as methylene chloride, chloroform, carbon tetrachloride and the like, halogenated aromatic hydrocarbons such as chlorobenzene, dichlorobenzene and the like; nitriles such as acetonitrile and the like; esters such as ethyl acetate and the like; polar solvents such as N,N-dimethylformamide, N,N-dimethylacetamide, dimethyl sulfoxide, 1,3-dimethyl-2-imidazolinone and the like can be mentioned. These inert solvents may be used alone or in a mixture of two or more kinds thereof.

The reaction temperature in this reaction may be generally from about 20° C. to the boiling point of the solvent to be used. While the reaction time varies depending on the reaction scale, reaction temperature and the like, it can be appropriately selected from the range of several min to 48 hrs.

A compound represented by the formula (II) is used within the range of generally about 1.0- to 5-fold mol relative to a pyrimidine compound represented by the formula (III).

This reaction is also preferably performed in, for example, an inert gas such as a nitrogen gas and an argon gas.

After completion of the reaction, the objective substance may be isolated from the reaction system containing the objective substance by a conventional method and the objective substance can be produced by purification using recrystallization or column chromatography, etc., if necessary.

Typical examples of the derivative represented by the formula (I) of the present invention are shown in Table 1, Table 2, Table 3, Table 4 and Table 5, to which the present invention is not limited.

In the Tables, "Me" is a methyl group, "Et" is an ethyl group, "Pr" is a propyl group, "Bu" is a butyl group, "Pen" is a pentyl group, "Hex" is a hexyl group, "Hep" is a heptyl group, "Ph" is a phenyl group, "TMS" is a trimethylsilyl group, "THF" is a tetrahydrofuranyl group, "Py" is a pyridyl group, "furanyl" is a furanyl group, "n-" is normal, "i-" is iso, "s-" is secondary, "neo-" is neo, "t-" is tertiary, and "c-" is an alicyclic hydrocarbon group. The "Z" and "E" show configuration of geometric isomer. The "substitution position" means the position of substitution in each structural formula, and the property shows a melting point (° C.) or a refractive index $n_D$ (measurement temperature; ° C.).

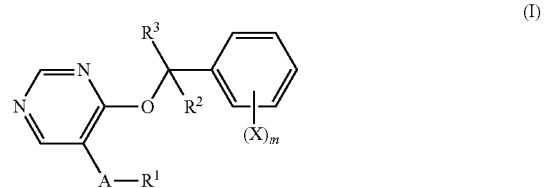

(I)

TABLE 1

| compound No. | AR¹ | R² | R³ | (X)$_m$ | property value |
|---|---|---|---|---|---|
| 1-1 | OMe | H | H | 4-t-Bu | 58-59 |
| 1-2 | OEt | H | H | 4-t-Bu | 1.5368(22.5) |
| 1-3 | O—n-Pr | H | H | 4-t-Bu | 1.5369(25.0) |
| 1-4 | O—i-Pr | H | H | 4-t-Bu | 59-60 |
| 1-5 | O—i-Bu | H | H | 4-t-Bu | 1.5252(24.5) |
| 1-6 | O—c-Pen | H | H | 4-t-Bu | 1.5392(21.5) |
| 1-7 | OCH₂OMe | H | H | 4-t-Bu | 54-55 |
| 1-8 | OCH₂SMe | H | H | 4-t-Bu | 1.5666(22.0) |
| 1-9 | OCH₂—c-Pr | H | H | 4-t-Bu | 1.5440(19.5) |
| 1-10 | OCH₂CH₂Cl | H | H | 4-t-Bu | 1.5490(23.0) |
| 1-11 | OCH₂CCl=CH₂ | H | H | 4-t-Bu | |
| 1-12 | OCH₂CH=CHCl(Z) | H | H | 4-t-Bu | |
| 1-13 | OCH₂CCl=CHCl(E) | H | H | 4-t-Bu | |
| 1-14 | OPh | H | H | 4-t-Bu | 1.5710(24.6) |
| 1-15 | OMe | Me | H | 4-t-Bu | 60-61 |
| 1-16 | OPh | Me | H | 4-t-Bu | 1.5661(19.6) |
| 1-17 | OMe | Et | H | 4-t-Bu | |
| 1-18 | OMe | i-Pr | H | 4-t-Bu | 130-132 |
| 1-19 | OMe | c-Pr | H | 4-t-Bu | |
| 1-20 | OMe | Me | Me | 4-t-Bu | 64-65 |
| 1-21 | OMe | H | H | 4-i-Pr | 1.5548(22.0) |
| 1-22 | OEt | H | H | 4-i-Pr | |
| 1-23 | O—n-Pr | H | H | 4-i-Pr | 1.5388(23.0) |
| 1-24 | O—i-Pr | H | H | 4-i-Pr | |
| 1-25 | O—c-Pen | H | H | 4-i-Pr | |
| 1-26 | OCH₂—c-Pr | H | H | 4-i-Pr | 1.547(26.5) |
| 1-27 | OCH₂CH₂Cl | H | H | 4-i-Pr | |
| 1-28 | OCH₂CCl=CH₂ | H | H | 4-i-Pr | 1.5540(22.5) |
| 1-29 | OCH₂CH=CHCl(Z) | H | H | 4-i-Pr | |
| 1-30 | OCH₂CCl=CHCl(E) | H | H | 4-i-Pr | 1.5583(20.5) |
| 1-31 | OPh | H | H | 4-i-Pr | |
| 1-32 | OMe | Me | H | 4-i-Pr | |
| 1-33 | OMe | Me | Me | 4-i-Pr | |
| 1-34 | OH | H | H | 4-i-Bu | |
| 1-35 | OMe | H | H | 4-i-Bu | 70-71 |
| 1-36 | OEt | H | H | 4-i-Bu | |
| 1-37 | O—n-Pr | H | H | 4-i-Bu | |
| 1-38 | O—i-Pr | H | H | 4-i-Bu | |
| 1-39 | O—c-Pen | H | H | 4-i-Bu | 1.5420(20.5) |
| 1-40 | OCH₂OMe | H | H | 4-i-Bu | 1.5341(23.0) |

TABLE 1-continued

| compound No. | AR$^1$ | R$^2$ | R$^3$ | (X)$_m$ | property value |
|---|---|---|---|---|---|
| 1-41 | OCH$_2$—c-Pr | H | H | 4-i-Bu | 1.5434(20.5) |
| 1-42 | OCH$_2$CH$_2$Cl | H | H | 4-i-Bu | 1.5440(20.5) |
| 1-43 | OCH$_2$CCl=CH$_2$ | H | H | 4-i-Bu | |
| 1-44 | OCH$_2$CH=CHCl(Z) | H | H | 4-i-Bu | |
| 1-45 | OCH$_2$CCl=CHCl(E) | H | H | 4-i-Bu | |
| 1-46 | OPh | H | H | 4-i-Bu | |
| 1-47 | OMe | Me | H | 4-i-Bu | |
| 1-48 | OMe | Me | Me | 4-i-Bu | |
| 1-49 | OMe | H | H | 4-neo-Pen | |
| 1-50 | OEt | H | H | 4-neo-Pen | |
| 1-51 | O—n-Pr | H | H | 4-neo-Pen | |
| 1-52 | O—i-Pr | H | H | 4-neo-Pen | |
| 1-53 | O—c-Pen | H | H | 4-neo-Pen | |
| 1-54 | OCH$_2$—c-Pr | H | H | 4-neo-Pen | |
| 1-55 | OCH$_2$CH$_2$Cl | H | H | 4-neo-Pen | |
| 1-56 | OCH$_2$CCl=CH$_2$ | H | H | 4-neo-Pen | |
| 1-57 | OCH$_2$CH=CHCl(Z) | H | H | 4-neo-Pen | |
| 1-58 | OCH$_2$CCl=CHCl(E) | H | H | 4-neo-Pen | |
| 1-59 | OPh | H | H | 4-neo-Pen | |
| 1-60 | OMe | Me | H | 4-neo-Pen | |
| 1-61 | OMe | Me | Me | 4-neo-Pen | |
| 1-62 | OMe | H | H | 4-TMS | 72-73 |
| 1-63 | OEt | H | H | 4-TMS | 1.5401(22.0) |
| 1-64 | O—n-Pr | H | H | 4-TMS | 1.5370(23.5) |
| 1-65 | O—i-Pr | H | H | 4-TMS | 1.5183(23.0) |
| 1-66 | O—c-Pen | H | H | 4-TMS | 1.5388(23.0) |
| 1-67 | OCH$_2$OMe | H | H | 4-TMS | 1.5360(24.5) |
| 1-68 | OCH$_2$—c-Pr | H | H | 4-TMS | 1.5419(23.0) |
| 1-69 | OCH$_2$CH$_2$Cl | H | H | 4-TMS | 1.5470(23.0) |
| 1-70 | OCH$_2$CCl=CH$_2$ | H | H | 4-TMS | 1.5479(22.0) |
| 1-71 | OCH$_2$CH=CHCl(Z) | H | H | 4-TMS | |
| 1-72 | OCH$_2$CCl=CHCl(E) | H | H | 4-TMS | 73-74 |
| 1-73 | OPh | H | H | 4-TMS | |
| 1-74 | OMe | H | H | 3-Cl-4-TMS | 48-49 |
| 1-75 | OMe | H | H | 2-Cl-4-TMS | |
| 1-76 | OMe | Me | H | 4-TMS | 1.5347(17.4) |
| 1-77 | OMe | Me | Me | 4-TMS | |
| 1-78 | OMe | H | H | 4-CF$_3$ | 57-58 |
| 1-79 | OEt | H | H | 4-CF$_3$ | |
| 1-80 | O—n-Pr | H | H | 4-CF$_3$ | 45-46 |
| 1-81 | O—i-Pr | H | H | 4-CF$_3$ | 41-42 |
| 1-82 | O—c-Pen | H | H | 4-CF$_3$ | 1.5057(23.5) |
| 1-83 | OCH$_2$OMe | H | H | 4-CF$_3$ | 60-61 |
| 1-84 | OCH$_2$SMe | H | H | 4-CF$_3$ | 46-47 |
| 1-85 | OCH$_2$SOMe | H | H | 4-CF$_3$ | 113-114 |
| 1-86 | OCH$_2$C≡CH | H | H | 4-CF$_3$ | 87-88 |
| 1-87 | OCH$_2$—c-Pr | H | H | 4-CF$_3$ | 45-46 |
| 1-88 | OCH$_2$CH$_2$F | H | H | 4-CF$_3$ | 52-53 |
| 1-89 | OCH$_2$CH$_2$Cl | H | H | 4-CF$_3$ | 48-49 |
| 1-90 | OCH$_2$CH=CH$_2$ | H | H | 4-CF$_3$ | 1.5153(26.0) |
| 1-91 | OCH$_2$CCl=CH$_2$ | H | H | 4-CF$_3$ | 1.5240(23.5) |
| 1-92 | OCH$_2$CH=CHCl(Z) | H | H | 4-CF$_3$ | 61-62 |
| 1-93 | OCH$_2$CCl=CHCl(E) | H | H | 4-CF$_3$ | 78-79 |
| 1-94 | OCH$_2$Ph | H | H | 4-CF$_3$ | 48-49 |
| 1-95 | OPh | H | H | 4-CF$_3$ | 56-57 |
| 1-96 | OMe | Me | H | 4-CF$_3$ | 1.5093(22.5) |
| 1-97 | OMe | Me | Me | 4-CF$_3$ | 1.5190(23.0) |
| 1-98 | OMe | H | H | 3-CF$_3$ | 63-64 |
| 1-99 | OMe | H | H | 2-CF$_3$ | 31-32 |
| 1-100 | OCH$_2$CH=CCl$_2$ | H | H | 4-CF$_3$ | 66-67 |
| 1-101 | OMe | i-Bu | H | 4-CF$_3$ | 76-78 |
| 1-102 | OCH$_2$CCl=CHCl(Z) | H | H | 4-CF$_3$ | 1.5268(23.5) |
| 1-103 | OMe | H | H | 4-OCF$_3$ | 75-76 |
| 1-104 | OEt | H | H | 4-OCF$_3$ | |
| 1-105 | O—n-Pr | H | H | 4-OCF$_3$ | |
| 1-106 | O—i-Pr | H | H | 4-OCF$_3$ | |
| 1-107 | O—c-Pen | H | H | 4-OCF$_3$ | 41-42 |
| 1-108 | OCH$_2$OMe | H | H | 4-OCF$_3$ | 51-52 |
| 1-109 | OCH$_2$—c-Pr | H | H | 4-OCF$_3$ | 62-64 |
| 1-110 | OCH$_2$CH$_2$Cl | H | H | 4-OCF$_3$ | 44-45 |
| 1-111 | OCH$_2$CCl=CH$_2$ | H | H | 4-OCF$_3$ | |
| 1-112 | OCH$_2$CH=CHCl(Z) | H | H | 4-OCF$_3$ | |
| 1-113 | OCH$_2$CCl=CHCl(E) | H | H | 4-OCF$_3$ | 73-76 |
| 1-114 | OPh | H | H | 4-OCF$_3$ | 1.5422(16.5) |
| 1-115 | OCOPh | H | H | 4-OCF$_3$ | 1.5381(21.5) |
| 1-116 | OMe | Me | H | 4-OCF$_3$ | 1.4871(21.5) |
| 1-117 | OCH$_2$OMe | Me | H | 4-OCF$_3$ | 1.4940(22.5) |

TABLE 1-continued

| compound No. | AR$^1$ | R$^2$ | R$^3$ | (X)$_m$ | property value |
|---|---|---|---|---|---|
| 1-118 | OMe | Me | Me | 4-OCF$_3$ | 1.5053(19.6) |
| 1-119 | OH | H | H | 4-OCF$_2$CF$_2$H | 163-164 |
| 1-120 | OMe | H | H | 4-OCF$_2$CF$_2$H | 65-66 |
| 1-121 | OEt | H | H | 4-OCF$_2$CF$_2$H | |
| 1-122 | O—n-Pr | H | H | 4-OCF$_2$CF$_2$H | 34-35 |
| 1-123 | O—i-Pr | H | H | 4-OCF$_2$CF$_2$H | |
| 1-124 | O—c-Pen | H | H | 4-OCF$_2$CF$_2$H | 1.5063(21.0) |
| 1-125 | OCH$_2$CF$_3$ | H | H | 4-OCF$_2$CF$_2$H | |
| 1-126 | OCH$_2$TMS | H | H | 4-OCF$_2$CF$_2$H | |
| 1-127 | OCH$_2$OMe | H | H | 4-OCF$_2$CF$_2$H | 1.5860(24.5) |
| 1-128 | OCH$_2$C≡CH | H | H | 4-OCF$_2$CF$_2$H | |
| 1-129 | OCH$_2$—c-Pr | H | H | 4-OCF$_2$CF$_2$H | 54-55 |
| 1-130 | OCH$_2$CH$_2$Cl | H | H | 4-OCF$_2$CF$_2$H | 1.5115(20.5) |
| 1-131 | OCH$_2$CCl=CH$_2$ | H | H | 4-OCF$_2$CF$_2$H | |
| 1-132 | OCH$_2$CH=CHCl(Z) | H | H | 4-OCF$_2$CF$_2$H | |
| 1-133 | OCH$_2$CCl=CHCl(E) | H | H | 4-OCF$_2$CF$_2$H | |
| 1-134 | OCH$_2$Ph | H | H | 4-OCF$_2$CF$_2$H | 1.5290(22.5) |
| 1-135 | OPh | H | H | 4-OCF$_2$CF$_2$H | 1.5364(22.0) |
| 1-136 | OMe | Me | H | 4-OCF$_2$CF$_2$H | |
| 1-137 | OMe | Me | Me | 4-OCF$_2$CF$_2$H | |
| 1-138 | OMe | H | H | 4-SCF$_3$ | 77-78 |
| 1-139 | OEt | H | H | 4-SCF$_3$ | 57-58 |
| 1-140 | O—n-Pr | H | H | 4-SCF$_3$ | |
| 1-141 | O—i-Pr | H | H | 4-SCF$_3$ | 31-32 |
| 1-142 | O—c-Pen | H | H | 4-SCF$_3$ | 47-48 |
| 1-143 | OCH$_2$—c-Pr | H | H | 4-SCF$_3$ | 45-46 |
| 1-144 | OCH$_2$CH$_2$Cl | H | H | 4-SCF$_3$ | 34-35 |
| 1-145 | OCH$_2$CCl=CH$_2$ | H | H | 4-SCF$_3$ | 1.5440(22.0) |
| 1-146 | OCH$_2$CH=CHCl(Z) | H | H | 4-SCF$_3$ | 47-48 |
| 1-147 | OCH$_2$CCl=CHCl(E) | H | H | 4-SCF$_3$ | 62-63 |
| 1-148 | OPh | H | H | 4-SCF$_3$ | 41-42 |
| 1-149 | OMe | Me | H | 4-SCF$_3$ | |
| 1-150 | OMe | Me | Me | 4-SCF$_3$ | |
| 1-151 | OMe | H | H | 4-SCF$_2$CF$_3$ | |
| 1-152 | OEt | H | H | 4-SCF$_2$CF$_3$ | |
| 1-153 | O—n-Pr | H | H | 4-SCF$_2$CF$_3$ | |
| 1-154 | O—i-Pr | H | H | 4-SCF$_2$CF$_3$ | |
| 1-155 | O—c-Pen | H | H | 4-SCF$_2$CF$_3$ | |
| 1-156 | OCH$_2$—c-Pr | H | H | 4-SCF$_2$CF$_3$ | 44-45 |
| 1-157 | OCH$_2$CH$_2$Cl | H | H | 4-SCF$_2$CF$_3$ | 39-40 |
| 1-158 | OCH$_2$CCl=CH$_2$ | H | H | 4-SCF$_2$CF$_3$ | |
| 1-159 | OCH$_2$CH=CHCl(Z) | H | H | 4-SCF$_2$CF$_3$ | |
| 1-160 | OCH$_2$CCl=CHCl(E) | H | H | 4-SCF$_2$CF$_3$ | |
| 1-161 | OPh | H | H | 4-SCF$_2$CF$_3$ | |
| 1-162 | OMe | Me | H | 4-SCF$_2$CF$_3$ | |
| 1-163 | OMe | Me | Me | 4-SCF$_2$CF$_3$ | |
| 1-164 | OMe | H | H | 4-SCF(CF$_3$)$_2$ | |
| 1-165 | OEt | H | H | 4-SCF(CF$_3$)$_2$ | |
| 1-166 | O—n-Pr | H | H | 4-SCF(CF$_3$)$_2$ | |
| 1-167 | O—i-Pr | H | H | 4-SCF(CF$_3$)$_2$ | |
| 1-168 | O—c-Pen | H | H | 4-SCF(CF$_3$)$_2$ | |
| 1-169 | OCH$_2$—c-Pr | H | H | 4-SCF(CF$_3$)$_2$ | |
| 1-170 | OCH$_2$CH$_2$Cl | H | H | 4-SCF(CF$_3$)$_2$ | |
| 1-171 | OCH$_2$CCl=CH$_2$ | H | H | 4-SCF(CF$_3$)$_2$ | |
| 1-172 | OCH$_2$CH=CHCl(Z) | H | H | 4-SCF(CF$_3$)$_2$ | |
| 1-173 | OCH$_2$CCl=CHCl(E) | H | H | 4-SCF(CF$_3$)$_2$ | |
| 1-174 | OPh | H | H | 4-SCF(CF$_3$)$_2$ | |
| 1-175 | OMe | Me | H | 4-SCF(CF$_3$)$_2$ | |
| 1-176 | OMe | Me | Me | 4-SCF(CF$_3$)$_2$ | |
| 1-177 | OMe | H | H | 4-CF(CF$_3$)$_2$ | |
| 1-178 | OEt | H | H | 4-CF(CF$_3$)$_2$ | |
| 1-179 | O—n-Pr | H | H | 4-CF(CF$_3$)$_2$ | |
| 1-180 | O—i-Pr | H | H | 4-CF(CF$_3$)$_2$ | |
| 1-181 | O—c-Pen | H | H | 4-CF(CF$_3$)$_2$ | |
| 1-182 | OCH$_2$—c-Pr | H | H | 4-CF(CF$_3$)$_2$ | |
| 1-183 | OCH$_2$CH$_2$Cl | H | H | 4-CF(CF$_3$)$_2$ | |
| 1-184 | OCH$_2$CCl=CH$_2$ | H | H | 4-CF(CF$_3$)$_2$ | |
| 1-185 | OCH$_2$CH=CHCl(Z) | H | H | 4-CF(CF$_3$)$_2$ | |
| 1-186 | OCH$_2$CCl=CHCl(E) | H | H | 4-CF(CF$_3$)$_2$ | |
| 1-187 | OPh | H | H | 4-CF(CF$_3$)$_2$ | |
| 1-188 | OMe | Me | H | 4-CF(CF$_3$)$_2$ | |
| 1-189 | OMe | Me | Me | 4-CF(CF$_3$)$_2$ | |
| 1-190 | OMe | H | H | 4-F | 119-120 |
| 1-191 | OEt | H | H | 4-F | |
| 1-192 | O—n-Pr | H | H | 4-F | 1.5390(21.5) |
| 1-193 | O—i-Pr | H | H | 4-F | |
| 1-194 | O—c-Pen | H | H | 4-F | |

TABLE 1-continued

| compound No. | AR¹ | R² | R³ | (X)$_m$ | property value |
|---|---|---|---|---|---|
| 1-195 | OCH$_2$—c-Pr | H | H | 4-F | 1.5470(21.0) |
| 1-196 | OCH$_2$CH$_2$Cl | H | H | 4-F | |
| 1-197 | OCH$_2$CCl=CH$_2$ | H | H | 4-F | |
| 1-198 | OCH$_2$CH=CHCl(Z) | H | H | 4-F | |
| 1-199 | OCH$_2$CCl=(E) | H | H | 4-F | |
| 1-200 | OPh | H | H | 4-F | |
| 1-201 | OMe | Me | H | 4-F | |
| 1-202 | OMe | Me | Me | 4-F | |
| 1-203 | OMe | H | H | 3,4-F$_2$ | 99-101 |
| 1-204 | OMe | H | H | 2-Cl-4-F | 101-102 |
| 1-205 | OMe | H | H | 3-OPh | 1.5942(23.5) |
| 1-206 | OMe | H | H | 4-OPh | 1.5995(21.5) |
| 1-207 | OMe | H | H | 4-Br | 117-118 |
| 1-208 | OMe | H | H | 3-Cl | 52-53 |
| 1-209 | OMe | H | H | 4-Cl | 104-105 |
| 1-210 | OMe | H | H | 2,4-Cl$_2$ | 106-107 |
| 1-211 | OMe | H | H | 3-NO$_2$-4-Cl | 140-141 |
| 1-212 | OMe | H | H | 4-O—t-Bu | 57-58 |
| 1-213 | OMe | H | H | 4-SMe | 73-74 |
| 1-214 | OMe | H | H | 4-SOMe | 103-104 |
| 1-215 | OMe | H | H | 4-SO$_2$Me | 155-156 |
| 1-216 | OMe | H | H | 2-Cl-4-Br | 121-122 |
| 1-217 | OMe | H | H | 3-Cl-4-O—i-Pr | 58-59 |
| 1-218 | OMe | Me | H | 4-OCH$_2$CF$_3$ | 1.4980(23.0) |
| 1-219 | OMe | H | H | 4-c-Hex | 67-68 |
| 1-220 | OPh | H | H | 4-Br | 1.6136(20.7) |
| 1-221 | OMe | H | H | 4-O—c-Pen | 58-60 |
| 1-222 | OMe | H | H | 3,4-Cl$_2$ | 113-114 |
| 1-223 | OMe | H | H | 4-I | 115-116 |
| 1-224 | OMe | H | H | H | 31-32 |
| 1-225 | OMe | H | H | 4-O—c-Hex | 64-65 |
| 1-226 | OMe | H | H | 4-S—i-Pr | 73-74 |
| 1-227 | OMe | H | H | 4-O—i-Pr | 1.5536(22.0) |
| 1-228 | OCH$_2$OMe | H | H | 4-O—i-Pr | 1.5408(22.0) |
| 1-229 | OMe | H | H | 3,4,5-(OMe)$_3$ | 88-89 |
| 1-230 | OMe | H | H | 3,4-(OMe)$_2$ | 54-55 |
| 1-231 | OMe | Me | Me | H | 1.5486(22.6) |
| 1-232 | OMe | Me | H | 4-O—i-Pr | 1.5482(22.5) |
| 1-233 | OMe | H | H | 3-OMe-4-OEt | 76-77 |
| 1-234 | OMe | H | H | 4-Me | 46-47 |
| 1-235 | OMe | CF$_3$ | H | H | 86-87 |
| 1-236 | OMe | H | H | 2,3,4,5,6-F$_5$ | 73-74 |
| 1-237 | OMe | H | H | 2,5-F$_2$ | 104-105 |
| 1-238 | OMe | H | H | 4-CMe$_2$CH$_2$Me | |
| 1-239 | OMe | H | H | 4-CMe$_2$CH$_2$Cl | |
| 1-240 | OMe | H | H | 4-OCF$_2$H | 50-51 |
| 1-241 | OMe | H | H | 4-SCF$_2$H | |
| 1-242 | OMe | H | H | 2-F-4-Cl | 99-100 |
| 1-243 | OMe | H | H | 2-F-4-Br | 61-62 |
| 1-244 | SMe | H | H | 4-t-Bu | 1.5449(20.7) |
| 1-245 | SEt | H | H | 4-t-Bu | 1.5502(19.6) |
| 1-246 | SMe | H | H | 4-CF$_3$ | 52-53 |
| 1-247 | SEt | H | H | 4-CF$_3$ | 44-45 |
| 1-248 | O—n-Bu | H | H | 4-CF$_3$ | 1.4950(21.5) |
| 1-249 | O—i-Bu | H | H | 4-CF$_3$ | 45-46 |
| 1-250 | O—s-Bu | H | H | 4-CF$_3$ | 1.4965(22.5) |
| 1-251 | O-3-Pen | H | H | 4-CF$_3$ | 1.4959(22.5) |
| 1-252 | O-neo-Pen | H | H | 4-CF$_3$ | 57-58 |
| 1-253 | O—c-Hex | H | H | 4-CF$_3$ | 1.5048(20.5) |
| 1-254 | OCH$_2$C≡CMe | H | H | 4-CF$_3$ | 74-75 |
| 1-255 | OMe | H | H | 2-F-4-CF$_3$ | |
| 1-256 | O—n-Pr | H | H | 2-F-4-CF$_3$ | 42-45 |
| 1-257 | O—i-Bu | H | H | 2-F-4-CF$_3$ | 38-42 |
| 1-258 | O—s-Bu | H | H | 2-F-4-CF$_3$ | 1.492(21.5) |
| 1-259 | O—c-Pen | H | H | 2-F-4-CF$_3$ | 1.508(26.5) |
| 1-260 | OCH$_2$—c-Pr | H | H | 2-F-4-CF$_3$ | 35-36 |
| 1-261 | OPh | H | H | 2-F-4-CF$_3$ | 65-66 |
| 1-262 | OMe | H | H | 2-Cl-4-CF$_3$ | |
| 1-263 | O—n-Pr | H | H | 2-Cl-4-CF$_3$ | |
| 1-264 | O—i-Bu | H | H | 2-Cl-4-CF$_3$ | 57-59 |
| 1-265 | O—s-Bu | H | H | 2-Cl-4-CF$_3$ | 1.509(30.0) |
| 1-266 | OCH$_2$—c-Pr | H | H | 2-Cl-4-CF$_3$ | 51-53 |
| 1-267 | OMe | H | H | 2-OMe-4-CF$_3$ | 99-100 |
| 1-268 | O—i-Bu | H | H | 2-OMe-4-CF$_3$ | |
| 1-269 | O—s-Bu | H | H | 2-OMe-4-CF$_3$ | |
| 1-270 | OMe | H | H | 2-NO$_2$-4-CF$_3$ | 123-126 |
| 1-271 | OMe | H | H | 2-F-4-OCHF$_2$ | |

TABLE 1-continued

| compound No. | AR¹ | R² | R³ | (X)$_m$ | property value |
|---|---|---|---|---|---|
| 1-272 | O—i-Bu | H | H | 2-F-4-OCHF$_2$ | |
| 1-273 | O—s-Bu | H | H | 2-F-4-OCHF$_2$ | |
| 1-274 | OMe | H | H | 2-F-4-OCF$_3$ | |
| 1-275 | O—i-Bu | H | H | 2-F-4-OCF$_3$ | |
| 1-276 | O—s-Bu | H | H | 2-F-4-OCF$_3$ | |
| 1-277 | OMe | H | H | 2-F-4-OCF$_2$CF$_2$H | |
| 1-278 | O—i-Bu | H | H | 2-F-4-OCF$_2$CF$_2$H | |
| 1-279 | O—s-Bu | H | H | 2-F-4-OCF$_2$CF$_2$H | |
| 1-280 | OMe | H | H | 2-F-4-OCH$_2$CF$_3$ | |
| 1-281 | O—i-Bu | H | H | 2-F-4-OCH$_2$CF$_3$ | |
| 1-282 | O—s-Bu | H | H | 2-F-4-OCH$_2$CF$_3$ | 1.4918(27.6) |
| 1-283 | OMe | H | H | 2-F-4-OCH$_2$CH$_2$F | |
| 1-284 | O—i-Bu | H | H | 2-F-4-OCH$_2$CH$_2$F | |
| 1-285 | O—s-Bu | H | H | 2-F-4-OCH$_2$CH$_2$F | |
| 1-286 | OMe | H | H | 2-F-4-O—i-Pr | |
| 1-287 | O—i-Bu | H | H | 2-F-4-O—i-Pr | |
| 1-288 | O—s-Bu | H | H | 2-F-4-O—i-Pr | |
| 1-289 | O—s-Bu(R FORM) | H | H | 4-CF$_3$ | 1.5000(24.5) |
| 1-290 | O—s-Bu(S FORM) | H | H | 4-CF$_3$ | 1.5000(24.5) |
| 1-291 | O—s-Bu(R FORM) | H | H | 4-t-Bu | |
| 1-292 | O—s-Bu(S FORM) | H | H | 4-t-Bu | |
| 1-293 | O—s-Bu(R FORM) | H | H | 4-TMS | |
| 1-294 | O—s-Bu(S FORM) | H | H | 4-TMS | |

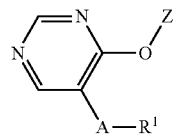

(I-1)

TABLE 2

| compound No. | AR¹ | Z | property value |
|---|---|---|---|
| 2-1 | OMe | ●—CH$_2$—C$_6$H$_4$—O—(3-CF$_3$-pyridin-2-yl) | 125-126 |
| 2-2 | OMe | ●—CH$_2$—C$_6$H$_4$—(3-methyl-5-CF$_3$-pyrazol-1-yl) | 113-114 |
| 2-3 | OMe | ●—CH$_2$—C$_6$H$_4$—(5-methyl-3-CF$_3$-pyrazol-1-yl) | 98-99 |

TABLE 2-continued
| compound No. | AR¹ | Z | property value |
|---|---|---|---|
| 2-4 | OMe | 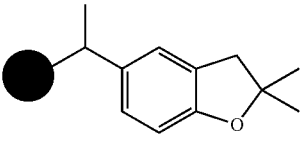 | 1.5518 (22.6) |
| 2-5 | OMe | 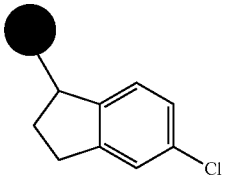 | 121-123 |
| 2-6 | O—n-Pr | 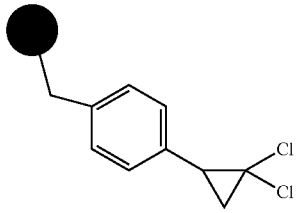 | 1.5718 (25.5) |
| 2-7 | O—s-Bu | 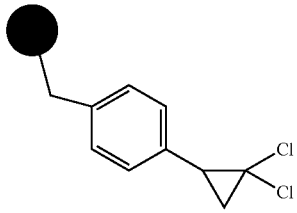 | 1.3361 (23.7) |
| 2-8 | O—s-Bu | 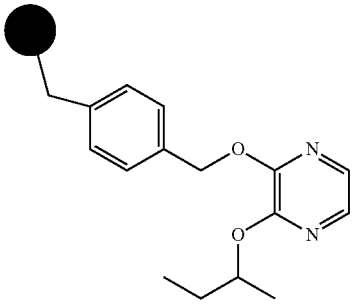 | 70-71 |
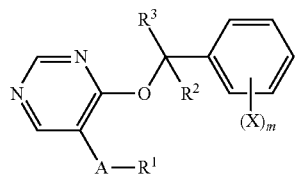
(I)
TABLE 3
| compound No. | AR¹ | R² | R³ | (X)ₘ | property value |
|---|---|---|---|---|---|
| 3-1 | O—n-Bu | H | H | 4-t-Bu | 1.5268 (22.5) |
| 3-2 | O—s-Bu | H | H | 4-t-Bu | 40-41 |
| 3-3 | O—n-Pen | H | H | 4-t-Bu | 1.5277 (23.0) |
| 3-4 | O-3-Pen | H | H | 4-t-Bu | NMR |

TABLE 3-continued

| compound No. | AR$^1$ | R$^2$ | R$^3$ | (X)$_m$ | property value |
|---|---|---|---|---|---|
| 3-5 | OCHMe—n-Pr | H | H | 4-t-Bu | 1.5219 (20.5) |
| 3-6 | OCHMe—c-Pr | H | H | 4-t-Bu | 1.5295 (22.5) |
| 3-7 | OCH$_2$CH=CH$_2$ | H | H | 4-t-Bu | 1.5400 (26.0) |
| 3-8 | O-2-THF | H | H | 4-t-Bu | 48-49 |
| 3-9 | OCH$_2$CH$_2$F | H | H | 4-t-Bu | 66-67 |
| 3-10 | OCH$_2$CHF$_2$ | H | H | 4-t-Bu | 1.3789 (17.1) |
| 3-11 | OCH$_2$CF$_3$ | H | H | 4-t-Bu | 1.5089 (21.0) |
| 3-12 | OCH$_2$CH$_2$CF$_3$ | H | H | 4-t-Bu | 55-56 |
| 3-13 | OCH$_2$CF$_2$CHF$_2$ | H | H | 4-t-Bu | 1.3806 (22.7) |
| 3-14 | OCH$_2$CF$_2$CF$_3$ | H | H | 4-t-Bu | 1.5007 (22.7) |
| 3-15 | OCH$_2$CH$_2$CH$_2$F | H | H | 4-t-Bu | 62-63 |
| 3-16 | OSO$_2$-4-Me—Ph | H | H | 4-t-Bu | 1.3445 (21.3) |
| 3-17 | OCH$_2$Ph | H | H | 4-t-Bu | 1.4780 (22.2) |
| 3-18 | O-2-Cl—Ph | H | H | 4-t-Bu | 1.5728 (26.0) |
| 3-19 | O-2-F—Ph | H | H | 4-t-Bu | 1.3945 (25.2) |
| 3-20 | O-2-Me—Ph | H | H | 4-t-Bu | 1.5683 (23.0) |
| 3-21 | O-2-OMe—Ph | H | H | 4-t-Bu | 83-84 |
| 3-22 | O-2,4-F$_2$—Ph | H | H | 4-t-Bu | 1.4028 (22.1) |
| 3-23 | O-2,6-F$_2$—Ph | H | H | 4-t-Bu | 1.3668 (20.7) |
| 3-24 | OCH$_2$OMe | CF$_3$ | H | 4-t-Bu | 1.4941 (17.5) |
| 3-25 | O—i-Pr | CF$_3$ | H | 4-t-Bu | 1.4921 (18.0) |
| 3-26 | O—c-Pen | CF$_3$ | H | 4-t-Bu | 1.5054 (17.0) |
| 3-27 | OMe | H | H | 2-OEt-4-t-Bu | 38-43 |
| 3-28 | OMe | H | H | 2-OMe-4-t-Bu | 99-101 |
| 3-29 | O—n-Bu | H | H | 4-i-Pr | 1.5380 (28.5) |
| 3-30 | O—i-Bu | H | H | 4-i-Pr | 1.5310 (24.5) |
| 3-31 | O—s-Bu | H | H | 4-i-Pr | 1.5310 (24.5) |
| 3-32 | O—c-Pen | H | H | 4-i-Pr | 1.5440 (26.5) |
| 3-33 | OCH$_2$OMe | H | H | 4-i-Pr | 1.5350 (24.5) |
| 3-34 | OCH$_2$CMe=CH$_2$ | H | H | 4-i-Pr | 1.5438 (22.5) |
| 3-35 | O-2-F—Ph | H | H | 4-i-Pr | 1.4017 (22.2) |
| 3-36 | O-2,4-F$_2$—Ph | H | H | 4-i-Pr | 1.4162 (22.0) |
| 3-37 | O—i-Bu | H | H | 4-TMS | 49-50 |
| 3-38 | O—s-Bu | H | H | 4-TMS | 1.5209 (21.0) |
| 3-39 | O—neo-Pen | H | H | 4-TMS | 1.5203 (22.0) |
| 3-40 | OCH$_2$CF$_3$ | H | H | 4-TMS | 1.5080 (22.0) |
| 3-41 | OCH$_2$CH$_2$F | H | H | 4-TMS | 1.5395 (22.0) |
| 3-42 | OCH$_2$CH$_2$OMe | H | H | 4-TMS | 1.3370 (22.0) |
| 3-43 | OCHMeCH$_2$Cl | H | H | 4-TMS | 42-43 |
| 3-44 | OCHMe—n-Pr | H | H | 4-TMS | 1.5290 (21.0) |
| 3-45 | OCH$_2$CMe=CH$_2$ | H | H | 4-TMS | 1.5400 (22.0) |
| 3-46 | OCH$_2$CCl=CHCl (Z) | H | H | 4-TMS | 1.5540 (22.0) |
| 3-47 | OCH$_2$-2-furanyl | H | H | 4-TMS | 1.5261 (22.0) |
| 3-48 | OCH$_2$-2-Py | H | H | 4-TMS | 73-74 |
| 3-49 | OCH$_2$-3-Py | H | H | 4-TMS | 49-50 |
| 3-50 | OCH$_2$-4-Py | H | H | 4-TMS | 53-54 |
| 3-51 | O-2-F—Ph | H | H | 4-TMS | |
| 3-52 | OCONMe$_2$ | H | H | 4-TMS | 1.5157 (22.0) |
| 3-53 | OCONEt$_2$ | H | H | 4-TMS | 1.5270 (21.5) |
| 3-54 | O—c-Bu | H | H | 4-CF$_3$ | 55-56 |
| 3-55 | O—c-Hep | H | H | 4-CF$_3$ | 1.5139 (20.5) |
| 3-56 | OCHMe—n-Pr | H | H | 4-CF$_3$ | 1.4980 (20.5) |
| 3-57 | OCHMe—i-Pr | H | H | 4-CF$_3$ | 1.4971 (22.5) |
| 3-58 | OCHMe—c-Pr | H | H | 4-CF$_3$ | 1.5038 (22.5) |
| 3-59 | OCH$_2$—c-Pen | H | H | 4-CF$_3$ | 42-43 |
| 3-60 | OCH$_2$—c-Hex | H | H | 4-CF$_3$ | 42-43 |
| 3-61 | OCH$_2$CHMeEt | H | H | 4-CF$_3$ | 1.4986 (20.5) |
| 3-62 | OCHMeCH$_2$Cl | H | H | 4-CF$_3$ | 1.5125 (21.0) |
| 3-63 | OCH$_2$SO$_2$Me | H | H | 4-CF$_3$ | 90-91 |
| 3-64 | OCH$_2$OEt | H | H | 4-CF$_3$ | 49-50 |
| 3-65 | OCH$_2$CN | H | H | 4-CF$_3$ | 72-73 |
| 3-66 | OCH$_2$TMS | H | H | 4-CF$_3$ | 50-52 |
| 3-67 | OCH$_2$CH$_2$OMe | H | H | 4-CF$_3$ | 1.5084 (23.0) |
| 3-68 | OCH$_2$CH$_2$Ph | H | H | 4-CF$_3$ | 1.5398 (22.0) |
| 3-69 |  | H | H | 4-CF$_3$ | 1.5271 (21.0) |
| 3-70 | 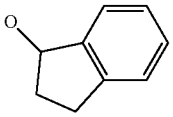 | H | H | 4-CF$_3$ | 51-52 |

TABLE 3-continued

| compound No. | AR$^1$ | R$^2$ | R$^3$ | (X)$_m$ | property value |
|---|---|---|---|---|---|
| 3-71 | OCH$_2$CH=CHCl (E) | H | H | 4-CF$_3$ | 98-99 |
| 3-72 | OCH$_2$CH=CHMe (E) | H | H | 4-CF$_3$ | 60-61 |
| 3-73 | OCHMeCH=CH$_2$ | H | H | 4-CF$_3$ | 1.5021 (22.5) |
| 3-74 | OCH$_2$CMe=CH$_2$ | H | H | 4-CF$_3$ | 33-34 |
| 3-75 | OC(Me)$_2$CH=CH$_2$ | H | H | 4-CF$_3$ | 1.5005 (21.5) |
| 3-76 | OCHMeC≡CH | H | H | 4-CF$_3$ | 64-65 |
| 3-77 | OC(Me)$_2$C≡CH | H | H | 4-CF$_3$ | 49-50 |
| 3-78 | O-2-THF | H | H | 4-CF$_3$ | 1.5132 (26.0) |
| 3-79 | O-3-THF | H | H | 4-CF$_3$ | 76-77 |
| 3-80 | OCH$_2$CF$_2$H | H | H | 4-CF$_3$ | 54-55 |
| 3-81 | OCH$_2$CF$_3$ | H | H | 4-CF$_3$ | 1.4672 (28.9) |
| 3-82 | OCH$_2$CH$_2$CH$_2$F | H | H | 4-CF$_3$ | 52-54 |
| 3-83 | OCH$_2$CH$_2$CH=CF$_2$ | H | H | 4-CF$_3$ | 1.3835 (19.0) |
| 3-84 | OCHMePh | H | H | 4-CF$_3$ | 1.5341 (22.5) |
| 3-85 | OCH$_2$-2-OMe—Ph | H | H | 4-CF$_3$ | 81-82 |
| 3-86 | OCH$_2$-4-OMe—Ph | H | H | 4-CF$_3$ | 100-101 |
| 3-87 | OCH$_2$-2-F—Ph | H | H | 4-CF$_3$ | 73-74 |
| 3-88 | OCH$_2$-3-F—Ph | H | H | 4-CF$_3$ | 54-55 |
| 3-89 | OCH$_2$-4-F—Ph | H | H | 4-CF$_3$ | 41-42 |
| 3-90 | OCH$_2$-2,6-F$_2$—Ph | H | H | 4-CF$_3$ | 52-53 |
| 3-91 | O-2-F—Ph | H | H | 4-CF$_3$ | 1.5300 (28.0) |
| 3-92 | O-3-F—Ph | H | H | 4-CF$_3$ | 1.5232 (28.0) |
| 3-93 | O-4-F—Ph | H | H | 4-CF$_3$ | 1.5289 (28.6) |
| 3-94 | O-2-Cl—Ph | H | H | 4-CF$_3$ | 83-84 |
| 3-95 | O-2-CF$_3$—Ph | H | H | 4-CF$_3$ | 38-40 |
| 3-96 | O-2-Me—Ph | H | H | 4-CF$_3$ | 1.5448 (23.0) |
| 3-97 | O-2-i-Pr—Ph | H | H | 4-CF$_3$ | 1.5360 (24.5) |
| 3-98 | O-2-OMe—Ph | H | H | 4-CF$_3$ | 52-53 |
| 3-99 | O-2,4-F$_2$—Ph | H | H | 4-CF$_3$ | 66-68 |
| 3-100 | O-2,6-F$_2$—Ph | H | H | 4-CF$_3$ | 85-86 |
| 3-101 | O-2-Py | H | H | 4-CF$_3$ | |
| 3-102 | O-3-Cl-5-CF$_3$-2-Py | H | H | 4-CF$_3$ | 72-73 |
| 3-103 | O-3-CF$_3$-2-Py | H | H | 4-CF$_3$ | 1.5070 (22.5) |
| 3-104 | O-5-CF$_3$-2-Py | H | H | 4-CF$_3$ | 1.5154 (22.5) |
| 3-105 | O-6-CF$_3$-2-Py | H | H | 4-CF$_3$ | 1.4879 (22.5) |
| 3-106 | O-4-CF$_3$-2-Py | H | H | 4-CF$_3$ | 1.5086 (22.0) |
| 3-107 | OCH$_2$-c-Pr | Me | H | 4-CF$_3$ | 55-56 |
| 3-108 | OMe | Et | H | 4-CF$_3$ | 72-73 |
| 3-109 | OMe | c-Pr | H | 4-CF$_3$ | 73-74 |
| 3-110 | OMe | c-Pen | H | 4-CF$_3$ | 59-60 |
| 3-111 | OMe | H | H | 2-F-5-CF$_3$ | |
| 3-112 | O—i-Bu | H | H | 2-F-5-CF$_3$ | 1.4892 (29.5) |
| 3-113 | O—s-Bu | H | H | 2-F-5-CF$_3$ | 1.4886 (29.5) |
| 3-114 | OCH$_2$OMe | H | H | 2-F-5-CF$_3$ | 67-68 |
| 3-115 | OMe | H | H | 3-F-4-CF$_3$ | |
| 3-116 | O—i-Bu | H | H | 3-F-4-CF$_3$ | |
| 3-117 | O—s-Bu | H | H | 3-F-4-CF$_3$ | 1.4850 (28.5) |
| 3-118 | OMe | H | H | 3-CF$_3$ | |
| 3-119 | O—i-Bu | H | H | 3-CF$_3$ | |
| 3-120 | O—s-Bu | H | H | 3-CF$_3$ | 1.4842 (28.6) |
| 3-121 | O—i-Bu | H | H | 2-F-3-CF$_3$ | 1.4811 (25.3) |
| 3-122 | O—s-Bu | H | H | 2-F-3-CF$_3$ | 1.4880 (28.6) |
| 3-123 | O—n-Bu | H | H | 4-OCF$_3$ | 30-31 |
| 3-124 | O—i-Bu | H | H | 4-OCF$_3$ | 1.4928 (21.5) |
| 3-125 | O—s-Bu | H | H | 4-OCF$_3$ | 1.4948 (21.5) |
| 3-126 | O—c-Hex | H | H | 4-OCF$_3$ | 1.5083 (16.5) |
| 3-127 | OCH$_2$-2-THF | H | H | 4-OCF$_3$ | 53-58 |
| 3-128 | OCH$_2$-2-furanyl | H | H | 4-OCF$_3$ | 1.5281 (19.0) |
| 3-129 | OCH$_2$Ph | H | H | 4-OCF$_3$ | 46-49 |
| 3-130 | OCH$_2$CCl=CHCl (Z) | H | H | 4-OCF$_3$ | 38-39 |
| 3-131 | OC(Me)$_2$C≡CH | H | H | 4-OCF$_3$ | 1.5025 (22.5) |
| 3-132 | O-2-F—Ph | H | H | 4-OCF$_3$ | 37-38 |
| 3-133 | O-2-Cl—Ph | H | H | 4-OCF$_3$ | 1.5416 (23.0) |
| 3-134 | O-2-Me—Ph | H | H | 4-OCF$_3$ | 1.5354 (24.6) |
| 3-135 | O-2-OMe—Ph | H | H | 4-OCF$_3$ | 1.5382 (24.6) |
| 3-136 | O—s-Bu | H | H | 3-F-4-OCF$_3$ | 1.4802 (28.8) |
| 3-137 | OCOMe | H | H | 4-OCF$_2$CF$_2$H | 1.4911 (22.5) |
| 3-138 | OCHMePh | H | H | 4-OCF$_2$CF$_2$H | 1.5352 (22.5) |
| 3-139 | O—i-Bu | H | H | 4-SCF$_3$ | 40-41 |
| 3-140 | O—s-Bu | H | H | 4-SCF$_3$ | 32-33 |
| 3-141 | OCH$_2$-2-THF | H | H | 4-SCF$_3$ | 1.5382 (22.0) |
| 3-142 | OCH$_2$OMe | H | H | 4-SCF$_3$ | 57-58 |
| 3-143 | OCH$_2$CH$_2$F | H | H | 4-SCF$_3$ | 62-63 |
| 3-144 | OCH$_2$Ph | H | H | 4-SCF$_3$ | 52-53 |
| 3-145 | OCH$_2$OMe | H | H | 4-SCF$_2$CF$_3$ | 43-44 |
| 3-146 | O—i-Bu | H | H | 4-F | 38-39 |
| 3-147 | O—s-Bu | H | H | 4-F | 1.524 (21.5) |

TABLE 3-continued

| compound No. | AR$^1$ | R$^2$ | R$^3$ | (X)$_m$ | property value |
|---|---|---|---|---|---|
| 3-148 | OCH$_2$OMe | H | H | 4-F | 54-57 |
| 3-149 | OMe | H | H | 2-F | |
| 3-150 | O—n-Pr | H | H | 2-F | |
| 3-151 | O—i-Bu | H | H | 2-F | |
| 3-152 | O—s-Bu | H | H | 2-F | 1.5242 (28.0) |
| 3-153 | OMe | H | H | 2,4-F$_2$ | 105-106 |
| 3-154 | O—n-Pr | H | H | 2,4-F$_2$ | 1.5260 (21.0) |
| 3-155 | O—i-Pr | H | H | 2,4-F$_2$ | |
| 3-156 | O—i-Bu | H | H | 2,4-F$_2$ | 1.516 (26.5) |
| 3-157 | O—s-Bu | H | H | 2,4-F$_2$ | 1.516 (26.5) |
| 3-158 | OCH$_2$OMe | H | H | 2,4-F$_2$ | 55-58 |
| 3-159 | OPh | H | H | 2,4-F$_2$ | 45-46 |
| 3-160 | OMe | H | H | 2,6-F$_2$ | |
| 3-161 | O—n-Pr | H | H | 2,6-F$_2$ | |
| 3-162 | O—i-Pr | H | H | 2,6-F$_2$ | |
| 3-163 | O—i-Bu | H | H | 2,6-F$_2$ | |
| 3-164 | O—s-Bu | H | H | 2,6-F$_2$ | 1.5150 (28.0) |
| 3-165 | OMe | H | H | H | |
| 3-166 | O—n-Pr | H | H | H | |
| 3-167 | O—i-Bu | H | H | H | |
| 3-168 | O—s-Bu | H | H | H | 1.5352 (27.5) |
| 3-169 | OMe | Me | H | H | 1.5622 (17.8) |
| 3-170 | OMe | c-Pr | H | H | 71-72 |
| 3-171 | OCH$_2$OMe | CF$_3$ | H | H | 1.4870 (17.5) |
| 3-172 | O—c-Pen | CF$_3$ | H | H | 1.5110 (17.5) |
| 3-173 | OCH$_2$CCl=CHCl (Z) | CF$_3$ | H | H | 1.5323 (17.5) |
| 3-174 | OCH$_2$CCl=CHCl (E) | CF$_3$ | H | H | 1.5294 (17.5) |
| 3-175 | OPh | CF$_3$ | H | H | 1.5436 (19.0) |
| 3-176 | OC(Me)$_2$C≡CH | CF$_3$ | H | H | 1.4720 (22.5) |
| 3-177 | OMe | CO$_2$Me | H | H | 113-114 |
| 3-178 | OMe | CH$_2$OMe | H | H | 1.5549 (20.0) |
| 3-179 | O—n-Pr | H | H | 4-Cl | 34-35 |
| 3-180 | O—i-Pr | H | H | 4-Cl | 55-56 |
| 3-181 | O—i-Bu | H | H | 4-Cl | 1.5490 (20.5) |
| 3-182 | O—s-Bu | H | H | 4-Cl | 1.5506 (20.5) |
| 3-183 | OCH$_2$—c-Pr | H | H | 4-Cl | 42-43 |
| 3-184 | OCH$_2$OMe | H | H | 4-Cl | 71-72 |
| 3-185 | O—n-Pr | Me | H | 4-Cl | 1.5533 (20.6) |
| 3-186 | OPh | CF$_3$ | H | 4-Cl | 1.5483 (18.0) |
| 3-187 | OMe | CF$_3$ | H | 4-Cl | 76-77 |
| 3-188 | OCH$_2$OMe | CF$_3$ | H | 4-Cl | 1.5141 (22.0) |
| 3-189 | OMe | CH$_2$SMe | H | 4-Cl | 1.5881 (22.5) |
| 3-190 | O—n-Pr | H | H | 2,4-Cl$_2$ | 62-64 |
| 3-191 | O—s-Bu | H | H | 4-Br | 1.5650 (21.0) |
| 3-192 | O—s-Bu | H | H | 4-I | 49-50 |
| 3-193 | OEt | H | H | 4-OCF$_2$H | |
| 3-194 | O—n-Pr | H | H | 4-OCF$_2$H | 1.5202 (20.5) |
| 3-195 | O—i-Pr | H | H | 4-OCF$_2$H | |
| 3-196 | O—i-Bu | H | H | 4-OCF$_2$H | |
| 3-197 | O—s-Bu | H | H | 4-OCF$_2$H | |
| 3-198 | OMe | H | H | 4-Me | |
| 3-199 | O—n-Pr | H | H | 4-Me | 1.5418 (28.5) |
| 3-200 | O—i-Pr | H | H | 4-Me | |
| 3-201 | O—i-Bu | H | H | 4-Me | |
| 3-202 | O—s-Bu | H | H | 4-Me | |
| 3-203 | OMe | H | H | 4-SMe | |
| 3-204 | O—n-Pr | H | H | 4-SMe | |
| 3-205 | O—i-Bu | H | H | 4-SMe | |
| 3-206 | O—s-Bu | H | H | 4-SMe | 1.5720 (28.5) |
| 3-207 | O—s-Bu | H | H | 4-s-Bu | 1.5252 (27.5) |
| 3-208 | O—s-Bu | H | H | 4-SO$_2$Me | 1.5513 (27.5) |
| 3-209 | O—i-Bu | H | H | 4-CMe$_2$Et | 1.5250 (27.5) |
| 3-210 | OMe | H | H | 4-OCH$_2$CF$_3$ | |
| 3-211 | O—n-Pr | H | H | 4-OCH$_2$CF$_3$ | 37-38 |
| 3-212 | O—i-Pr | H | H | 4-OCH$_2$CF$_3$ | |
| 3-213 | O—i-Bu | H | H | 4-OCH$_2$CF$_3$ | 31-32 |
| 3-214 | O—s-Bu | H | H | 4-OCH$_2$CF$_3$ | 1.4972 (28.7) |
| 3-215 | O-2-F—Ph | H | H | 4-OCH$_2$CF$_3$ | 82-83 |
| 3-216 | O—s-Bu | H | H | 4-OCH$_2$CF$_2$CF$_2$H | 1.4905 (28.5) |
| 3-217 | O—s-Bu | H | H | 4-O—i-Pr | 1.3353 (22.2) |
| 3-218 | O—s-Bu | H | H | 3-F-4-O—i-Pr | 1.4028 (22.2) |
| 3-219 | OMe | H | H | 4-n-Pr | 39-40 |
| 3-220 | OMe | H | H | 4-c-Pr | |
| 3-221 | O—n-Pr | H | H | 4-c-Pr | |
| 3-222 | O—i-Pr | H | H | 4-c-Pr | |
| 3-223 | O—i-Bu | H | H | 4-c-Pr | 38-39 |
| 3-224 | O—s-Bu | H | H | 4-c-Pr | 1.5249 (21.3) |

TABLE 3-continued

| compound No. | AR¹ | R² | R³ | (X)ₘ | property value |
|---|---|---|---|---|---|
| 3-225 | O-2-F—Ph | H | H | 4-c-Pr | 1.5842 (19.7) |
| 3-226 | OMe | H | H | 4-OMe | |
| 3-227 | O—n-Pr | H | H | 4-OMe | |
| 3-228 | O—i-Pr | H | H | 4-OMe | |
| 3-229 | O—i-Bu | H | H | 4-OMe | 1.5434 (21.3) |
| 3-230 | O—s-Bu | H | H | 4-OMe | 1.5413 (21.3) |
| 3-231 | OMe | H | H | 4-CH₂OCH₂CF₃ | |
| 3-232 | O—n-Pr | H | H | 4-CH₂OCH₂CF₃ | |
| 3-233 | O—i-Pr | H | H | 4-CH₂OCH₂CF₃ | |
| 3-234 | O—i-Bu | H | H | 4-CH₂OCH₂CF₃ | |
| 3-235 | O—s-Bu | H | H | 4-CH₂OCH₂CF₃ | 1.4422 (21.3) |
| 3-236 | SOMe | H | H | 4-t-Bu | |
| 3-237 | SO₂Me | H | H | 4-t-Bu | |
| 3-238 | SOEt | H | H | 4-t-Bu | |
| 3-239 | SO₂Et | H | H | 4-t-Bu | |
| 3-240 | S—i-Pr | H | H | 4-t-Bu | |
| 3-241 | SO—i-Pr | H | H | 4-t-Bu | |
| 3-242 | SO₂—i-Pr | H | H | 4-t-Bu | |
| 3-243 | SPh | H | H | 4-t-Bu | 1.5906 (22.2) |
| 3-244 | SOPh | H | H | 4-t-Bu | |
| 3-245 | SO₂Ph | H | H | 4-t-Bu | |
| 3-246 | SOMe | H | H | 4-CF₃ | |
| 3-247 | SO₂Me | H | H | 4-CF₃ | |
| 3-248 | SOEt | H | H | 4-CF₃ | |
| 3-249 | SO₂Et | H | H | 4-CF₃ | |
| 3-250 | S—i-Pr | H | H | 4-CF₃ | |
| 3-251 | SO—i-Pr | H | H | 4-CF₃ | |
| 3-252 | SO₂—i-Pr | H | H | 4-CF₃ | |
| 3-253 | SPh | H | H | 4-CF₃ | 67-68 |
| 3-254 | SOPh | H | H | 4-CF₃ | 149-150 |
| 3-255 | SO₂Ph | H | H | 4-CF₃ | 129-130 |
| 3-256 | SMe | H | H | 4-OCF₃ | |
| 3-257 | SOMe | H | H | 4-OCF₃ | |
| 3-258 | SO₂Me | H | H | 4-OCF₃ | |
| 3-259 | SEt | H | H | 4-OCF₃ | |
| 3-260 | SOEt | H | H | 4-OCF₃ | |
| 3-261 | SO₂Et | H | H | 4-OCF₃ | |
| 3-262 | S—i-Pr | H | H | 4-OCF₃ | |
| 3-263 | SO—i-Pr | H | H | 4-OCF₃ | |
| 3-264 | SO₂—i-Pr | H | H | 4-OCF₃ | |
| 3-265 | SPh | H | H | 4-OCF₃ | 42-43 |
| 3-266 | SOPh | H | H | 4-OCF₃ | |
| 3-267 | SO₂Ph | H | H | 4-OCF₃ | |
| 3-268 | O-3-Py | H | H | 4-CF₃ | |
| 3-269 | O-4-Py | H | H | 4-CF₃ | |

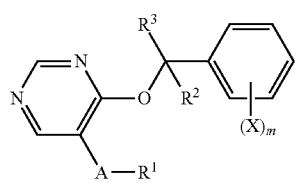

(I)

TABLE 4

| compound No. | AR¹ | R² | R³ | (X)ₘ | property value | remarks |
|---|---|---|---|---|---|---|
| 4-1 | OMe | H | H | 4-t-Bu | | hydrochloride |
| 4-2 | OMe | H | H | 4-t-Bu | | paratosylate |
| 4-3 | OMe | H | H | 4-t-Bu | | oxalate |
| 4-4 | O-n-Pr | H | H | 4-t-Bu | | hydrochloride |
| 4-5 | O-n-Pr | H | H | 4-t-Bu | | paratosylate |
| 4-6 | O-n-Pr | H | H | 4-t-Bu | | oxalate |
| 4-7 | O-i-Pr | H | H | 4-t-Bu | | hydrochloride |
| 4-8 | O-i-Pr | H | H | 4-t-Bu | | paratosylate |
| 4-9 | O-i-Pr | H | H | 4-t-Bu | | oxalate |
| 4-10 | O-i-Bu | H | H | 4-t-Bu | 120-128 | hydrochloride |
| 4-11 | O-i-Bu | H | H | 4-t-Bu | 119-121 | paratosylate |
| 4-12 | O-i-Bu | H | H | 4-t-Bu | 137-141 | oxalate |
| 4-13 | O-s-Bu | H | H | 4-t-Bu | | hydrochloride |
| 4-14 | O-s-Bu | H | H | 4-t-Bu | | paratosylate |
| 4-15 | O-s-Bu | H | H | 4-t-Bu | | oxalate |
| 4-16 | OPh | H | H | 4-t-Bu | | hydrochloride |
| 4-17 | OPh | H | H | 4-t-Bu | | paratosylate |
| 4-18 | OPh | H | H | 4-t-Bu | | oxalate |
| 4-19 | O-2-F—Ph | H | H | 4-t-Bu | | hydrochloride |
| 4-20 | O-2-F—Ph | H | H | 4-t-Bu | | paratosylate |
| 4-21 | O-2-F—Ph | H | H | 4-t-Bu | | oxalate |
| 4-22 | OMe | H | H | 4-TMS | | hydrochloride |
| 4-23 | OMe | H | H | 4-TMS | | paratosylate |
| 4-24 | OMe | H | H | 4-TMS | | oxalate |
| 4-25 | O-n-Pr | H | H | 4-TMS | | hydrochloride |
| 4-26 | O-n-Pr | H | H | 4-TMS | | paratosylate |
| 4-27 | O-n-Pr | H | H | 4-TMS | | oxalate |
| 4-28 | O-i-Pr | H | H | 4-TMS | | hydrochloride |
| 4-29 | O-i-Pr | H | H | 4-TMS | | paratosylate |
| 4-30 | O-i-Pr | H | H | 4-TMS | | oxalate |
| 4-31 | O-i-Bu | H | H | 4-TMS | | hydrochloride |

TABLE 4-continued

| compound No. | AR¹ | R² | R³ | (X)$_m$ | property value | remarks |
|---|---|---|---|---|---|---|
| 4-32 | O-i-Bu | H | H | 4-TMS | | paratosylate |
| 4-33 | O-i-Bu | H | H | 4-TMS | | oxalate |
| 4-34 | O-s-Bu | H | H | 4-TMS | | hydrochloride |
| 4-35 | O-s-Bu | H | H | 4-TMS | | paratosylate |
| 4-36 | O-s-Bu | H | H | 4-TMS | | oxalate |
| 4-37 | OPh | H | H | 4-TMS | | hydrochloride |
| 4-38 | OPh | H | H | 4-TMS | | paratosylate |
| 4-39 | OPh | H | H | 4-TMS | | oxalate |
| 4-40 | O-2-F—Ph | H | H | 4-TMS | | hydrochloride |
| 4-41 | O-2-F—Ph | H | H | 4-TMS | | paratosylate |
| 4-42 | O-2-F—Ph | H | H | 4-TMS | | oxalate |
| 4-43 | OMe | H | H | 4-CF$_3$ | | hydrochloride |
| 4-44 | OMe | H | H | 4-CF$_3$ | | paratosylate |
| 4-45 | OMe | H | H | 4-CF$_3$ | | oxalate |
| 4-46 | O-n-Pr | H | H | 4-CF$_3$ | | hydrochloride |
| 4-47 | O-n-Pr | H | H | 4-CF$_3$ | | paratosylate |
| 4-48 | O-n-Pr | H | H | 4-CF$_3$ | | oxalate |
| 4-49 | O-i-Pr | H | H | 4-CF$_3$ | | hydrochloride |
| 4-50 | O-i-Pr | H | H | 4-CF$_3$ | | paratosylate |
| 4-51 | O-i-Pr | H | H | 4-CF$_3$ | | oxalate |
| 4-52 | O-i-Bu | H | H | 4-CF$_3$ | | hydrochloride |
| 4-53 | O-i-Bu | H | H | 4-CF$_3$ | | paratosylate |
| 4-54 | O-i-Bu | H | H | 4-CF$_3$ | | oxalate |
| 4-55 | O-s-Bu | H | H | 4-CF$_3$ | 110-115 | hydrochloride |
| 4-56 | O-s-Bu | H | H | 4-CF$_3$ | 97-99 | paratosylate |
| 4-57 | O-s-Bu | H | H | 4-CF$_3$ | 115-119 | oxalate |
| 4-58 | OPh | H | H | 4-CF$_3$ | | hydrochloride |
| 4-59 | OPh | H | H | 4-CF$_3$ | | paratosylate |
| 4-60 | OPh | H | H | 4-CF$_3$ | | oxalate |
| 4-61 | O-2-F—Ph | H | H | 4-CF$_3$ | | hydrochloride |
| 4-62 | O-2-F—Ph | H | H | 4-CF$_3$ | | paratosylate |
| 4-63 | O-2-F—Ph | H | H | 4-CF$_3$ | | oxalate |
| 4-64 | OMe | H | H | 2-F-4-CF$_3$ | | hydrochloride |
| 4-65 | OMe | H | H | 2-F-4-CF$_3$ | | paratosylate |
| 4-66 | OMe | H | H | 2-F-4-CF$_3$ | | oxalate |
| 4-67 | O-n-Pr | H | H | 2-F-4-CF$_3$ | | hydrochloride |
| 4-68 | O-n-Pr | H | H | 2-F-4-CF$_3$ | | paratosylate |
| 4-69 | O-n-Pr | H | H | 2-F-4-CF$_3$ | | oxalate |
| 4-70 | O-i-Pr | H | H | 2-F-4-CF$_3$ | | hydrochloride |
| 4-71 | O-i-Pr | H | H | 2-F-4-CF$_3$ | | paratosylate |
| 4-72 | O-i-Pr | H | H | 2-F-4-CF$_3$ | | oxalate |
| 4-73 | O-i-Bu | H | H | 2-F-4-CF$_3$ | | hydrochloride |
| 4-74 | O-i-Bu | H | H | 2-F-4-CF$_3$ | | paratosylate |
| 4-75 | O-i-Bu | H | H | 2-F-4-CF$_3$ | | oxalate |
| 4-76 | O-s-Bu | H | H | 2-F-4-CF$_3$ | | hydrochloride |
| 4-77 | O-s-Bu | H | H | 2-F-4-CF$_3$ | | paratosylate |
| 4-78 | O-s-Bu | H | H | 2-F-4-CF$_3$ | | oxalate |
| 4-79 | OPh | H | H | 2-F-4-CF$_3$ | | hydrochloride |
| 4-80 | OPh | H | H | 2-F-4-CF$_3$ | | paratosylate |
| 4-81 | OPh | H | H | 2-F-4-CF$_3$ | | oxalate |
| 4-82 | OMe | H | H | 4-OCF$_3$ | | hydrochloride |
| 4-83 | OMe | H | H | 4-OCF$_3$ | | paratosylate |
| 4-84 | OMe | H | H | 4-OCF$_3$ | | oxalate |
| 4-85 | O-n-Pr | H | H | 4-OCF$_3$ | | hydrochloride |
| 4-86 | O-n-Pr | H | H | 4-OCF$_3$ | | paratosylate |
| 4-87 | O-n-Pr | H | H | 4-OCF$_3$ | | oxalate |
| 4-88 | O-i-Pr | H | H | 4-OCF$_3$ | | hydrochloride |
| 4-89 | O-i-Pr | H | H | 4-OCF$_3$ | | paratosylate |
| 4-90 | O-i-Pr | H | H | 4-OCF$_3$ | | oxalate |
| 4-91 | O-i-Bu | H | H | 4-OCF$_3$ | | hydrochloride |
| 4-92 | O-i-Bu | H | H | 4-OCF$_3$ | | paratosylate |
| 4-93 | O-i-Bu | H | H | 4-OCF$_3$ | | oxalate |
| 4-94 | O-s-Bu | H | H | 4-OCF$_3$ | | hydrochloride |
| 4-95 | O-s-Bu | H | H | 4-OCF$_3$ | | paratosylate |
| 4-96 | O-s-Bu | H | H | 4-OCF$_3$ | | oxalate |
| 4-97 | OPh | H | H | 4-OCF$_3$ | | hydrochloride |
| 4-98 | OPh | H | H | 4-OCF$_3$ | | paratosylate |
| 4-99 | OPh | H | H | 4-OCF$_3$ | | oxalate |
| 4-100 | OMe | H | H | 4-OCF$_3$ | | hydrochloride |
| 4-101 | OMe | H | H | 4-OCF$_3$ | | paratosylate |
| 4-102 | OMe | H | H | 4-OCF$_3$ | | oxalate |
| 4-103 | O-n-Pr | H | H | 4-OCF$_3$ | | hydrochloride |
| 4-104 | O-n-Pr | H | H | 4-OCF$_3$ | | paratosylate |
| 4-105 | O-n-Pr | H | H | 4-OCF$_3$ | | oxalate |
| 4-106 | O-i-Bu | H | H | 4-OCF$_3$ | | hydrochloride |
| 4-107 | O-i-Bu | H | H | 4-OCF$_3$ | | paratosylate |
| 4-108 | O-i-Bu | H | H | 4-OCF$_3$ | | oxalate |
| 4-109 | O-s-Bu | H | H | 4-OCF$_3$ | | hydrochloride |
| 4-110 | O-s-Bu | H | H | 4-OCF$_3$ | | paratosylate |
| 4-111 | O-s-Bu | H | H | 4-OCF$_3$ | | oxalate |
| 4-112 | OPh | H | H | 4-OCF$_3$ | | hydrochloride |
| 4-113 | OPh | H | H | 4-OCF$_3$ | | paratosylate |
| 4-114 | OPh | H | H | 4-OCF$_3$ | | oxalate |
| 4-115 | OMe | H | H | 4-i-Pr | | hydrochloride |
| 4-116 | OMe | H | H | 4-i-Pr | | paratosylate |
| 4-117 | OMe | H | H | 4-i-Pr | | oxalate |
| 4-118 | O-n-Pr | H | H | 4-i-Pr | | hydrochloride |
| 4-119 | O-n-Pr | H | H | 4-i-Pr | | paratosylate |
| 4-120 | O-n-Pr | H | H | 4-i-Pr | | oxalate |
| 4-121 | O-i-Pr | H | H | 4-i-Pr | | hydrochloride |
| 4-122 | O-i-Pr | H | H | 4-i-Pr | | paratosylate |
| 4-123 | O-i-Pr | H | H | 4-i-Pr | | oxalate |
| 4-124 | O-i-Bu | H | H | 4-i-Pr | | hydrochloride |
| 4-125 | O-i-Bu | H | H | 4-i-Pr | | paratosylate |
| 4-126 | O-i-Bu | H | H | 4-i-Pr | | oxalate |
| 4-127 | O-s-Bu | H | H | 4-i-Pr | | hydrochloride |
| 4-128 | O-s-Bu | H | H | 4-i-Pr | | paratosylate |
| 4-129 | O-s-Bu | H | H | 4-i-Pr | | oxalate |
| 4-130 | OPh | H | H | 4-i-Pr | | hydrochloride |
| 4-131 | OPh | H | H | 4-i-Pr | | paratosylate |
| 4-132 | OPh | H | H | 4-i-Pr | | oxalate |
| 4-133 | OMe | H | H | 4-i-Bu | | hydrochloride |
| 4-134 | OMe | H | H | 4-i-Bu | | paratosylate |
| 4-135 | OMe | H | H | 4-i-Bu | | oxalate |
| 4-136 | O-n-Pr | H | H | 4-i-Bu | | hydrochloride |
| 4-137 | O-n-Pr | H | H | 4-i-Bu | | paratosylate |
| 4-138 | O-n-Pr | H | H | 4-i-Bu | | oxalate |
| 4-139 | O-i-Pr | H | H | 4-i-Bu | | hydrochloride |
| 4-140 | O-i-Pr | H | H | 4-i-Bu | | paratosylate |
| 4-141 | O-i-Pr | H | H | 4-i-Bu | | oxalate |
| 4-142 | O-i-Bu | H | H | 4-i-Bu | | hydrochloride |
| 4-143 | O-i-Bu | H | H | 4-i-Bu | | paratosylate |
| 4-144 | O-i-Bu | H | H | 4-i-Bu | | oxalate |
| 4-145 | O-s-Bu | H | H | 4-i-Bu | | hydrochloride |
| 4-146 | O-s-Bu | H | H | 4-i-Bu | | paratosylate |
| 4-147 | O-s-Bu | H | H | 4-i-Bu | | oxalate |
| 4-148 | OPh | H | H | 4-i-Bu | | hydrochloride |
| 4-149 | OPh | H | H | 4-i-Bu | | paratosylate |
| 4-150 | OPh | H | H | 4-i-Bu | | oxalate |
| 4-151 | OMe | H | H | 4-F | | hydrochloride |
| 4-152 | OMe | H | H | 4-F | | paratosylate |
| 4-153 | OMe | H | H | 4-F | | oxalate |
| 4-154 | O-n-Pr | H | H | 4-F | | hydrochloride |
| 4-155 | O-n-Pr | H | H | 4-F | | paratosylate |
| 4-156 | O-n-Pr | H | H | 4-F | | oxalate |
| 4-157 | O-i-Pr | H | H | 4-F | | hydrochloride |
| 4-158 | O-i-Pr | H | H | 4-F | | paratosylate |
| 4-159 | O-i-Pr | H | H | 4-F | | oxalate |
| 4-160 | O-i-Bu | H | H | 4-F | | hydrochloride |
| 4-161 | O-i-Bu | H | H | 4-F | | paratosylate |
| 4-162 | O-i-Bu | H | H | 4-F | | oxalate |
| 4-163 | O-s-Bu | H | H | 4-F | | hydrochloride |
| 4-164 | O-s-Bu | H | H | 4-F | | paratosylate |
| 4-165 | O-s-Bu | H | H | 4-F | | oxalate |
| 4-166 | OPh | H | H | 4-F | | hydrochloride |
| 4-167 | OPh | H | H | 4-F | | paratosylate |
| 4-168 | OPh | H | H | 4-F | | oxalate |
| 4-169 | OMe | H | H | 4-Cl | | hydrochloride |
| 4-170 | OMe | H | H | 4-Cl | | paratosylate |
| 4-171 | OMe | H | H | 4-Cl | | oxalate |
| 4-172 | O-n-Pr | H | H | 4-Cl | | hydrochloride |
| 4-173 | O-n-Pr | H | H | 4-Cl | | paratosylate |
| 4-174 | O-n-Pr | H | H | 4-Cl | | oxalate |
| 4-175 | O-i-Pr | H | H | 4-Cl | | hydrochloride |
| 4-176 | O-i-Pr | H | H | 4-Cl | | paratosylate |
| 4-177 | O-i-Pr | H | H | 4-Cl | | oxalate |
| 4-178 | O-i-Bu | H | H | 4-Cl | | hydrochloride |
| 4-179 | O-i-Bu | H | H | 4-Cl | | paratosylate |
| 4-180 | O-i-Bu | H | H | 4-Cl | | oxalate |
| 4-181 | O-s-Bu | H | H | 4-Cl | | hydrochloride |
| 4-182 | O-s-Bu | H | H | 4-Cl | | paratosylate |
| 4-183 | O-s-Bu | H | H | 4-Cl | | oxalate |

TABLE 4-continued

| compound No. | AR¹ | R² | R³ | (X)$_m$ | property value | remarks |
|---|---|---|---|---|---|---|
| 4-184 | OPh | H | H | 4-Cl | | hydrochloride |
| 4-185 | OPh | H | H | 4-Cl | | paratosylate |
| 4-186 | OPh | H | H | 4-Cl | | oxalate |
| 4-187 | OMe | H | H | H | | hydrochloride |
| 4-188 | OMe | H | H | H | | paratosylate |
| 4-189 | OMe | H | H | H | | oxalate |
| 4-190 | O-n-Pr | H | H | H | | hydrochloride |
| 4-191 | O-n-Pr | H | H | H | | paratosylate |
| 4-192 | O-n-Pr | H | H | H | | oxalate |
| 4-193 | O-i-Pr | H | H | H | | hydrochloride |
| 4-194 | O-i-Pr | H | H | H | | paratosylate |
| 4-195 | O-i-Pr | H | H | H | | oxalate |
| 4-196 | O-i-Bu | H | H | H | | hydrochloride |
| 4-197 | O-i-Bu | H | H | H | | paratosylate |
| 4-198 | O-i-Bu | H | H | H | | oxalate |
| 4-199 | O-s-Bu | H | H | H | | hydrochloride |
| 4-200 | O-s-Bu | H | H | H | | paratosylate |
| 4-201 | O-s-Bu | H | H | H | | oxalate |
| 4-202 | OPh | H | H | H | | hydrochloride |
| 4-203 | OPh | H | H | H | | paratosylate |
| 4-204 | OPh | H | H | H | | oxalate |

TABLE 5

NMR data

| compound No. | ¹H-NMR(CDCl₃/TMS, ppm) |
|---|---|
| 3-4 | 8.39(1H, s), 8.07(1H, s), 7.39(4H, s), 5.47(2H, s), 4.13(1H, m), 1.68(4H, m), 1.32(9H, s), 0.95(6H, t) |

The agrohorticultural insecticides containing the benzyloxypyrimidine derivative represented by the formula (I) of the present invention as an active ingredient are suitable for controlling various insect pests such as agrohorticultural insect pests, stored grain insect pests, sanitary insect pests, nematodes, etc., which are injurious to paddy rice, fruit trees, vegetables, other crops, flowers and ornamental plants, etc. They have a marked insecticidal effect, for example, on Lepidoptera including summer fruit tortrix (*Adoxophyes orana fasciata*), smaller tea tortrix (*Adoxophyes* sp.), Manchurian fruit moth (*Grapholita inopinata*), oriental fruit moth (*Grapholita molesta*), soybean pod borer (*Leguminivora glycinivorella*), mulberry leafroller (*Olethreutes mori*), tea leafroller (*Caloptilia thevivora*), *Caloptilia* sp. (*Caloptilia zachrysa*), apple leafminer (*Phyllonorycter ringoniella*), pear barkminer (*Spulerrina astaurota*), common white (*Pieris rapae* crucivora), tobacco budworm (*Helicoverpa* sp.), codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; Hemiptera including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolobus taonabae*), sweetpotato whitefly (*Bemisia tabaci*), greenhouse whitefly (*Trialeurodes vaporariorum*), turnip aphid (*Lipaphis erysimi*), green peach aphid (*Myzus persicae*), Indian wax scale (*Ceroplastes ceriferus*), cottony citrus scale (*Chloropulvinaria aurantii*), camphor scale (*Pseudaonidia* duplex), san Jose scale (*Comstockaspis perniciosa*), arrowhead scale (*Unaspis yanonensis*), etc.; Coleoptera including meadow nematode (*Pratylenchus* sp.), soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintioctopunctata*), azuki bean weevil (*Callosobruchus chinensis*), vegetable weevil (*Listroderes costirostris*), maize weevil (*Sitophilus zeamais*), boll weevil (*Anthonomus grandis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), etc.;

Diptera including melon fly (*Dacus cucurbitae*), oriental fruit fly (*Bactrocera dorsalis*), rice leafminer (*Agromyza oryzae*), onion maggot (*Delia antiqua*), seedcorn maggot (*Delia platura*), soybean pod gall midge (*Asphondylia* sp.), house fly (*Musca domestica*), common house mosquito (*Culex pipiens* pallens), etc.;

Tylenchida including root-lesion nematode (*Pratylenchus* sp.), potato cyst nematode (*Globodera rostochiensis*), root-knot nematode (*Meloidogyne* sp.), citrus nematode (*Tylenchulus semipenetrans*), *Aphelenchus* sp. (*Aphelenchus avenae*), chrysanthemum foliar nematode (*Aphelenchoides ritzemabosi*), etc.; and Acarina including citrus red mite (*Panonychus citri*), fruit tree red spider mite (*Panonychus ulmi*), carmine spider mite (*Tetranychus cinnabarinus*), Kanzawa spider mite (*Tetranychus Kanzawai* Kishida), two-spotted spider mite (*Tetranychus urticae* Koch), pink tea rust mite (*Acaphylla theae*), pink citrus rust mite (*Aculops pelekassi*), purple tea mice (*Calacarus carinatus*), pear rust mite (*Epitrimerus pyri*), etc.

In addition, it shows a remarkable termiticidal effect with a low dose against any termites including *Rhinotermitidae* such as formosan subterranean termite (*Coptotermes formosanus* Shiraki), Japanese subterranean termite (*Reticulitermes speratus* (Kolbe)); *Reticulitermes hesperus, Reticulitermes tibialis, Reticulitermes flavipes* etc. occurring in North America; *Reticulitermes lucifugus, Reticulitermes santonensis* etc. occurring on the coast of the Mediterranean Sea, America common dry-wood termite (*Incisitermes minor* (Hagen)); *Termitidae* such as Formosan termite (*Odontotermes formosanus* (Shiraki)), *Kalotermitidae* such as Daikoku dry-wood termite (*Cryptotermes domesticus* (Haviland)) and Termopsidae such as *Hodotermopsis japonica* (Holmgren) and the like, that damage house, architectural materials, furniture, leather, fiber, plastic processing product, electric cable, cables and the like. Moreover, it also shows a remarkable formicidal effect with a low dose against ants including Formicidae such as little black ant (*Monomorium pharaonis* Linnes), *Monomorium nipponense* Wheeler, *Camponotus kiusiuensis* Santschi, negro ant (*Formica japonica* Motschulsky), *Lasius fuliginosus* (Latreille) and the like, fire ant (*Solenopsis richteri, Solenopsis invicta, Solenopsis geminata*(F)) and the like occurring in North America, that invade agricultural crops, public facility in parks and the like, and houses and harm people.

Furthermore, the benzyloxypyrimidine derivative represented by the formula (I) of the present invention can also be used against ectoparasite in domestic animals such as cattle, horse, sheep and the like, pets such as dog, cat and the like,

*Simplicidentata* animals such as mouse, rat, hamster, squirrel and the like, *Carnivora* animals such as *Lagomorpha* animal, ferret and the like, and birds such as duck, chicken, dove and the like and has a strong insecticidal effect against ectoparasites, for example, *Aphaniptera* pests such as cat flea (*Ctenocephalides felis*), dog flea (*Ctenocephalides canis*), *Xenopsylla cheopis* and the like, *Acari* pests such as *Haemaphysalis longicornis, Boophilus microplus* and the like, *Anoplura* pests such as cattle louse (*Haematopinus eurysternus*), *Damalinia ovis* and the like.

The agrohorticultural insecticide containing the benzyloxypyrimidine derivative represented by the formula (I) of the present invention as an active ingredient has a marked controlling effect on the above-exemplified insect pests, which are injurious to paddy field crops, upland crops, fruit trees, vegetables and other crops, flowers and ornament plants, and the like. Therefore, the desired effect of the agrohorticultural insecticides of the present invention can be exhibited by applying the agents to the cultivation carrier such as seeds, paddy field water, stalks and leaves or soil of propagation facility, paddy field, field, fruit trees, vegetables, other crops or flowers and ornament plants and the like, at a season at which the insect pests are expected to appear, before their appearance or at the time when their appearance is confirmed. Particularly, preferable use form is application utilizing what is called penetration transferability by allowing absorption of the compound of the present invention from roots via or not via soil, by treating propagation soil for crops, flowers and ornamental plants and the like, planting hole soil for transplantation, plant foot, irrigation water, culture water for hydroponic culture and the like.

Recently, gene recombinant crop (herbicide resistant crop, insect pest resistant crop incorporated with insecticidal toxin generating gene, disease resistant crop incorporated with disease resistance inducer producing gene, taste improved crop, preservability improved crop, yield improved crop, etc.), insect sex pheromone (pheromone disrupting chemicals for leaf roller moths, cabbage armyworm, etc.), IPM (integrated pest management) technology using natural enemy insect have been progressed, and the agrohorticultural insecticide of the present invention can be used in combination with or by systematization with such technologies.

The plants, for which the agrohorticultural insecticide of the present invention can be used, are not specifically limited and, for example, it can be used for the following plants.

It can be applied to plants such as cereals (e.g. rice, barley, wheat, rye, oat, corn etc.); legume (soybean, adzuki bean, fava bean, bean, kidney bean, peanut, etc.); fruit trees and fruits (apple, citrus fruits, pear, grapes, peach, plum, cherry fruit, walnut, sweet chestnut, almond, banana, strawberry, etc.); vegetables (cabbage, tomato, spinach, broccoli, lettuce, onion, welsh onion, green pepper, eggplant, pepper etc.); root vegetables (carrot, potato, sweet potato, tannia, radish, lotus root, turnip, burdock, garlic etc.); crop for processing (cotton, hemp, beet, hop, sugar cane, sugar beet, olive, rubber, coffee, tobacco, tea, etc.); gourd (pumpkin, cucumber, oriental melon, watermelon, melon, etc.); feed crop (orchard grass, sorghum, timothy, clover, alfalfa, etc.); grass (Korean lawn grass, bent grass, etc.); crop for spicery (lavender, rosemary, thyme, parsley, pepper, ginger, etc.); flowers (chrysanthemum, rose, carnation, orchid, etc.), garden tree (gingko, Japanese cherry, aucuba etc.), forest tree (*Abies sachalinensis, Picea jezoensis*, pines, *Thujopsis dolabrata*, Japanese cedar, Japanese cypress etc.) and the like.

For control of various pests, the agrohorticultural insecticide of the present invention need only be applied to the plant expected to allow development of pests and nematode, as it is or after being properly diluted with or suspended in water or the like, in an amount effective for control of the pests or nematode. For example, for pests and nematodes that occur in fruit trees, cereals, vegetables and the like, the insecticide is sprayed on the stem and leaf parts, or absorbed from the root by seed treatments such as dipping the seeds in a drug, dressing of seeds, Calper treatment and the like, soil treatment such as soil whole layer blending, planting row application, bed soil blending, cell seedling treatment, planting hole treatment, plant foot treatment, top dress, box treatment of rice, water surface application etc., and the like. In addition, the agrohorticultural insecticide can also be used by application to a culture fluid for culture fluid (hydroponic) culture, application by smoking or tree stem injection and the like.

The agrohorticultural insecticide of the present invention need only be applied to the place expected to allow development of pests, as it is or after being properly diluted with or suspended in water or the like, in an amount effective for control of the pests. For example, spraying on grain-storage insects, house pests, hygiene pests, forest pests and the like, as well as application, smoking, bait to house and architectural materials and the like can also be employed for use.

As methods for seed treatment, conventional methods such as a method comprising penetration of the agent by dipping of seeds in the liquid agent obtained by diluting or not a liquid formulation or a solid formulation, a method comprising adhering a solid formulation or liquid formulation to the seed surface by admixing the formulation with seeds, dressing and the like, a method comprising admixing the formulation with adhesive carriers such as resin, polymer and the like and forming a coat on the seeds, a method comprising application near the seeds simultaneously with planting and the like can be mentioned.

The "seed" to be subjected to the seed treatment means a plant body in an early stage of growth, which is used for propagation, and includes seeds, as well as bulb, tuber, seed potato, germ, propagule, scaly bulb, a plant body for vegetative propagation by cutting propagation, and the like.

The "soil" and "cultivation carrier" for plant when practicing the method of use of the present invention mean supports for cultivation of plants, particularly supports for growing roots, and the material is not particularly limited. The material may be any as long as plants can grow therein and specific materials include, for example, soils, nursery mat, water and the like. As a specific material, sand, pumice, vermiculite, diatomaceous earth, agar, gelled substance, polymer substance, rock wool, glass wool, wood chip, bark and the like can also be used.

As a method of application to crop plant stem and leaves, or grain-storage insect, house pest, hygiene pest or forest pest, a method including appropriately diluting a liquid formulation such as emulsion, flowable formulation and the like or a solid formulation such as a wettable powder or water dispersible granule and the like with water and spraying same, a method of spraying a dust, or smoking and the like can be mentioned.

For application to the soil, for example, a method comprising application of a liquid formulation to the plant foot of plant body, nursery for raising seedling and the like with or without dilution in water, a method comprising application of granules to the plant foot of plant body or nursery for raising seedling, a method comprising application of dust, wettable powder, water dispersible granule, granule and the like before sowing or transplantation to allow them to be incorporated into the entire soil, a method comprising application planting pit, planting row and the like with dust, wettable powder, water dispersible granule, granule and the like before sowing or planting and the like can be mentioned.

In the case of the paddy rice nursery box, the formulation may vary depending on the timing of, for example, application on sowing, application during greening, application during transplanting and the like. The formulations of dust, water dispersible granule, granule and the like can be employed. Application is also possible by incorporation into the grove soil, wherein the grove soil may be mixed with dust, water dispersible granule, granule and the like and, for example, incorporation into bed soil, incorporation into cover soil, incorporation into the entire grove soil and the like can be employed. Simply, a grove soil and various formulations may be applied in alternate layers.

As a method of application to a paddy field, a solid formulation such as jumbo, pack, granule, water dispersible granule and the like, a liquid formulation such as flowable, emulsion and the like are generally sprayed on a flooded paddy field. Alternatively, during rice planting, a suitable formulation can also be applied or injected to soil directly or after blending with a fertilizer. Moreover, by utilizing a liquid agent such as emulsion, flowable and the like to a is water inlet and the flow source of water into paddy fields such as an irrigation apparatus and the like, a saving application along with the supply of water can also be performed.

For upland crops, treatment of seeds, a cultivation carrier to be placed near the plant body and the like during the period of from sowing to raising seedling is possible. For plants to be directly sown in the field, a direct treatment of seeds, a treatment of a plant foot of the plant under cultivation and the like are preferable. An application of granules, a soil injection treatment with a liquid agent with or without dilution with water and the like can be performed. It is also a preferable treatment to blend granules with a cultivation carrier before seeding, and seed the blend.

For a treatment on sowing or during raising seedling of a cultivated plant to be transplanted, a direct treatment of seeds, an soil injection treatment of nursery for raising seedling with a liquid agent or a dispersal treatment thereof with granules are preferable. In addition, treatment of a planting pit with granules and mixing of a cultivation carrier to be placed near the transplantation site with the granules during fix planting are also preferable treatments.

The agrohorticultural insecticide of the present invention is generally prepared into conveniently usable forms according to an ordinary manner for preparation of agrochemicals.

That is, the benzyloxypyrimidine derivative represented by the formula (I) of the present invention are blended with a suitable inert carrier and, optionally, an adjuvant in a proper proportion and prepared into a suitable preparation form such as a suspension, emulsifiable concentrate, soluble concentrate, wettable powder, granular wettable powder, granules, dust, tablets, pack or the like through dissolution, dispersion, suspension, mixing, impregnation, adsorption or sticking.

The inert carrier usable in the present invention may be either solid or liquid. As a material usable as the solid carrier, there can be exemplified soybean flour, cereal flour, wood flour, bark flour, saw dust, powdered tobacco stalks, powdered walnut shells, bran, powdered cellulose, extraction residue of vegetables, resins such as powdered synthetic polymers and the like, clays (e.g. kaolin, bentonite, and acid clay), talcs (e.g. talc and pyrophyllite), silica powders or flakes (e.g. diatomaceous earth, silica sand, mica and white carbon [synthetic, high-dispersion silicic acid, also called finely divided hydrated silica or hydrated silicic acid, some of commercially available products contain calcium silicate as the major component]), inorganic or mineral powders such as activated carbon, powdered sulfur, pumice, calcined diatomaceous earth, ground brick, fly ash, sand, calcium carbonate, calcium phosphate and the like, plastic carriers such as polyethylene, polypropylene, poly(vinylidene chloride) and the like, chemical fertilizers (e.g. ammonium sulfate, ammonium phosphate, ammonium nitrate, urea and ammonium chloride), and compost. These carriers may be used alone or as a mixture of two or more kinds thereof.

A material usable as the liquid carrier is selected from materials that have solubility in themselves or which, even without such solubility, are capable of dispersing an active ingredient with the aid of an adjuvant. The following are typical examples of the liquid carrier and can be used alone or as a mixture of two or more kinds thereof: water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, cellosolve, dipropyl ether and tetrahydrofuran), aliphatic hydrocarbons (e.g. kerosene and mineral oils), aromatic hydrocarbons (e.g. benzene, toluene, xylene, solvent naphtha and alkylnaphthalenes), halogenated hydrocarbons (e.g. dichloroethane, chloroform, carbon tetrachloride and chlorobenzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

The following are typical examples of the adjuvant, which are used depending upon purposes and used alone or in combination of two or more kinds, or in some cases, need not be used at all.

To emulsify, disperse, dissolve and/or wet a compound as an active ingredient, a surfactant such as polyoxyethylene alkyl ethers, polyoxyethylene alkylaryl ethers, polyoxyethylene higher fatty acid esters, polyoxyethylene resonates, polyoxyethylene sorbitan monolaurate, polyoxyethylene sorbitan monooleate, alkylarylsulfonates, naphthalene sulfonic acid condensation products, ligninsulfonates and higher alcohol sulfate esters can be used.

Further, to stabilize dispersion of, tackify and/or bind the compound as an active ingredient, casein, gelatin, starch, methyl cellulose, carboxymethyl cellulose, gum arabic, poly(vinyl alcohol)s, turpentine, bran oil, bentonite and ligninsulfonates and the like can be used. To improve the flowability of a solid product, waxes, stearates, alkyl phosphates and the like can be used.

Adjuvants such as naphthalenesulfonic acid condensation products and polycondensates of phosphates may be used as a peptizer for dispersible products, silicone oil and the like may also be used as a defoaming agent, and 1,2-benzisothiazolin-3-one, p-chloro-m-xylenol, butyl p-hydroxybenzoate and the like may also be used as a preservative.

Further, if necessary, functional spreading agents, active enhancers such as metabolic decomposition inhibitor like piperonyl butoxide, anti-freezing agents such as propylene glycol, antioxidizing agents such as BHT, ultraviolet absorbers, and other aids may also be used.

The content of the compound as active ingredient may be varied as required, and the compound as active ingredient may be used in a proportion properly chosen in the range of 0.01 to 90 parts by weight per 100 parts of the agrohorticultural agents of the present invention. For example, in dusts, granules, emulsion or wettable powders, the suitable content of the compound as active ingredient is from 0.01 to 50% by weight.

The applying dosage of the agrohorticultural insecticide of the present invention varies depending upon various factors such as a purpose, insect pests to be controlled, a growth state of a plant, tendency of insect pests appearance, weather, environmental conditions, a preparation form, an application method, an application site and application time. It may be properly chosen in the range of 0.001 g to 10 kg, preferably 0.01 g to 1 kg, (in terms of the compound as active ingredient) per 10 ares depending upon purposes.

The agrohorticultural insecticide of the present invention may be used in admixture with other agrohorticultural insecticides, acaricides, nematocides, fungicides, biotic pesticides or the like in order to expand both spectrum of controllable disease and insect pest and the period of time when effective application are possible or to reduce the dosage. Furthermore, the agrohorticultural insecticide of the present invention may be used in admixture with herbicides, plant growth regulators, fertilizers or the like, depending upon application situations.

As the other agrohorticultural insecticides, acaricides and nematocides, which are used for the above purpose, there can be exemplified agrohorticultural insecticides, acaricides and nematocides, such as Ethion, Trichlorfon, Methamidophos, Acephate, Dichlorvos, Mevinphos, Monocrotophos, Malathion, Dimethoate, Formothion, Mecarbam, Vamidothion, Thiometon, Disulfoton, Oxydeprofos, Naled, Methyl parathion, Fenitrothion, Cyanophos, Propaphos, Fenthion, Prothiofos, Profenofos, Isofenphos, Temephos, Phenthoate, Dimethylvinphos, Chlorfenvinphos, Tetrachlorvinphos, Phoxim, Isoxathion, Pyraclofos, Methidathion, Chlorpyrifos, Chlorpyrifos-methyl, Pyridaphenthion, Diazinon, Pirimiphos-methyl, Phosalone, Phosmet, Dioxabenzofos, Quinalphos, Terbufos, Ethoprophos, Cadusafos, Mesulfenfos, DPS (NK-0795), Phosphocarb, Fenamiphos, Isamidofos, Fosthiazate, Isazofos, Ethoprophos, Fenthion, Fostietane, Dichlofenthion, Thionazin, Sulprofos, Fensulfothion, Diamidafos, Pyrethrin, Allethrin, Prallethrin, Resmethrin, Permethrin, Tefluthrin, Bifenthrin, Fenpropathrin, Cypermethrin, α-Cypermethrin, Cyhalothrin, λ-Cyhalothrin, Deltamethrin, Acrinathrin, Fenvalerate, Esfenvalerate, Cycloprothrin, Etofenprox, Halfenprox, Silafluofen, Flucythrinate, Fluvalinate, Methomyl, Oxamyl, Thiodicarb, Aldicarb, Alanycarb, Cartap, Metolcarb, Xylylcarb, Propoxur, Fenoxycarb, fenobucarb, Ethiophencarb, Fenothiocarb, Bifenazate, Carbaryl, Pirimicarb, Carbofuran, Carbosulfan, Furathiocarb, Benfuracarb, Aldoxycarb, Diafenthiuron, Diflubenzuron, Teflubenzuron, Hexaflumuron, Novaluron, Lufenuron, Flufenoxuron, Chlorfluazuron, Fenbutatin oxide, Tricyclohexyltin hydroxide, Sodium oleate, Potassium oleate, Methoprene, Hydroprene, Binapacryl, Amitraz, Dicofol, Kelthane, Chlorobenzilate, Phenisobromolate, Tetradifon, Bensultap, Benzoximate, Tebufenozide, Methoxyfenozide, Pyridalyl, Flubendiamide, Pyrifluquinazon, metaflumizone, chlorantraniliprole, cyantraniliprole, Chromafenozide, Propargite, Acequinocyl, Endosulfan, Diofenolan, Chlorfenapyr, Fenpyroximate, Tolfenpyrad, Fipronil, Tebufenpyrad, Triazamate, Etoxazole, Hexythiazox, Nicotine sulfate, Nitenpyram, Acetamiprid, Thiacloprid, Imidacloprid, Thiamethoxam, Clothianidin, Dinotefuran, Fluazinam, Pyriproxyfen, Hydramethylnon, Pyrimidifen, Pyridaben, Cyromazine, TPIC (tripropyl isocyanurate), Pymetrozine, Clofentezine, Buprofezin, Thiocyclam, Fenazaquin, Chinomethionate, Indoxacarb, Polynactin complexes, Milbemectin, Abamectin, Emamectin-benzoate, Spinosad, BT (*Bacillus thuringiensis*), Azadirachtin, Rotenone, Hydroxypropyl starch, Levamisole hydrochloride, Metam-sodium, Morantel tartrate, Dazomet, Trichlamide, *Pasteuria penetrans, Monacrosporium-phymatophagum*, etc.

As the agrohorticultural fungicides used for the same purpose as above, there can be exemplified agrohorticultural fungicides such as Sulfur, Lime sulfur, Copper sulfate basic, Iprobenfos, Edifenphos, Tolclofos-methyl, Thiram, Polycarbamate, Zineb, Maneb, Mancozeb, Propineb, Thiophanate, Thiophanate methyl, Benomyl, Iminoctadine acetate, Iminocutadine albecylate, Mepronil, Flutolanil, Pencycuron, Furametpyr, Thifluzamide, Metalaxyl, Oxadixyl, Carpropamid, Dichlofluanid, Flusulfamide, Chlorothalonil, Kresoxim-methyl, Fenoxanil, Hymexazol, Etridiazole, Fluoroimide, Procymidone, Vinclozolin, Iprodione, Triadimefon, Triflumizole, Bitertanol, Ipconazole, Fluconazole, Propiconazole, Difenoconazole, Myclobutanil, Tetraconazole, Hexaconazole, Tebuconazole, Imibenconazole, Prochloraz, Pefurazoate, Cyproconazole, Isoprothiolane, Fenarimol, Pyrimethanil, Mepanipyrim, Pyrifenox, Fluazinam, Triforine, Diclomezine, Azoxystrobin, trifloxystrobin, orysastrobin, Thiadiazine, Captan, Probenazole, Acibenzolar-S-methyl(CGA-245704), Fthalide, Tricyclazole, Pyroquilon, Chinomethionat, Oxolinic acid, Dithianon, cyazofamid, Diclocymet, Kasugamycin, Validamycin, Polyoxin, Blasticidin, Streptomycin, Isotianil etc.

Similarly, as the herbicides, there can be exemplified herbicides such as Glyphosate, Sulfosate, Glufosinate, Bialaphos, Butamifos, Esprocarb, Prosulfocarb, Benthiocarb, Pyributicarb, Asulam, Linuron, Dymron, Isouron, Bensulfuron methyl, Cyclosulfamuron, Cinosulfuron, Pyrazosulfuron ethyl, Azimsulfuron, Imazosulfuron, Thenylchlor, Alachlor, Pretilachlor, Clomeprop, Etobenzanid, Mefenacet, Flufenacet, Fentrazamide, Pendimethalin, Bifenox, Acifluorfen, Lactfen, Cyhalofop-butyl, Ioxynil, Bromobutide, Alloxydim, Sethoxydim, Napropamide, Indanofan, Pyrazolate, Benzofenap, Pyraflufen-ethyl, Imazapyr, Sulfentrazone, Cafenstrole, Bentoxazon, Oxadiazon, Paraquat, Diquat, Pyriminobac, Simazine, Atrazine, Dimethametryn, Triaziflam, Benfuresate, Fluthiacet-methyl, Quizalofop-ethyl, Bentazone, Oxaziclomefone, Azafenidin, Benzobicyclon, Calcium peroxide, etc.

As to the biotic pesticides, the same effect as above can be expected by using the agrohorticultural agent of the present invention in admixture with, for example, viral formulations obtained from Nuclear polyhedrosis virus (NPV), Granulosis virus (GV), Cytoplasmic polyhedrosis virus (CPV), Entomopox virus (EPV), etc.; microbial pesticides utilized as insecticides or nematicides, such as *Monacrosporium phymatophagum, Steinernema carpocapsae, Steinernema kushidai, Pasteuria penetrans*, etc.; microbial pesticides utilized as fungicides, such as *Trichoderma lignorum, Agrobacterium radiobacter*, nonpathogenic *Erwinia carotovora, Bacillus subtilis*, etc.; and biotic pesticides utilized as herbicides, such as *Xanthomonas campestris*, etc.

In addition, the agrohorticultural agent of the present invention can be used in combination with biotic pesticides including natural enemies such as Parasitic wasp (*Encarsia formosa*), Parasitic wasp (*Aphidius colemani*), Gall-mildge (*Aphidoletes aphidimyza*), Parasitic wasp (*Diglyphus isaea*), Parasitic mite (*Dacnusa sibirica*), Predatory mite (*Phytoseiulus persimilis*), Predatory mite (*Amblyseius cucumeris*), Predatory bug (*Orius sauteri*), etc.; microbial pesticides such as *Beauveria brongniartii*, etc.; and pheromones such as (Z)-10-tetradecenyl acetate, (E,Z)-4,10-tetradecadieniel acetate, (Z)-8-dodecenyl acetate, (Z)-11-tetradecenyl acetate, (Z)-13-icosen-10-one, 14-methyl-1-octadecene, etc.

EXAMPLES

The representative Examples of the present invention are shown below, which are not to be construed as limitative.

Example 1

Production of 4-(4-t-butylbenzyloxy)-5-methoxypyrimidine (compound No. 1-1)

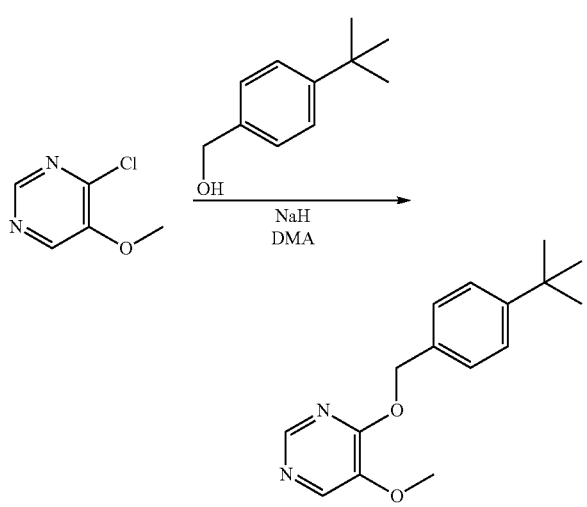

To a solution of 4-chloro-5-methoxypyrimidine (1.5 g, 10.3 mmol) described in Journal of the Chemical Society (1960), 4590, and 4-t-butylbenzylalcohol (2.55 g, 15.6 mmol) in dimethylacetamide (10 mL) was added sodium hydride (0.625 g, 15.6 mmol) at 0° C., and the mixture was stirred at room temperature for 3 hrs. The reaction mixture was poured into ice water, and extracted with ethyl acetate. The organic layer was dried over anhydrous magnesium sulfate, and the solvent was concentrated under reduced pressure. The residue was purified by silica gel column chromatography to give 4-(4-t-butylbenzyloxy)-5-methoxypyrimidine (2.16 g).

yield: 77% property: melting point 58-59° C.

Example 2

Production of 4-(4-trifluoromethylbenzyloxy)-5-phenoxypyrimidine (compound No. 1-95)

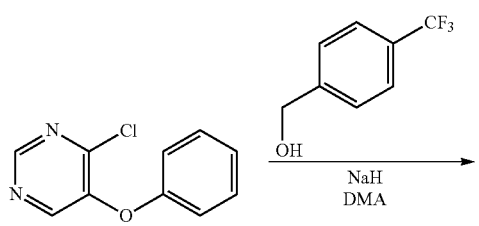

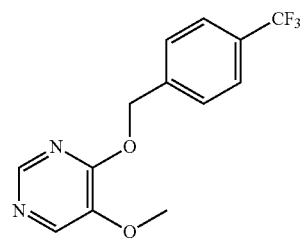

To a solution of 4-chloro-5-phenoxypyrimidine (0.4 g, 1.9 mmol) described in JP-A-49-92080 and 4-trifluoromethylbenzylalcohol (0.36 g, 2.0 mmol) in dimethylacetamide (7 m) was added sodium hydride (0.093 g, 2.3 mmol) at 0° C., and the mixture was stirred at room temperature for 3 hrs. The reaction mixture was poured into ice water, and the mixture was extracted with ethyl acetate. The organic layer was dried over anhydrous magnesium sulfate, and the solvent was concentrated under reduced pressure. The residue was purified by silica gel column chromatography to give 4-(4-trifluoromethylbenzyloxy)-5-phenoxypyrimidine (0.60 g).

yield: 85% melting point: 56-57° C.

Typical formulation examples and experimental example of the present invention are described below but they should not be construed as limiting the scope of the invention.

As used in the examples, the terms "part" and "parts" means parts by weight.

Formulation Example 1

| | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzenesulfonate | 10 parts |

An emulsifiable concentrate is prepared by mixing uniformly the above ingredients to effect dissolution.

Formulation Example 2

| | |
|---|---|
| Compound of the present invention | 3 parts |
| Clay powder | 82 parts |
| Diatomaceous earth powder | 15 parts |

A dust is prepared by mixing uniformly and grinding the above ingredients.

Formulation Example 3

| | |
|---|---|
| Compound of the present invention | 5 parts |
| Mixed powder of bentonite and clay | 90 parts |
| Calcium ligninsulfonate | 5 parts |

Granules are prepared by mixing the above ingredients uniformly, and kneading the resulting mixture together with a suitable amount of water, followed by granulation and drying.

Formulation Example 4

| | |
|---|---|
| Compound of the present invention | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder is prepared by mixing uniformly and grinding the above ingredients.

Experimental Example 1

Control Efficacy Against Green Peach Aphid (*Myzus persicae*)

A Chinese cabbage plant was planted in each of plastic pots with a diameter of 8 cm and a height of 8 cm and green peach aphids were propagated on the plant, after which the parasites in each pot were counted. Each pymidine derivative of the general formula (I) or a salt thereof of the present invention was dispersed in and diluted with water to obtain a 500 ppm liquid chemical. The stalks and leaves of the potted Chinese cabbage plants were sprayed with the liquid chemical and air-dried, and then the pots were stored in a greenhouse. Six days after the spraying, green peach aphids parasitic on each Chinese cabbage plant were counted and the control efficacy degree was calculated by the following equation, whereby the insecticidal effect was judged according to the criterion shown below.

Control efficacy=100−{(T×Ca)/(Ta×C)}×100

Ta: number of parasites before spraying in treated group,
T: number of parasites after spraying in treated group,
Ca: number of parasites before spraying in untreated group,
C: number of parasites after spraying in untreated group.
A . . . control efficacy 100%
B . . . control efficacy 99%-90%
C . . . control efficacy 89%-80%
D . . . control efficacy 79%-50%

Experimental Example 2

Insecticidal Effect on Brown Rice Planthopper (*Nilaparvata lugens*)

Each benzyloxypymidine derivative of the general formula (I) or a salt thereof of the present invention was dispersed in and diluted with water to obtain a 500 ppm liquid chemical. Rice seedlings (cultivar: Nihonbare) were immersed in the liquid chemical for 30 seconds and air-dried, after which each seedling was placed in a glass test tube and inoculated with 10 third-instar nymphs of brown rice planthopper, and the test tube was plugged with a cotton plug. Eight days after the inoculation, the dead and alive were counted. The mortality was calculated by the following equation and the control effect was judged according to the criterion described below.

$$\text{Corrected mortality (\%)} = \frac{(\text{survival rate in untreated group}) - (\text{survival rate in treated group})}{(\text{survival rate in untreated group})} \times 100$$

diagnostic criteria . . . Same as in Experimental Example 1.

As a result, among the benzyloxypyrimidine derivatives of the present invention represented by the formula (I), the compounds of compound Nos. 1-1, 1-2, 1-3, 1-5, 1-6, 1-7, 1-8, 1-9, 1-10, 1-14, 1-15, 1-16, 1-18, 1-21, 1-23, 1-28, 1-30, 1-35, 1-39, 1-41, 1-42, 1-62, 1-63, 1-70, 1-72, 1-74, 1-76, 1-78, 1-80, 1-81, 1-83, 1-86, 1-88, 1-90, 1-92, 1-94, 1-95, 1-103, 1-107, 1-108, 1-109, 1-110, 1-113, 1-114, 1-115, 1-116, 1-120, 1-122, 1-124, 1-129, 1-130, 1-134, 1-135, 1-138, 1-139, 1-141, 1-142, 1-143, 1-144, 1-145, 1-147, 1-148, 1-156, 1-157, 1-205, 1-207, 1-208, 1-209, 1-210, 1-211, 1-212, 1-213, 1-214, 1-215, 1-216, 1-217, 1-218, 1-219, 1-222, 1-223, 1-224, 1-225, 1-226, 1-227, 1-228, 1-230, 1-231, 1-242, 1-243, 1-244, 1-246, 1-247, 1-248, 1-249, 1-250, 1-251, 1-252, 1-253, 1-254, 1-256, 1-257, 1-258, 1-259, 1-260, 1-264, 1-265, 1-266, 1-267, 1-270, 2-2, 2-3, 3-1, 3-2, 3-4, 3-5, 3-6, 3-7, 3-9, 3-11, 3-12, 3-13, 3-14, 3-16, 3-18, 3-19, 3-20, 3-21, 3-22, 3-24, 3-25, 3-26, 3-27, 3-28, 3-29, 3-30, 3-31, 3-32, 3-33, 3-34, 3-36, 3-37, 3-38, 3-39, 3-40, 3-41, 3-42, 3-43, 3-44, 3-45, 3-46, 3-47, 3-49, 3-52, 3-54, 3-56, 3-57, 3-58, 3-60, 3-61, 3-62, 3-64, 3-65, 3-66, 3-67, 3-68, 3-69, 3-70, 3-71, 3-72, 3-74, 3-75, 3-76, 3-77, 3-78, 3-81, 3-84, 3-85, 3-86, 3-88, 3-91, 3-93, 3-94, 3-96, 3-97, 3-103, 3-105, 3-107, 3-108, 3-109, 3-110, 3-112, 3-113, 3-114, 3-117, 3-120, 3-121, 3-122, 3-124, 3-125, 3-127, 3-129, 3-130, 3-131, 3-134, 3-135, 3-139, 3-140, 3-141, 3-142, 3-143, 3-144, 3-145, 3-146, 3-147, 3-148, 3-152, 3-153, 3-154, 3-157, 3-158, 3-159, 3-164, 3-168, 3-169, 3-170, 3-171, 3-172, 3-173, 3-174, 3-176, 3-177, 3-179, 3-180, 3-182, 3-183, 3-184, 3-185, 3-187, 3-188, 3-189, 3-190, 3-191, 3-192, 3-194, 3-199, 3-206, 3-207, 3-208, 3-209, 3-213, 3-214, 3-215, 3-216, 3-217, 3-218, 3-219, 3-223, 3-224, 3-229, 3-230, 3-235, 3-253, 3-254, 4-10, 4-55, 4-56 and 4-57 showed insecticidal effects of not less than D against green peach aphid, and particularly, the compounds of 1-1, 1-3, 1-7, 1-10, 1-15, 1-21, 1-23, 1-35, 1-62, 1-78, 1-83, 1-103, 1-108, 1-116, 1-120, 1-122, 1-138, 1-205, 1-209, 1-210, 1-211, 1-216, 1-217, 1-218, 1-219, 1-223, 1-226, 1-230, 1-244, 2-3, 3-1, 3-2, 3-6, 3-7, 3-9, 3-11, 3-13, 3-19, 3-22, 3-31, 3-33, 3-34, 3-36, 3-37, 3-42, 3-45, 3-54, 3-56, 3-57, 3-58, 3-60, 3-61, 3-62, 3-64, 3-67, 3-69, 3-70, 3-72, 3-74, 3-75, 3-77, 3-81, 3-91, 3-97, 3-103, 3-107, 3-108, 3-114, 3-117, 3-121, 3-131, 3-139, 3-140, 3-142, 3-143, 3-145, 3-157, 3-179, 3-180, 3-182, 3-185, 3-187, 3-194, 3-214, 3-215, 3-216, 3-218, 3-219, 3-229, 3-254, 4-55, 4-56 and 4-57 showed superior insecticidal effects of A.

Against brown rice planthopper, moreover, the compounds of compound Nos. 1-1, 1-2, 1-3, 1-4, 1-5, 1-6, 1-7, 1-8, 1-9, 1-10, 1-14, 1-15, 1-16, 1-18, 1-20, 1-21, 1-23, 1-26, 1-28, 1-30, 1-35, 1-39, 1-40, 1-41, 1-42, 1-62, 1-63, 1-64, 1-70, 1-72, 1-74, 1-76, 1-78, 1-80, 1-81, 1-83, 1-86, 1-88, 1-90, 1-92, 1-94, 1-95, 1-98, 1-99, 1-103, 1-107, 1-108, 1-109, 1-110, 1-113, 1-114, 1-116, 1-120, 1-122, 1-124, 1-129, 1-130, 1-135, 1-138, 1-139, 1-141, 1-142, 1-143, 1-144, 1-145, 1-146, 1-147, 1-148, 1-156, 1-157, 1-192, 1-195, 1-205, 1-207, 1-208, 1-209, 1-210, 1-212, 1-213, 1-214, 1-215, 1-216, 1-217, 1-218, 1-219, 1-222, 1-223, 1-224, 1-227, 1-228, 1-230, 1-231, 1-240, 1-242, 1-243, 1-244, 1-246, 1-247, 1-248, 1-249, 1-250, 1-251, 1-252, 1-253, 1-254, 1-256, 1-257, 1-258, 1-259, 1-260, 1-261, 1-264, 1-265, 1-266, 1-267, 1-270, 1-282, 1-289, 1-290, 2-2, 2-3, 2-6, 3-1, 3-2, 3-3, 3-4, 3-5, 3-6, 3-7, 3-8, 3-9, 3-11, 3-12, 3-13, 3-22, 3-24, 3-25, 3-26, 3-28, 3-29, 3-30, 3-31, 3-32, 3-33, 3-34, 3-37, 3-38, 3-39, 3-40, 3-41, 3-42, 3-43, 3-44, 3-45, 3-46, 3-47, 3-48, 3-49, 3-52, 3-54, 3-56, 3-57, 3-58, 3-60, 3-61, 3-62, 3-63, 3-64, 3-65, 3-66, 3-67, 3-68, 3-69, 3-70, 3-71, 3-72, 3-74, 3-75, 3-76, 3-77, 3-79, 3-81, 3-85, 3-86, 3-88, 3-89, 3-90, 3-91, 3-92, 3-93, 3-94, 3-97, 3-99, 3-102, 3-103, 3-107, 3-108, 3-109, 3-112, 3-113, 3-114, 3-117, 3-120, 3-122, 3-123, 3-124, 3-125, 3-126, 3-127, 3-128, 3-130, 3-131, 3-132, 3-136, 3-139, 3-140, 3-142, 3-143, 3-145, 3-146, 3-147, 3-148, 3-152, 3-153, 3-154, 3-156, 3-157, 3-158, 3-159, 3-164, 3-168, 3-169, 3-171, 3-172, 3-173, 3-174, 3-175, 3-176, 3-179, 3-180, 3-181, 3-182, 3-183, 3-184, 3-185, 3-186, 3-187, 3-188, 3-190, 3-191, 3-192, 3-194, 3-199, 3-206, 3-207, 3-208, 3-209, 3-211, 3-213, 3-214, 3-216, 3-217, 3-218, 3-219, 3-223, 3-224, 3-235, 4-10, 4-11, 4-12, 4-55, 4-56 and 4-57 showed superior insecticidal effects of A.

Experimental Example 3

Acaricidal Effect on Cattle Tick (*Haemaphysalis longicornis*)

An absorbent cotton was placed on the basement of a glass bottle (diameter 3 cm×height 4.5 cm). The pyrimidine derivative of the present invention represented by the formula (I) or a salt thereof was dispersed in water to give a diluted drug solution (100 ppm). The drug solution (2 ml) was added dropwise. Cattle ticks were inoculated by 5 each, and the bottle was capped with a mesh. After 4 days from the inoculation, the dead ticks and live ticks were counted, and the corrected mortality was calculated by the following formula.

corrected mortality (%)=(survival rate in untreated group−survival rate in treated group)/(survival rate in untreated group)×100

Diagnostic criteria . . . as defined in Experimental Example 1

As a result, among the benzyloxypyrimidine derivatives of the present invention represented by the formula (I), compound Nos. 1-1, 1-5, 1-14, 1-15, 1-62, 1-78, 1-103, 1-138, 1-190, 1-207, 1-209 and 1-212 showed acaricidal effects of not less than D against cattle tick.

Industrial Applicability

The benzyloxypyrimidine derivative of the present invention or a salt thereof has a superior effect as an agrohorticultural insecticide. On the other hand, the derivative shows an effect on pests being parasitic in pet animals such as dogs and cats, and domestic animals such as cattle, sheep and the like.

This application is based on patent application Nos. 287777/2010 and 181052/2011 filed in Japan, the contents of which are hereby incorporated by reference.

The invention claimed is:

1. A benzyloxypyrimidine derivative represented by the formula (I):

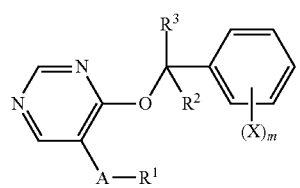

(I)

wherein
$R^1$ is
(a1) a hydrogen atom;
(a2) a $(C_1-C_6)$alkyl group;
(a3) a $(C_3-C_7)$cycloalkyl group (said cycloalkyl group is optionally fused with a benzene ring);
(a4) a $(C_2-C_6)$alkenyl group;
(a5) a $(C_2-C_6)$alkynyl group;
(a6) a halo$(C_1-C_6)$alkyl group;
(a7) a halo$(C_3-C_6)$cycloalkyl group;
(a9) a halo$(C_2-C_6)$alkynyl group;
(a10) a $(C_1-C_6)$alkoxy$(C_1-C_6)$alkyl group;
(a11) a $(C_3-C_6)$cycloalkyl$(C_1-C_6)$alkyl group;
(a12) a $(C_1-C_6)$alkylthio$(C_1-C_6)$alkyl group;
(a13) a $(C_1-C_6)$alkylsulfinyl$(C_1-C_6)$alkyl group;
(a14) a $(C_1-C_6)$alkylsulfonyl$(C_1-C_6)$alkyl group;
(a15) a halo$(C_1-C_6)$alkoxy$(C_1-C_6)$alkyl group;
(a16) a halo$(C_3-C_6)$cycloalkyl$(C_1-C_6)$alkyl group;
(a17) a halo$(C_1-C_6)$alkylthio$(C_1-C_6)$alkyl group;
(a18) a halo$(C_1-C_6)$alkylsulfinyl$(C_1-C_6)$alkyl group;
(a19) a halo$(C_1-C_6)$alkylsulfonyl$(C_1-C_6)$alkyl group;
(a20) a $(C_1-C_6)$alkoxyhalo$(C_1-C_6)$alkyl group;
(a21) a halo$(C_1-C_6)$alkoxyhalo$(C_1-C_6)$alkyl group;
(a22) an aryl$(C_1-C_6)$alkyl group;
(a23) an aryl$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, and (s) a $R^4(R^5)N$ carbonyl group wherein $R^4$ and $R^5$ may be the same or different and each is a hydrogen atom, a $(C_1-C_6)$alkyl group, a $(C_3-C_6)$cycloalkyl group, a $(C_2-C_6)$alkenyl group, a $(C_2-C_6)$alkynyl group, a $(C_3-C_6)$cycloalkyl$(C_1-C_6)$alkyl group, a halo$(C_1-C_6)$alkyl group, a halo$(C_3-C_6)$cycloalkyl group, a halo$(C_2-C_6)$alkenyl group, a halo$(C_2-C_6)$alkynyl group, a halo$(C_3-C_6)$cycloalkyl$(C_1-C_6)$alkyl group, a phenyl group, or a phenyl $(C_1-C_6)$alkyl group;
(a24) a cyano$(C_1-C_6)$alkyl group;
(a25) a nitro$(C_1-C_6)$alkyl group;
(a26) a $R^4(R^5)N(C_1-C_6)$alkyl group wherein $R^4$ and $R^5$ are as defined above;
(a27) a $(R^4)OC(C_1-C_6)$alkyl group wherein $R^4$ is as defined above;
(a28) a $(R^4)O_2C(C_1-C_6)$alkyl group wherein $R^4$ is as defined above;
(a29) a $R^4(R^5)NCO(C_1-C_6)$alkyl group wherein $R^4$ and $R^5$ are as defined above;
(a30) an aryl group;
(a31) an aryl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, and (t) a phenoxy group;
(a32) an arylsulfonyl group;

(a33) an arylsulfonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$) alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$) alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a34) an arylcarbonyl group;

(a35) an arylcarbonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo ($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo ($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a36) an arylthio($C_1$-$C_6$)alkyl group;

(a37) an arylthio($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo ($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo ($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a38) an arylsulfinyl($C_1$-$C_6$)alkyl group;

(a39) an arylsulfinyl($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a40) an arylsulfonyl($C_1$-$C_6$)alkyl group;

(a41) an arylsulfonyl($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a42) an arylcarbonyloxy($C_1$-$C_6$)alkyl group;

(a43) an arylcarbonyloxy($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a44) a ($C_1$-$C_6$)alkylcarbonyl group;

(a45) a ($C_1$-$C_6$)alkoxycarbonyl group;

(a47) a $R^4(R^5)$N carbonyloxy($C_1$-$C_6$)alkyl group wherein $R^4$ and $R^5$ are as defined above;

(a48) a tri($C_1$-$C_6$)alkylsilyl group wherein the alkyl groups may be the same or different;

(a49) a ($C_1$-$C_6$)alkoxy($C_1$-$C_6$)alkoxy($C_1$-$C_6$)alkyl group;

(a50) a ($C_1$-$C_6$)alkoxycarbonyloxy($C_1$-$C_6$)alkyl group;

(a51) a ($C_1$-$C_6$)alkyl($C_1$-$C_6$)sulfonyl group;

(a52) a heterocyclic group;

(a53) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$) alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$) alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, and (t) an oxo group;

(a54) a heterocyclyl($C_1$-$C_6$)alkyl group;

(a55) a heterocyclyl($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (l) a halo($C_1$-$C_6$)alkyl group, (g) a ($C_1$-$C_6$)alkoxy group, (h) a halo ($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo ($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, and (t) an oxo group;

(a56) a tri($C_1$-$C_6$)alkylsilyl($C_1$-$C_6$)alkyl group wherein the alkyl groups of the tri($C_1$-$C_6$)alkylsilyl may be the same or different; or (a57) a $R^4(R^5)$NCO group wherein $R^4$ and $R^5$ are as defined above, A is —O—, —S—, —SO— or —$SO_2$—, $R^2$ and $R^3$ may be the same or different, and each is (b1) a hydrogen atom;
(b2) a $(C_1\text{-}C_6)$alkyl group;
(b3) a $(C_3\text{-}C_6)$cycloalkyl group;
(b4) a $(C_2\text{-}C_6)$alkenyl group;
(b5) a $(C_2\text{-}C_6)$alkynyl group;
(b6) a halo$(C_1\text{-}C_6)$alkyl group;
(b7) a halo$(C_3\text{-}C_6)$cycloalkyl group;
(b8) a halo$(C_2\text{-}C_6)$alkenyl group;
(b9) a halo$(C_2\text{-}C_6)$alkynyl group;
(b10) a $(C_3\text{-}C_6)$cycloalkyl$(C_1\text{-}C_6)$alkyl group;
(b11) a $(C_1\text{-}C_6)$alkoxy$(C_1\text{-}C_6)$alkyl group;
(b12) a $(C_1\text{-}C_6)$alkylthio$(C_1\text{-}C_6)$alkyl group; or
(b13) a $(C_1\text{-}C_6)$alkoxycarbonyl group,
X may be the same or different, and each is
(c1) a hydrogen atom;
(c2) a halogen atom;
(c3) a hydroxyl group;
(c4) a cyano group;
(c5) a nitro group;
(c6) a $N(R^4)(R^5)$ group wherein $R^4$ and $R^5$ are as defined above;
(c7) a $N(R^4)CO(R^5)$ group wherein $R^4$ and $R^5$ are as defined above;
(c8) a $N(R^4)SO_2(R^5)$ group wherein $R^4$ and $R^5$ are as defined above;
(c9) a $N(R^4)CO_2(R^5)$ group wherein $R^4$ and $R^5$ are as defined above;
(c10) a $CO(R^4)$ group wherein $R^4$ is as defined above;
(c11) a $CO_2(R^4)$ group wherein $R^4$ is as defined above;
(c12) a $CON(R^4)(R^5)$ group wherein $R^4$ and $R^5$ are as defined above;
(c13) a $C(R^4)=NOR^5$ group wherein $R^4$ and $R^5$ are as defined above;
(c14) a $(C_1\text{-}C_{12})$alkyl group;
(c15) a $(C_2\text{-}C_{12})$alkenyl group;
(c16) a $(C_2\text{-}C_{12})$alkynyl group;
(c17) a $(C_3\text{-}C_{12})$cycloalkyl group;
(c18) a halo$(C_1\text{-}C_{12})$alkyl group;
(c19) a halo$(C_2\text{-}C_{12})$alkenyl group;
(c20) a halo$(C_2\text{-}C_{12})$alkynyl group;
(c21) a halo$(C_3\text{-}C_{12})$cycloalkyl group;
(c22) a tri$(C_1\text{-}C_{12})$alkylsilyl group wherein the alkyl groups may be the same or different;
(c23) a tri$(C_1\text{-}C_6)$alkylsilyl$(C_1\text{-}C_6)$alkyl group wherein the alkyl groups of the tri$(C_1\text{-}C_6)$alkylsilyl may be the same or different;
(c24) a $(C_3\text{-}C_{12})$cycloalkyl$(C_1\text{-}C_{12})$alkyl group;
(c25) a halo$(C_3\text{-}C_{12})$cycloalkyl$(C_1\text{-}C_{12})$alkyl group;
(c26) a $(C_3\text{-}C_{12})$cycloalkyl$(C_3\text{-}C_{12})$cycloalkyl group;
(c27) a $(C_1\text{-}C_{12})$alkoxy group;
(c28) a $(C_2\text{-}C_{12})$alkenyloxy group;
(c29) a $(C_2\text{-}C_{12})$alkynyloxy group;
(c30) a $(C_3\text{-}C_{12})$cycloalkyloxy group (said cycloalkyl is optionally fused with a benzene ring);
(c31) a halo$(C_1\text{-}C_{12})$alkoxy group;
(c32) a halo$(C_2\text{-}C_{12})$alkenyloxy group;
(c33) a halo$(C_2\text{-}C_{12})$alkynyloxy group;
(c34) a halo$(C_3\text{-}C_{12})$cycloalkyloxy group (said cycloalkyl is optionally fused with a benzene ring);
(c35) a $(C_3\text{-}C_{12})$cycloalkyl$(C_1\text{-}C_{12})$alkoxy group;
(c36) a halo$(C_3\text{-}C_{12})$cycloalkyl$(C_1\text{-}C_{12})$alkoxy group;
(c37) a $(C_1\text{-}C_6)$alkoxy$(C_1\text{-}C_6)$alkyl group;
(c38) a halo$(C_1\text{-}C_6)$alkoxy$(C_1\text{-}C_6)$alkoxy group;
(c39) a $(C_1\text{-}C_6)$alkoxyhalo$(C_1\text{-}C_6)$alkoxy group;
(c40) a halo$(C_1\text{-}C_6)$alkoxyhalo$(C_1\text{-}C_6)$alkoxy group;
(c41) a mercapto group;
(c42) a $(C_1\text{-}C_{12})$alkylthio group;
(c43) a $(C_2\text{-}C_{12})$alkenylthio group;
(c44) a $(C_2\text{-}C_{12})$alkynylthio group;
(c45) a $(C_3\text{-}C_{12})$cycloalkylthio group;
(c46) a halo$(C_1\text{-}C_{12})$alkylthio group;
(c47) a halo$(C_2\text{-}C_{12})$alkenylthio group;
(c48) a halo$(C_2\text{-}C_{12})$alkynylthio group;
(c49) a halo$(C_3\text{-}C_{12})$cycloalkylthio group;
(c50) a $(C_3\text{-}C_{12})$cycloalkyl$(C_1\text{-}C_{12})$alkylthio group;
(c51) a halo$(C_3\text{-}C_{12})$cycloalkyl$(C_1\text{-}C_{12})$alkylthio group;
(c52) a $(C_1\text{-}C_6)$alkoxy$(C_1\text{-}C_6)$alkylthio group;
(c53) a halo$(C_1\text{-}C_6)$alkoxy$(C_1\text{-}C_6)$alkylthio group;
(c54) a $(C_1\text{-}C_6)$alkoxyhalo$(C_1\text{-}C_6)$alkylthio group;
(c55) a halo$(C_1\text{-}C_6)$alkoxyhalo$(C_1\text{-}C_6)$alkylthio group;
(c56) a $(C_1\text{-}C_{12})$alkylsulfinyl group;
(c57) a $(C_2\text{-}C_{12})$alkenylsulfinyl group;
(c58) a $(C_2\text{-}C_{12})$alkynylsulfinyl group;
(c59) a $(C_3\text{-}C_{12})$cycloalkylsulfinyl group;
(c60) a halo$(C_1\text{-}C_{12})$alkylsulfinyl group;
(c61) a halo$(C_2\text{-}C_{12})$alkenylsulfinyl group;
(c62) a halo$(C_2\text{-}C_{12})$alkynylsulfinyl group;
(c63) a halo$(C_3\text{-}C_{12})$cycloalkylsulfinyl group;
(c64) a $(C_3\text{-}C_{12})$cycloalkyl$(C_1\text{-}C_{12})$alkylsulfinyl group;
(c65) a halo$(C_3\text{-}C_{12})$cycloalkyl$(C_1\text{-}C_{12})$alkylsulfinyl group;
(c66) a $(C_1\text{-}C_{12})$alkylsulfonyl group;
(c67) a $(C_2\text{-}C_{12})$alkenylsulfonyl group;
(c68) a $(C_2\text{-}C_{12})$alkynylsulfonyl group;
(c69) a $(C_3\text{-}C_{12})$cycloalkylsulfonyl group;
(c70) a halo$(C_1\text{-}C_{12})$alkylsulfonyl group;
(c71) a halo$(C_2\text{-}C_{12})$alkenylsulfonyl group;
(c72) a halo$(C_2\text{-}C_{12})$alkynylsulfonyl group;
(c73) a halo$(C_3\text{-}C_{12})$cycloalkylsulfonyl group;
(c74) a $(C_3\text{-}C_{12})$cycloalkyl$(C_1\text{-}C_{12})$alkylsulfonyl group;
(c75) a halo$(C_3\text{-}C_{12})$cycloalkyl$(C_1\text{-}C_{12})$alkylsulfonyl group;
(c76) an aryl group;
(c77) an aryl group having, on the ring, the same or different 1 to 5 substituents selected from (a) a halogen atom, (b) a cyano group, (c) a nitro group, (d) a $(C_1\text{-}C_6)$alkyl group, (e) a halo$(C_1\text{-}C_6)$alkyl group, (f) a $(C_1\text{-}C_6)$alkoxy group, (g) a halo$(C_1\text{-}C_6)$alkoxy group, (h) a $(C_2\text{-}C_6)$alkenyloxy group, (i) a halo$(C_2\text{-}C_6)$alkenyloxy group, (j) a $(C_2\text{-}C_6)$alkynyloxy group, (k) a halo$(C_2\text{-}C_6)$alkynyloxy group, (l) a $(C_3\text{-}C_6)$cycloalkoxy group, (m) a halo$(C_3\text{-}C_6)$cycloalkoxy group, (n) a $(C_3\text{-}C_6)$cycloalkyl$(C_1\text{-}C_6)$alkoxy group, (o) a halo$(C_3\text{-}C_6)$cycloalkyl$(C_1\text{-}C_6)$alkoxy group, (p) a $(C_1\text{-}C_6)$alkylthio group, (q) a halo$(C_1\text{-}C_6)$alkylthio group, (r) a $(C_1\text{-}C_6)$alkylsulfinyl group, (s) a halo$(C_1\text{-}C_6)$alkylsulfinyl group, (t) a $(C_1\text{-}C_6)$alkylsulfonyl group, (u) a halo$(C_1\text{-}C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)NOR^5$ group wherein $R^4$ and $R^5$ are as defined above;
(c78) an aryl$(C_1\text{-}C_6)$alkyl group;
(c79) an aryl$(C_1\text{-}C_6)$alkyl group having, on the ring, the same or different 1 to 5 substituents selected from (a) a halogen atom, (b) a cyano group, (c) a nitro group, (d) a $(C_1\text{-}C_6)$alkyl group, (e) a halo$(C_1\text{-}C_6)$alkyl group, (f) a $(C_1\text{-}C_6)$alkoxy group, (g) a halo$(C_1\text{-}C_6)$alkoxy group, (h) a $(C_2\text{-}C_6)$alkenyloxy group, (i) a halo$(C_2\text{-}C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)NOR^5$ group wherein $R^4$ and $R^5$ are as defined above;

(c80) an aryloxy group;

(c81) an aryloxy group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)NOR^5$ group wherein $R^4$ and $R^5$ are as defined above;

(c82) an aryloxy$(C_1-C_6)$alkyl group;

(c83) an aryloxy$(C_1-C_6)$alkyl group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)NOR^5$ group wherein $R^4$ and $R^5$ are as defined above;

(c84) an arylthio group;

(c85) an arylthio group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo$(C_1-C_6)$alkylthio group, (r) a $(C_2-C_6)$alkylsulfinyl group, (s) a halo$(C_2-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)NOR^5$ group wherein $R^4$ and $R^5$ are as defined above;

(c86) a halo$(C_1-C_6)$alkylenedioxy group;

(c87) a $(C_1-C_6)$alkoxy$(C_1-C_6)$alkoxy group;

(c88) a $(C_3-C_8)$alkylene group;

(c89) a $(C_1-C_6)$alkyl$(C_3-C_8)$alkylene group;

(c90) a tri$(C_1-C_{12})$alkylsilyloxy group wherein the alkyl groups may be the same or different;

(c91) a tri$(C_1-C_{12})$alkylsilyl$(C_1-C_6)$alkoxy group wherein the alkyl groups may be the same or different;

(c92) a di$(C_1-C_{12})$alkylhalo$(C_1-C_6)$alkylsilyl group wherein the alkyl groups may be the same or different;

(c93) a di$(C_1-C_{12})$alkyl$(C_1-C_6)$alkylthio$(C_1-C_6)$alkylsilyl group wherein the alkyl groups may be the same or different;

(c94) a di$(C_1-C_{12})$alkylhydroxysilyl group wherein the alkyl groups may be the same or different;

(c95) a di$(C_1-C_{12})$alkylhydrosilyl group wherein the alkyl groups may be the same or different;

(c96) a di$(C_1-C_{12})$alkylphenylsilyl group wherein the alkyl groups may be the same or different;

(c97) a $(C_1-C_6)$alkylthio$(C_1-C_6)$alkoxy group;

(c98) a $(C_1-C_6)$alkylsulfinyl$(C_1-C_6)$alkoxy group;

(c99) a $(C_1-C_6)$alkylsulfonyl$(C_1-C_6)$alkoxy group;

(c100) a $(C_1-C_6)$alkoxycarbonyl$(C_1-C_6)$alkoxy group;

(c101) a $(C_1-C_6)$alkylcarbonyl$(C_1-C_6)$alkoxy group;

(c102) a cyano$(C_1-C_6)$alkoxy group;

(c103) an aryl$(C_1-C_6)$alkoxy group wherein the alkoxy moiety may be halogenated;

(c104) an aryl$(C_1-C_6)$alkoxy group wherein the alkoxy moiety may be halogenated, which has, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo$(C_1-C_6)$alkylthio group, (r) a $(C_2-C_6)$ alkylsulfinyl group, (s) a halo($C_2$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$$R^5$ group wherein $R^4$ and $R^5$ are as defined above, (y) an N($R^4$)SO$_2$$R^5$ group wherein $R^4$ and $R^5$ are as defined above, (z) a COR$^4$ group wherein $R^4$ is as defined above, (aa) a CO$_2$$R^4$ group wherein $R^4$ is as defined above, (bb) a CON($R^4$)$R^5$ group wherein $R^4$ and $R^5$ are as defined above, and (cc) a C($R^4$)NOR$^5$ group wherein $R^4$ and $R^5$ are as defined above;

(c105) a hydroxy($C_1$-$C_6$)alkyl group;

(c106) a ($C_1$-$C_6$)alkylthio($C_1$-$C_6$)alkylcarbonyl group;

(c107) a ($C_1$-$C_6$)alkylthio($C_1$-$C_6$)alkyl group;

(c108) a tri($C_1$-$C_{12}$)alkylsilyl($C_1$-$C_6$)alkylthio group wherein the alkyl groups of the tri($C_1$-$C_{12}$)alkylsilyl may be the same or different;

(c109) a tri($C_1$-$C_{12}$)alkylsilyl($C_1$-$C_6$)alkylsulfinyl group wherein the alkyl groups of the tri($C_1$-$C_{12}$)alkylsilyl may be the same or different;

(c110) a tri($C_1$-$C_{12}$)alkylsilyl($C_1$-$C_6$)alkylsulfonyl group wherein the alkyl groups of the tri($C_1$-$C_{12}$)alkylsilyl may be the same or different;

(c111) a $R^4$($R^5$)N($C_1$-$C_6$)alkyl group wherein $R^4$ and $R^5$ are as defined above;

(c112) a heterocyclic group;

(c113) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$) alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$) alkyl group wherein the alkyl groups of the tri($C_1$-$C_6$) alkylsilyl may be the same or different, (v) a tri($C_1$-$C_6$) alkylsilyl($C_2$-$C_6$)alkynyl group wherein the alkyl groups may be the same or different, and (w) an oxo group;

(c114) a heterocyclyloxy group;

(c115) a heterocyclyloxy group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo ($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo ($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c116) a heterocyclylthio group;

(c117) a heterocyclylthio group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo ($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo ($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c118) a heterocyclylsulfinyl group;

(c119) a heterocyclylsulfinyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo ($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo ($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c120) a heterocyclylsulfonyl group;

(c121) a heterocyclylsulfonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo ($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo ($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c122) a heterocyclyl($C_1$-$C_6$)alkyloxy group;

(c123) a heterocyclylalkyloxy group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo ($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo ($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)N$ carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c124) a ($C_1$-$C_{12}$)alkyl($C_3$-$C_{12}$)cycloalkyl group;
(c125) a halo($C_1$-$C_{12}$)alkyl($C_3$-$C_{12}$)cycloalkyl group;
(c126) a ($C_1$-$C_6$)alkylsulfinyl($C_1$-$C_6$)alkyl group;
(c127) a di($C_1$-$C_{12}$)alkylbenzylsilyl group wherein the alkyl groups may be the same or different;
(c128) a heterocyclyl($C_1$-$C_6$)alkyl group;
(c129) a heterocyclyl($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)N$ carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group, (c130) a heterocyclyloxy($C_1$-$C_6$)alkyl group; or
(c131) a heterocyclyloxy($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)N$ carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group, or X can form, together with the adjacent $R^2$ or $R^3$, (c132) a bicyclo ring, wherein the bicyclo ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group; or X can form, together with the adjacent X on an aromatic ring, (c133) a bicyclo ring or (c134) a fused ring, wherein the bicyclo ring or fused ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group, and m is an integer of 0 to 5, or salts thereof.

2. The benzyloxypyrimidine derivative of claim 1, wherein m is as defined in claim 1, $R^1$ is (a1) a hydrogen atom;
(a2) a ($C_1$-$C_6$)alkyl group;
(a3) a ($C_3$-$C_7$)cycloalkyl group (said cycloalkyl group is optionally fused with a benzene ring);
(a4) a ($C_2$-$C_6$)alkenyl group;
(a5) a ($C_2$-$C_6$)alkynyl group;
(a6) a halo($C_1$-$C_6$)alkyl group;
(a10) a ($C_1$-$C_6$)alkoxy($C_1$-$C_6$)alkyl group;
(a11) a ($C_3$-$C_6$)cycloalkyl($C_1$-$C_6$)alkyl group;
(a12) a ($C_1$-$C_6$)alkylthio($C_1$-$C_6$)alkyl group;
(a13) a ($C_1$-$C_6$)alkylsulfinyl($C_1$-$C_6$)alkyl group;
(a14) a ($C_1$-$C_6$)alkylsulfonyl($C_1$-$C_6$)alkyl group;
(a16) a halo($C_3$-$C_6$)cycloalkyl($C_1$-$C_6$)alkyl group;
(a22) an aryl($C_1$-$C_6$)alkyl group;
(a23) an aryl($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)N$ carbonyl group wherein $R^4$ and $R^5$ are as defined in claim 1;
(a24) a cyano($C_1$-$C_6$)alkyl group;
(a30) an aryl group;
(a31) an aryl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)N$ carbonyl group wherein $R^4$ and $R^5$ are as defined above, and (t) a phenoxy group;
(a32) an arylsulfonyl group;
(a33) an arylsulfonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)N$ carbonyl group wherein $R^4$ and $R^5$ are as defined above;

(a34) an arylcarbonyl group;

(a35) an arylcarbonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)N$ carbonyl group wherein $R^4$ and $R^5$ are as defined above;

(a44) a ($C_1$-$C_6$)alkylcarbonyl group;

(a52) a heterocyclic group;

(a53) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)N$ carbonyl group wherein $R^4$ and $R^5$ are as defined above, and (t) an oxo group;

(a54) a heterocyclyl($C_1$-$C_6$)alkyl group;

(a55) a heterocyclyl($C_1$-$C_6$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)N$ carbonyl group wherein $R^4$ and $R^5$ are as defined above, and (t) an oxo group;

(a56) a tri($C_1$-$C_6$)alkylsilyl($C_1$-$C_6$)alkyl group wherein the alkyl groups of the tri($C_1$-$C_6$)alkylsilyl may be the same or different; or (a57) a $R^4(R^5)NCO$ group wherein $R^4$ and $R^5$ are as defined above, A is —O—, —S—, —SO— or —$SO_2$—, $R^2$ and $R^3$ may be the same or different and each is (b1) a hydrogen atom;

(b2) a ($C_1$-$C_6$)alkyl group;

(b3) a ($C_3$-$C_6$)cycloalkyl group;

(b6) a halo($C_1$-$C_6$)alkyl group;

(b11) a ($C_1$-$C_6$)alkoxy($C_1$-$C_6$)alkyl group;

(b12) a ($C_1$-$C_6$)alkylthio($C_1$-$C_6$)alkyl group; or (b13) a ($C_1$-$C_6$)alkoxycarbonyl group, and X may be the same or different and each is (c1) a hydrogen atom;

(c2) a halogen atom;

(c5) a nitro group;

(c14) a ($C_1$-$C_{12}$)alkyl group;

(c17) a ($C_3$-$C_{12}$)cycloalkyl group;

(c18) a halo($C_1$-$C_{12}$)alkyl group;

(c21) a halo($C_3$-$C_{12}$)cycloalkyl group;

(c22) a tri($C_1$-$C_{12}$)alkylsilyl group wherein the alkyl groups may be the same or different;

(c27) a ($C_1$-$C_{12}$)alkoxy group;

(c30) a ($C_3$-$C_{12}$)cycloalkyloxy group (said cycloalkyl is optionally fused with a benzene ring);

(c31) a halo($C_1$-$C_{12}$)alkoxy group;

(c38) a halo($C_1$-$C_6$)alkoxy($C_1$-$C_6$)alkoxy group;

(c42) a ($C_1$-$C_{12}$)alkylthio group;

(c46) a halo($C_1$-$C_{12}$)alkylthio group;

(c56) a ($C_1$-$C_{12}$)alkylsulfinyl group;

(c66) a ($C_1$-$C_{12}$)alkylsulfonyl group;

(c80) an aryloxy group;

(c81) an aryloxy group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)NOR^5$ group wherein $R^4$ and $R^5$ are as defined above;

(c112) a heterocyclic group;

(c113) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)N$ carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c114) a heterocyclyloxy group;

(c115) a heterocyclyloxy group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo $(C_1-C_6)$alkoxy group, (i) a $(C_3-C_6)$cycloalkyl$(C_1-C_6)$alkoxy group, (j) a $(C_1-C_6)$alkylthio group, (k) a halo $(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;

(c130) a heterocyclyloxy$(C_1-C_6)$alkyl group; or (c131) a heterocyclyloxy$(C_1-C_6)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group, or X can form, together with the adjacent $R^2$ or $R^3$, (c132) a bicyclo ring, wherein the bicyclo ring optionally has the same or different one or more substituents selected from (a) a halogen atom, (b) a $(C_1-C_6)$alkyl group, (c) a halo $(C_1-C_6)$alkyl group, (d) a $(C_1-C_6)$alkoxy group, (e) a halo$(C_1-C_6)$alkoxy group, (f) a $(C_1-C_6)$alkylthio group, (g) a halo$(C_1-C_6)$alkylthio group, (h) a $(C_1-C_6)$alkylsulfinyl group, (i) a halo$(C_1-C_6)$alkylsulfinyl group, (j) a $(C_1-C_6)$alkylsulfonyl group, and (k) a halo$(C_1-C_6)$alkylsulfonyl group; or, X can form, together with the adjacent X on an aromatic ring, (c133) a bicyclo ring or (C134) a fused ring, wherein the bicyclo ring or fused ring optionally has the same or different one or more substituents selected from (a) a halogen atom, (b) a $(C_1-C_6)$alkyl group, (c) a halo $(C_1-C_6)$alkyl group, (d) a $(C_1-C_6)$alkoxy group, (e) a halo$(C_1-C_6)$alkoxy group, (f) a $(C_1-C_6)$alkylthio group, (g) a halo$(C_1-C_6)$alkylthio group, (h) a $(C_1-C_6)$alkylsulfinyl group, (i) a halo$(C_1-C_6)$alkylsulfinyl group, (j) a $(C_1-C_6)$alkylsulfonyl group, and (k) a halo$(C_1-C_6)$alkylsulfonyl group, or salts thereof.

3. An agrohorticultural insecticide composition comprising (a) the benzyloxypyrimidine derivative according to claim 1 or a salt thereof as an active ingredient and (b) an inert carrier.

4. A method of using an agrohorticultural insecticide, which comprises treating a plant or soil with the active ingredient of the agrohorticultural insecticide according to claim 3.

5. A method of controlling an agrohorticultural pest, which comprises treating a plant or soil with an effective amount of the benzyloxypyrimidine derivative according to claim 1 or a salt thereof.

6. An ectoparasite controlling agent composition comprising (a) the benzyloxypyrimidine derivative according to claim 1 or a salt thereof as an active ingredient and (b) a domestic animal-acceptable carrier.

7. A method of controlling an ectoparasite, which comprises treating the ectoparasite with an effective amount of the benzyloxypyrimidine derivative according to claim 1 or a salt thereof.

8. An agrohorticultural insecticide composition comprising (a) the benzyloxypyrimidine derivative according to claim 2 or a salt thereof as an active ingredient and (b) an inert carrier.

9. A method of using an agrohorticultural insecticide, which comprises treating a plant or soil with the active ingredient of the agrohorticultural insecticide according to claim 8.

10. A method of controlling an agrohorticultural pest, which comprises treating a plant or soil with an effective amount of the benzyloxypyrimidine derivative according to claim 2 or a salt thereof.

11. An ectoparasite controlling agent composition comprising (a) the benzyloxypyrimidine derivative according to claim 2 or a salt thereof as an active ingredient and (b) a domestic animal-acceptable carrier.

12. A method of controlling an ectoparasite, which comprises treating the ectoparasite with an effective amount of the benzyloxypyrimidine derivative according to claim 2 or a salt thereof.

13. A composition comprising (a) the benzyloxypyrimidine derivative according to claim 1 or a salt thereof and (b) an inert carrier.

14. A composition comprising (a) the benzyloxypyrimidine derivative according to claim 2 or a salt thereof and (b) an inert carrier.

* * * * *